(12) United States Patent
Kenedy et al.

(10) Patent No.: US 7,941,434 B2
(45) Date of Patent: May 10, 2011

(54) EFFICIENTLY COMPILING CO-ASSOCIATING BIOATTRIBUTES

(75) Inventors: Andrew Alexander Kenedy, Sugar Land, TX (US); Charles Anthony Eldering, Furlong, PA (US)

(73) Assignee: Expanse Networks, Inc., Furlong, PA (US)

( * ) Notice: Subject to any disclaimer, the term of this patent is extended or adjusted under 35 U.S.C. 154(b) by 417 days.

(21) Appl. No.: 12/031,669

(22) Filed: Feb. 14, 2008

(65) Prior Publication Data

US 2008/0228820 A1 Sep. 18, 2008

Related U.S. Application Data

(60) Provisional application No. 60/895,236, filed on Mar. 16, 2007.

(51) Int. Cl.
*G06F 7/00* (2006.01)
*G06F 17/30* (2006.01)

(52) U.S. Cl. .......... 707/737; 702/19; 707/706; 707/713; 707/803

(58) Field of Classification Search .......... 707/736–757, 707/802–812
See application file for complete search history.

(56) References Cited

U.S. PATENT DOCUMENTS

| | | | |
|---|---|---|---|
| 5,769,074 A | 6/1998 | Barnhill | |
| 5,940,802 A | 8/1999 | Hildebrand | |
| 5,985,559 A | 11/1999 | Brown | |
| 6,108,647 A * | 8/2000 | Poosala et al. | 702/180 |
| 6,203,993 B1 | 3/2001 | Shuber | |
| 6,506,562 B1 | 1/2003 | Weissman | |
| 6,507,840 B1 * | 1/2003 | Ioannidis et al. | 707/999.004 |
| 6,519,604 B1 * | 2/2003 | Acharya et al. | 707/738 |
| 6,694,311 B1 * | 2/2004 | Smith | 707/999.004 |
| 6,730,023 B1 | 5/2004 | Dodds | |
| 6,912,492 B1 | 6/2005 | Johnson | |
| 6,931,326 B1 | 8/2005 | Judson | |
| 6,994,962 B1 | 2/2006 | Thilly | |
| 7,054,758 B2 | 5/2006 | Gill-Garrison | |
| 7,072,794 B2 | 7/2006 | Wittkowski | |
| 7,107,155 B2 | 9/2006 | Frudakis | |
| 7,127,355 B2 | 10/2006 | Cox | |
| 2002/0010552 A1 | 1/2002 | Rienhoff | |
| 2002/0077775 A1 | 6/2002 | Schork | |

(Continued)

FOREIGN PATENT DOCUMENTS

WO    WO0127857 A2    4/2001

(Continued)

OTHER PUBLICATIONS

Das, S. Filters, wrappers and a boosting-based hybrid for feature selection. In Proceedings of the Eighteenth International Conference on Machine Learning, 74-81 (Morgan Kaufmann Publishers Inc., San Francisco, CA, USA, 2001).*

(Continued)

*Primary Examiner* — Lori A. Clow
*Assistant Examiner* — Soren Harward

(57) ABSTRACT

A bioinformatics method, software, database and system are presented in which attribute profiles of query-attribute-positive individuals and query-attribute-negative individuals are compared, and combinations of pangenetic and non-pangenetic attributes that occur at a higher frequency in the group of query-attribute-positive individuals are identified and stored to generate a compilation of bioattribute combinations that co-associate with the query attribute (i.e., an attribute of interest). Several computationally efficient approaches for identifying the bioattribute combinations are incorporated.

2 Claims, 31 Drawing Sheets

U.S. PATENT DOCUMENTS

| | | |
|---|---|---|
| 2002/0094532 A1 | 7/2002 | Bader |
| 2002/0123058 A1 | 9/2002 | Threadgill |
| 2002/0126545 A1* | 9/2002 | Warren et al. ............ 365/200 |
| 2002/0128860 A1 | 9/2002 | Leveque |
| 2002/0133299 A1 | 9/2002 | Jacob |
| 2002/0137086 A1 | 9/2002 | Olek |
| 2003/0040002 A1 | 2/2003 | Ledley |
| 2003/0065241 A1 | 4/2003 | Hohnloser |
| 2003/0065535 A1 | 4/2003 | Karlov |
| 2003/0130873 A1 | 7/2003 | Nevin |
| 2003/0198970 A1 | 10/2003 | Roberts |
| 2003/0224394 A1 | 12/2003 | Schadt |
| 2003/0233377 A1 | 12/2003 | Kovac |
| 2004/0015337 A1 | 1/2004 | Thomas |
| 2004/0018500 A1 | 1/2004 | Glassbrook |
| 2004/0019598 A1 | 1/2004 | Huang |
| 2004/0024534 A1 | 2/2004 | Hsu |
| 2004/0158581 A1 | 8/2004 | Kotlyar |
| 2004/0175700 A1 | 9/2004 | Geesaman |
| 2004/0193019 A1 | 9/2004 | Wei |
| 2004/0197799 A1 | 10/2004 | Williamson |
| 2004/0221855 A1 | 11/2004 | Ashton |
| 2005/0021240 A1 | 1/2005 | Berlin |
| 2005/0032066 A1 | 2/2005 | Heng |
| 2005/0037405 A1 | 2/2005 | Caspi |
| 2005/0090718 A1 | 4/2005 | Dodds |
| 2005/0143928 A1 | 6/2005 | Moser |
| 2005/0158788 A1 | 7/2005 | Schork |
| 2005/0170528 A1 | 8/2005 | West |
| 2005/0176057 A1 | 8/2005 | Bremer |
| 2005/0191678 A1 | 9/2005 | Lapointe |
| 2005/0216208 A1 | 9/2005 | Saito |
| 2005/0256649 A1 | 11/2005 | Roses |
| 2005/0260610 A1 | 11/2005 | Kurtz |
| 2006/0129034 A1 | 6/2006 | Kasabov |
| 2006/0200319 A1 | 9/2006 | Brown |

FOREIGN PATENT DOCUMENTS

| | | | |
|---|---|---|---|
| WO | WO0150214 A2 | | 7/2001 |
| WO | WO0210456 A2 | | 2/2002 |
| WO | WO0222165 A1 | | 3/2002 |
| WO | WO02080079 A2 | | 10/2002 |
| WO | WO03060652 A2 | | 7/2003 |
| WO | WO03076895 A2 | | 9/2003 |
| WO | WO2004031912 A2 | | 4/2004 |
| WO | WO2004048551 A2 | | 6/2004 |
| WO | WO2004051548 A2 | | 6/2004 |
| WO | WO2004075010 A2 | | 9/2004 |
| WO | WO2004097577 A2 | | 11/2004 |
| WO | WO 2005/086891 | * | 9/2005 |
| WO | WO2006052952 A2 | | 5/2006 |
| WO | WO2006084195 A2 | | 8/2006 |
| WO | WO2007061881 A2 | | 5/2007 |

OTHER PUBLICATIONS

Duan, K.-B. B., Rajapakse, J. C., Wang, H. & Azuaje, F. Multiple svm-rfe for gene selection in cancer classification with expression data. IEEE transactions on nanobioscience 4, 228-234 (2005).*

Nielsen, T. et al. Molecular characterisation of soft tissue tumours: a gene expression study. The Lancet 359, 1301-1307 (2002).*

Vrbsky, S. V. & Liu, J. W. S. Approximate-A Query Processor That Produces Monotonically Improving Approximate Answers. IEEE Transactions on Knowledge and Data Engineering 5, 1056-1068 (1993).*

Miyamoto et al., "Diagnostic and Therapeutic Applications of Epigenetics", Japanese Journal of Clinical Oncology, Jun. 1, 2005, pp. 293-301, 35 (6), Keigakul Publishing Company, Japan.

Peedicayil, "Epigenetic Therapy—a New Development in Pharmacology", Indian Journal of Medical Research, Jan. 2006, pp. 17-24, 123 (1), Council of Medical Research, India.

Longato-Stadler et al., "Personality Traits and Platelet Monoamine Oxidase Activity in a Swedish Male Criminal Population", Neuropsychobiology, 2002, pp. 202-208, 46 (4), S. Karger AG, Basel, Switzerland.

Carson et al., Abnormal Psychology and Modern Life, 8th edition, 1988, pp. 56-57, Scott Foresman and Company, Glenview, IL, USA.

Harvard School of Public Health / Harvard Center for Cancer Prevention, "Your Disease Risk" website for calculating disease risk, 34 exemplary pages submitted including heart disease risk estimation and listings of risk factors, last accessed via the world wide web on Apr. 30, 2007, at the URL address: <<http://www.yourdiseaserisk.harvard.edu/english/index.htm>>.

* cited by examiner

A.

| Individual | HTR2A Gene | | | | | | | | |
|---|---|---|---|---|---|---|---|---|---|
| | 96 | 97 | 98 | 99 | 100 | 101 | 102 | 103 | 104 |
| 1 | T | C | C | T | T | C | T | A | C |
| 2 | T | C | C | T | T | C | C | A | C |

B.

| Individual | + Strand from STS#68777 forward primer | | | | | | | | |
|---|---|---|---|---|---|---|---|---|---|
| | 1 | 2 | 3 | 4 | 5 | 6 | 7 | 8 | 9 |
| 1 | T | C | T | T | A | C | T | T | G |
| 2 | T | C | T | T | A | C | A | T | G |

C.

| Individual | HTR2A polymorphism 102 |
|---|---|
| 1 | T |
| 2 | C |

D.

| Individual | HTR2A allele |
|---|---|
| 1 | 102 T |
| 2 | 102 C |

| Individual | CpG Methylation Sites - Gene X | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| 1 | M | M | M | U | M | M | M | M | U | M | M | M | U | U | M | M | U | M | M | U |
| 2 | M | U | M | U | U | U | U | U | U | U | U | M | U | U | U | U | U | U | U | U |

B.

| Individual | CpG Methylation - Gene Z | | | | | | | | |
|---|---|---|---|---|---|---|---|---|---|
| | 11 | 12 | 13 | 14 | 15 | 16 | 17 | 18 | 19 |
| 1 | C | G | T | A | A | C | G | C | G |
| 1 | M | | | | | M | | U | |
| 2 | C | G | T | A | A | C | G | C | G |
| 2 | U | | | | | U | | U | |

| Past Smoker | Amount (packs/week) | Age(s) of Exposure | Brand |
|---|---|---|---|
| YES | 10 | 25-27 | Marlboro |

B.

| Past Smoker | Amount (packs / week) | | | | | | | | | | Age(s) of Exposure | | | | | | Age range | Age class | How long (years) | | Total Exposure (packs) | Brand |
|---|---|---|---|---|---|---|---|---|---|---|---|---|---|---|---|---|---|---|---|---|---|---|
| | 10 | >9 | >8 | >7 | >6 | >5 | >4 | >3 | >2 | >1 | 27 | 26 | 25 | >24 | >23 | >2 | >1 | | | | | |
| YES | | | | | | | | | | | | | | | | | | 21-30 | adult | 3 | >2 | >1 | 1560 | Marlboro |

*Fig. 9*

| Query-Attribute-Negative | |
|---|---|
| Individual | Attributes |
| 1 | A |
| 2 | X |
| 3 | X |
| 4 | A |
| 5 | X |
| 6 | A |

Frequencies

Individual attributes:

(A) = 50%
(X) = 50%

Attribute combinations:

(A X) = 0%

| Query-Attribute-Positive | |
|---|---|
| Individual | Attributes |
| 7 | |
| 8 | A, X |
| 9 | A, X |
| 10 | |
| 11 | |
| 12 | A, X |

Frequencies

Individual attributes:

(A) = 50%
(X) = 50%

Attribute combinations:

| QUERY-ATTRIBUTE-NEGATIVE | | | |
|---|---|---|---|
| | Gene 1 | Gene 2 | Gene 3 |
| Individ. 1 | A | C | B |
| Individ. 2 | B | A | C |
| Individ. 3 | C | B | A |

Frequencies

Indvidual attributes:

| Gene 1 | Gene 2 | Gene 3 |
|---|---|---|
| (A) = 33% | (A) = 33% | (A) = 33% |
| (B) = 33% | (B) = 33% | (B) = 33% |
| (C) = 33% | (C) = 33% | (C) = 33% |

Attribute combinations:
(A A A) = 0%
(B B B) = 0%
(C C C) = 0%

| QUERY-ATTRIBUTE-POSITIVE | | | |
|---|---|---|---|
| | Gene 1 | Gene 2 | Gene 3 |
| Individ. 4 | A | A | A |
| Individ. 5 | B | B | B |
| Individ. 6 | C | C | C |

Frequencies

Individual attributes:

| Gene 1 | Gene 2 | Gene 3 |
|---|---|---|
| (A) = 33% | (A) = 33% | (A) = 33% |
| (B) = 33% | (B) = 33% | (B) = 33% |
| (C) = 33% | (C) = 33% | (C) = 33% |

Attribute combinations:
(A A A) = 33%
(B B B) = 33%
(C C C) = 33%

|  | Query-attribute-positive | Query-attribute-negative |
|---|---|---|
| Exposed | a | b |
| Unexposed | c | d |

B.

| Frequency of occurrence for attribute-positive group | Frequency of occurrence for attribute-negative group |
|---|---|
| Frequency $= \dfrac{a}{a+c}$ | Frequency $= \dfrac{b}{b+d}$ |
| Absolute Risk $= \dfrac{a}{a+b}$ | Relative Risk $= \dfrac{\frac{a}{a+b}}{\frac{c}{c+d}}$ |
| Odds $= \dfrac{\frac{a}{a+b}}{\frac{b}{a+b}}$ | Odds Ratio $= \dfrac{a/b}{c/d} = \dfrac{ad}{bc}$ |

Fig. 12

| Individual | Attributes | | | | | | | | | | | | | | | | | | | | | | | | | |
|---|---|---|---|---|---|---|---|---|---|---|---|---|---|---|---|---|---|---|---|---|---|---|---|---|---|---|
| | A | B | C | D | E | F | G | H | I | J | K | L | M | N | O | P | Q | R | S | T | U | V | W | X | Y | Z |
| 1 | 1 | 0 | 1 | 1 | 1 | 1 | 1 | 1 | 0 | 1 | 0 | 1 | 1 | 1 | 1 | 1 | 0 | 1 | 1 | 1 | 1 | 1 | 0 | 1 | 1 | 0 |
| 2 | 1 | 0 | 1 | 1 | 1 | 1 | 1 | 1 | 0 | 1 | 0 | 1 | 1 | 1 | 1 | 1 | 0 | 1 | 1 | 1 | 1 | 1 | 0 | 1 | 1 | 0 |
| 3 | 1 | 0 | 1 | 1 | 1 | 1 | 1 | 1 | 0 | 1 | 0 | 1 | 1 | 1 | 1 | 1 | 0 | 1 | 1 | 1 | 1 | 1 | 0 | 1 | 1 | 0 |
| 4 | 1 | 0 | 1 | 1 | 1 | 1 | 1 | 1 | 0 | 1 | 0 | 1 | 1 | 0 | 1 | 1 | 0 | 1 | 1 | 1 | 1 | 1 | 0 | 1 | 1 | 0 |
| 5 | 1 | 0 | 1 | 1 | 1 | 1 | 1 | 1 | 0 | 1 | 0 | 1 | 1 | 0 | 1 | 1 | 0 | 1 | 1 | 1 | 1 | 1 | 0 | 1 | 1 | 0 |
| 6 | 1 | 0 | 1 | 1 | 1 | 1 | 1 | 1 | 0 | 1 | 0 | 1 | 1 | 0 | 1 | 1 | 0 | 1 | 1 | 0 | 1 | 1 | 0 | 1 | 1 | 0 |
| 7 | 1 | 0 | 1 | 1 | 1 | 0 | 1 | 1 | 1 | 1 | 1 | 1 | 1 | 0 | 1 | 1 | 1 | 1 | 0 | 1 | 1 | 1 | 1 | 0 | 0 | 0 |
| 8 | 1 | 0 | 1 | 1 | 1 | 0 | 1 | 1 | 1 | 1 | 1 | 1 | 1 | 0 | 1 | 1 | 1 | 1 | 1 | 0 | 1 | 1 | 1 | 1 | 0 | 0 |
| 9 | 1 | 0 | 0 | 1 | 1 | 0 | 1 | 1 | 1 | 1 | 1 | 1 | 1 | 0 | 1 | 1 | 1 | 1 | 1 | 0 | 1 | 1 | 1 | 1 | 0 | 0 |
| 10 | 1 | 0 | 0 | 1 | 1 | 0 | 1 | 1 | 1 | 1 | 1 | 1 | 1 | 0 | 1 | 1 | 1 | 1 | 1 | 0 | 1 | 1 | 1 | 1 | 0 | 0 |
| 11 | 0 | 0 | 1 | 1 | 1 | 1 | 1 | 1 | 1 | 1 | 0 | 1 | 1 | 0 | 1 | 1 | 0 | 1 | 1 | 0 | 1 | 1 | 0 | 1 | 1 | 0 |
| 12 | 0 | 0 | 1 | 1 | 1 | 0 | 1 | 1 | 1 | 1 | 1 | 1 | 1 | 0 | 1 | 1 | 0 | 1 | 1 | 1 | 1 | 1 | 0 | 1 | 1 | 0 |
| 13 | 0 | 0 | 1 | 1 | 1 | 0 | 1 | 1 | 1 | 1 | 1 | 0 | 1 | 1 | 0 | 1 | 1 | 1 | 1 | 0 | 1 | 1 | 0 | 1 | 1 | 0 |
| 14 | 0 | 0 | 1 | 1 | 1 | 0 | 1 | 1 | 1 | 1 | 0 | 1 | 1 | 1 | 1 | 0 | 1 | 1 | 1 | 1 | 1 | 1 | 1 | 1 | 1 | 0 |
| 15 | 0 | 0 | 1 | 1 | 1 | 1 | 1 | 1 | 0 | 1 | 1 | 1 | 1 | 0 | 1 | 1 | 0 | 1 | 1 | 0 | 1 | 1 | 0 | 1 | 0 | 0 |
| 16 | 0 | 0 | 1 | 1 | 1 | 0 | 1 | 1 | 0 | 1 | 1 | 1 | 1 | 0 | 1 | 1 | 0 | 1 | 1 | 1 | 1 | 1 | 1 | 1 | 1 | 0 |
| 17 | 0 | 0 | 0 | 1 | 1 | 1 | 1 | 1 | 1 | 0 | 1 | 1 | 1 | 1 | 1 | 1 | 1 | 1 | 1 | 1 | 1 | 1 | 0 | 1 | 1 | 0 |
| 18 | 0 | 0 | 1 | 1 | 1 | 1 | 1 | 1 | 0 | 1 | 0 | 1 | 1 | 0 | 1 | 1 | 1 | 1 | 0 | 1 | 1 | 0 | 1 | 0 | 0 | 0 |
| 19 | 0 | 0 | 0 | 1 | 0 | 1 | 1 | 1 | 0 | 1 | 0 | 1 | 1 | 1 | 1 | 1 | 1 | 1 | 1 | 1 | 1 | 1 | 1 | 0 | 0 | 0 |
| 20 | 0 | 0 | 1 | 1 | 1 | 1 | 1 | 1 | 0 | 1 | 0 | 1 | 1 | 0 | 1 | 1 | 0 | 1 | 1 | 0 | 1 | 1 | 1 | 1 | 0 | 0 |
| 111 | 0 | 0 | 1 | 1 | 1 | 1 | 1 | 1 | 0 | 1 | 0 | 1 | 1 | 0 | 1 | 1 | 1 | 1 | 1 | 1 | 1 | 1 | 0 | 1 | 1 | 0 |

| Individual | Attributes | | | | | |
|---|---|---|---|---|---|---|
| 1 | C | E | F | N | T | Y |

B.

| 6 choose 6 | 6 choose 5 | 6 choose 4 | 6 choose 3 | 6 choose 2 |
|---|---|---|---|---|
| CEFNTY | CEFNT | CEFN | CEF | CE |
|  | CEFNY | CEFT | CEN | CF |
|  | CEFTY | CEFY | CET | EF |
|  | CENTY | CENT | CEY | CT |
|  | CFNTY | CENY | CFN | CY |
|  | EFNTY | CETY | CNT | CN |
|  |  | CFNT | CTY | EN |
|  |  | CFNY | CFT | ET |
|  |  | CFTY | CFY | EY |
|  |  | CNTY | CNY | FN |
|  |  | EFNT | EFN | FT |
|  |  | EFNY | EFT | FY |
|  |  | EFTY | EFY | NT |
|  |  | ENTY | ENT | NY |
|  |  | FNTY | ETY | TY |
|  |  |  | ENY |  |
|  |  |  | FNT |  |
|  |  |  | FNY |  |
|  |  |  | FTY |  |
|  |  |  | NTY |  |

*Fig. 15*

| Attribute Combination | Frequency in Negative Individuals | Frequency in Positive Individuals | Query Attribute= A | | Query Attribute= A | |
|---|---|---|---|---|---|---|
| | | | Absolute Risk | Relative Risk | Odds | Odds Ratio |
| CEFNTY | 0/101 | 3/10 | 1.00 | 15.3 | Undef. | Undef. |
| CEFNT | 0/101 | 3/10 | 1.00 | 15.3 | Undef. | Undef. |
| CEFNY | 0/101 | 3/10 | 1.00 | 15.3 | Undef. | Undef. |
| CENTY | 10/101 | 3/10 | 0.23 | 3.2 | 0.30 | 3.9 |
| CFNTY | 0/101 | 3/10 | 1.00 | 15.3 | Undef. | Undef. |
| EFNTY | 10/101 | 3/10 | 0.23 | 3.2 | 0.30 | 3.9 |
| CEFTY | 1/101 | 5/10 | 0.83 | 18.3 | 5.00 | 100.0 |
| CEFN | 0/101 | 3/10 | 1.00 | 15.3 | Undef. | Undef. |
| CEFT | 1/101 | 5/10 | 0.83 | 18.3 | 5.00 | 100.0 |
| CEFY | 11/101 | 6/10 | 0.35 | 9.2 | 0.55 | 13.6 |
| CENT | 10/101 | 3/10 | 0.23 | 3.2 | 0.30 | 3.9 |
| CENY | 10/101 | 3/10 | 0.23 | 3.2 | 0.30 | 3.9 |
| CETY | 31/101 | 3/10 | 0.09 | 1.0 | 0.10 | 1.0 |
| ⫮ | | | | | | |
| CEF | 41/101 | 6/10 | 0.13 | 2.0 | 0.15 | 2.2 |
| CEN | 10/101 | 3/10 | 0.23 | 3.2 | 0.30 | 3.9 |
| CET | 31/101 | 5/10 | 0.14 | 2.1 | 0.16 | 2.3 |
| ⫮ | | | | | | |
| CE | 81/101 | 8/10 | 0.09 | 1.0 | 0.10 | 1.0 |
| CF | 41/101 | 6/10 | 0.13 | 2.0 | 0.15 | 2.2 |
| EF | 51/101 | 6/10 | 0.11 | 1.4 | 0.12 | 1.5 |
| CT | 31/101 | 5/10 | 0.14 | 2.1 | 0.16 | 2.3 |
| ET | 41/101 | 5/10 | 0.11 | 1.4 | 0.12 | 1.5 |
| ⫮ | | | | | | |
| TY | 41/101 | 5/10 | 0.11 | 1.4 | 0.12 | 1.5 |

*Fig. 16*

| Attribute Combination | Frequency in Negative Individuals | Frequency in Positive Individuals | Query Attribute= A | | Query Attribute= A | |
|---|---|---|---|---|---|---|
| | | | Absolute Risk | Relative Risk | Odds | Odds Ratio |
| CEFNTY | 0/101 | 3/10 | 1.00 | 15.3 | Undef. | Undef. |
| CEFNT | 0/101 | 3/10 | 1.00 | 15.3 | Undef. | Undef. |
| CEFNY | 0/101 | 3/10 | 1.00 | 15.3 | Undef. | Undef. |
| CENTY | 10/101 | 3/10 | 0.23 | 3.2 | 0.30 | 3.9 |
| CFNTY | 0/101 | 3/10 | 1.00 | 15.3 | Undef. | Undef. |
| EFNTY | 10/101 | 3/10 | 0.23 | 3.2 | 0.30 | 3.9 |
| CEFTY | 1/101 | 5/10 | 0.83 | 18.3 | 5.00 | 100.0 |
| CEFN | 0/101 | 3/10 | 1.00 | 15.3 | Undef. | Undef. |
| CEFT | 1/101 | 5/10 | 0.83 | 18.3 | 5.00 | 100.0 |
| CEFY | 11/101 | 6/10 | 0.35 | 9.2 | 0.55 | 13.6 |
| CENT | 10/101 | 3/10 | 0.23 | 3.2 | 0.30 | 3.9 |
| CENY | 10/101 | 3/10 | 0.23 | 3.2 | 0.30 | 3.9 |
| ⁎ | | | | | | |
| CEF | 41/101 | 6/10 | 0.13 | 2.0 | 0.15 | 2.2 |
| CEN | 10/101 | 3/10 | 0.23 | 3.2 | 0.30 | 3.9 |
| CET | 31/101 | 5/10 | 0.14 | 2.1 | 0.16 | 2.3 |
| ⁎ | | | | | | |
| CF | 41/101 | 6/10 | 0.13 | 2.0 | 0.15 | 2.2 |
| EF | 51/101 | 6/10 | 0.11 | 1.4 | 0.12 | 1.5 |
| CT | 31/101 | 5/10 | 0.14 | 2.1 | 0.16 | 2.3 |
| ET | 41/101 | 5/10 | 0.11 | 1.4 | 0.12 | 1.5 |
| ⁎ | | | | | | |
| TY | 41/101 | 5/10 | 0.11 | 1.4 | 0.12 | 1.5 |

Fig. 17

| Attribute Combination | Frequency in Negative Individuals | Frequency in Positive Individuals | Query Attribute= A | | Query Attribute= A | |
|---|---|---|---|---|---|---|
| | | | Absolute Risk | Relative Risk | Odds | Odds Ratio |
| CEFNTY | 0/101 | 3/10 | 1.00 | 15.3 | Undef. | Undef. |
| CEFNT | 0/101 | 3/10 | 1.00 | 15.3 | Undef. | Undef. |
| CEFNY | 0/101 | 3/10 | 1.00 | 15.3 | Undef. | Undef. |
| CFNTY | 0/101 | 3/10 | 1.00 | 15.3 | Undef. | Undef. |
| CEFTY | 1/101 | 5/10 | 0.83 | 18.3 | 5.00 | 100.0 |
| CEFN | 0/101 | 3/10 | 1.00 | 15.3 | Undef. | Undef. |
| CEFT | 1/101 | 5/10 | 0.83 | 18.3 | 5.00 | 100.0 |
| CEFY | 11/101 | 6/10 | 0.35 | 9.2 | 0.55 | 13.6 |

*Fig. 18*

| Attribute Combination | Rank | Query Attribute= A ||
|---|---|---|---|
| | | Absolute Risk | Relative Risk |
| CEFNTY | 1 | 1.00 | 15.3 |
| CEFNT | 2 | 1.00 | 15.3 |
| CEFNY | 2 | 1.00 | 15.3 |
| CFNTY | 2 | 1.00 | 15.3 |
| CEFN | 3 | 1.00 | 15.3 |
| CEFTY | 4 | 0.83 | 18.3 |
| CEFT | 5 | 0.83 | 18.3 |
| CEFY | 6 | 0.35 | 9.2 |
| EFNTY | 7 | 0.23 | 3.2 |
| CENTY | 7 | 0.23 | 3.2 |
| CENT | 8 | 0.23 | 3.2 |
| CENY | 8 | 0.23 | 3.2 |
| CEN | 9 | 0.23 | 3.2 |
| CET | 10 | 0.14 | 2.1 |
| CT | 11 | 0.14 | 2.1 |
| CEF | 12 | 0.13 | 2.0 |
| CF | 13 | 0.13 | 2.0 |
| EF | 14 | 0.11 | 1.4 |
| TY | 31 | 0.11 | 1.4 |

| Individual | Attributes | | | | | | | | | | | | | | | | | | | | | | | | | |
|---|---|---|---|---|---|---|---|---|---|---|---|---|---|---|---|---|---|---|---|---|---|---|---|---|---|---|
| | A | B | C | D | E | F | G | H | I | J | K | L | M | N | O | P | Q | R | S | T | U | V | W | X | Y | Z |
| 112 | 0 | 0 | 1 | 1 | 1 | 1 | 1 | 1 | 0 | 1 | 0 | 1 | 1 | 1 | 1 | 0 | 1 | 1 | 1 | 1 | 1 | 0 | 1 | 1 | 1 | 0 |

B.

| Attribute Combination | Frequency in Negative Individuals | Frequency in Positive Individuals | Query Attribute= A | |
|---|---|---|---|---|
| | | | Absolute Risk | Relative Risk |
| CEFNTY | 0/101 | 3/10 | 1.00 | 15.3 |
| CEFNT | 0/101 | 3/10 | 1.00 | 15.3 |
| CEFNY | 0/101 | 3/10 | 1.00 | 15.3 |
| ⋮ | | | | |
| TY | 41/101 | 5/10 | 0.11 | 1.4 |
| Attribute Combination | Frequency in Negative Individuals | Frequency in Positive Individuals | Query Attribute= W | |
| | | | Absolute Risk | Relative Risk |
| CEIKQ | 0/67 | 2/44 | 1.00 | 2.6 |
| CEKQ | 0/67 | 2/44 | 1.00 | 2.6 |
| CEIK | 10/67 | 2/44 | 0.17 | 0.4 |
| CEIQ | 10/67 | 2/44 | 0.17 | 0.4 |
| CEI | 30/67 | 12/44 | 0.29 | 0.6 |
| CEK | 20/67 | 12/44 | 0.38 | 0.9 |
| CEQ | 21/67 | 2/44 | 0.09 | 0.2 |
| ⋮ | | | | |
| CE | 57/67 | 32/44 | 0.36 | 0.7 |

| Query Attribute | Predisposing Attribute Combination | Frequency in Negative Individuals | Frequency in Positive Individuals | Absolute Risk | Relative Risk |
|---|---|---|---|---|---|
| A | CEFNTY | 0/101 | 3/10 | 1.00 | 15.3 |
| W | CE | 57/67 | 32/44 | 0.36 | 0.7 |

B.

| Predisposition to 'A' | | |
|---|---|---|
| Predisposing Attribute Combination | Absolute Potential | Relative Potential |
| CEFNTY | 100% | 15.3 x |

| Predisposition to 'W' | | |
|---|---|---|
| Predisposing Attribute Combination | Absolute Potential | Relative Potential |
| CE | 36% | 0.7 x |

| Individual | Attributes | | | | | | | | | | | | | | | | | | | | | | | | | |
|---|---|---|---|---|---|---|---|---|---|---|---|---|---|---|---|---|---|---|---|---|---|---|---|---|---|---|
| | A | B | C | D | E | F | G | H | I | J | K | L | M | N | O | P | Q | R | S | T | U | V | W | X | Y | Z |
| 113 | 0 | 0 | 1 | 1 | 1 | 1 | 1 | 1 | 1 | 0 | 1 | 0 | 1 | 1 | 0 | 1 | 1 | 0 | 1 | 1 | 0 | 1 | 1 | 0 | 1 | 0 | 0 |

B.

| Attribute Combination | Query Attribute= A | |
|---|---|---|
| | Absolute Risk | Relative Risk |
| CEFNTY | 1.00 | 15.3 |
| CEFNT | 1.00 | 15.3 |
| CEFNY | 1.00 | 15.3 |
| CEFTY | 0.83 | 18.3 |
| CEFN | 1.00 | 15.3 |
| CEFT | 0.83 | 18.3 |
| CEFY | 0.35 | 9.2 |
| CEF | 0.13 | 2.0 |
| CE | 0.09 | 1.0 |
| CF | 0.13 | 2.0 |
| EF | 0.11 | 1.4 |

C.

| Attribute Combination | Query Attribute= A | |
|---|---|---|
| | Absolute Risk | Relative Risk |
| CEFNTY | 1.00 | 15.3 |
| CEFNT | 1.00 | 15.3 |
| CEFNY | 1.00 | 15.3 |
| CEFN | 1.00 | 15.3 |
| CEFTY | 0.83 | 18.3 |
| CEFT | 0.83 | 18.3 |
| CEFY | 0.35 | 9.2 |
| | | |
| CEF | 0.13 | 2.0 |
| | | |
| CF | 0.13 | 2.0 |
| EF | 0.11 | 1.4 |
| CE | 0.09 | 1.0 |

| Individual | Attributes | | | | | | | | | | | | | | | | | | | | | | | | | |
|---|---|---|---|---|---|---|---|---|---|---|---|---|---|---|---|---|---|---|---|---|---|---|---|---|---|---|
| | A | B | C | D | E | F | G | H | I | J | K | L | M | N | O | P | Q | R | S | T | U | V | W | X | Y | Z |
| 114 | 0 | 0 | 1 | 1 | 1 | 1 | 0 | 1 | 1 | 0 | 1 | 0 | 1 | 1 | 0 | 1 | 1 | 0 | 1 | 1 | 1 | 1 | 0 | 1 | 0 | 0 |

B.

| Attribute Combination | Query Attribute= A | |
|---|---|---|
| | Absolute Risk | Relative Risk |
| CEFNTY | 1.00 | 15.3 |
| CEFNT | 1.00 | 15.3 |
| CENTY | 0.23 | 3.2 |
| CEFTY | 0.83 | 18.3 |
| CEFT | 0.83 | 18.3 |
| CENT | 0.23 | 3.2 |
| CETY | 0.09 | 1.0 |
| CET | 0.14 | 2.1 |
| CE | 0.09 | 1.0 |
| CT | 0.14 | 2.1 |
| ET | 0.11 | 1.4 |

C.

| Attribute Combination | Query Attribute= A | |
|---|---|---|
| | Absolute Potential | Relative Potential |
| CEFNTY | 100% | 15.3 x |
| CEFNT | 100% | 15.3 x |
| CEFTY | 83% | 18.3 x |
| CEFT | 83% | 18.3 x |
| CENTY | 23% | 3.2 x |
| CENT | 23% | 3.2 x |
| | | |
| CET | 14% | 2.1 x |
| | | |
| ET | 11% | 1.4 x |
| CE | 9% | 1.0 x |

| Attribute Combination | Frequency in Negative Individuals | Frequency in Positive Individuals | Query Attribute= W | |
|---|---|---|---|---|
| | | | Absolute Risk | Relative Risk |
| ACEIKQ | 0/67 | 2/44 | 1.00 | 2.6 |
| ACEIK | 0/67 | 2/44 | 1.00 | 2.6 |
| ACEIQ | 0/67 | 2/44 | 1.00 | 2.6 |
| ACEKQ | 0/67 | 2/44 | 1.00 | 2.6 |
| ACEI | 0/67 | 2/44 | 1.00 | 2.6 |
| ACEK | 0/67 | 2/44 | 1.00 | 2.6 |
| ACEQ | 0/67 | 2/44 | 1.00 | 2.6 |
| ACE | 6/67 | 2/44 | 0.25 | 0.6 |

B.

| Attribute Combination | Frequency in Negative Individuals | Frequency in Positive Individuals | Query Attribute= W | |
|---|---|---|---|---|
| | | | Absolute Risk | Relative Risk |
| CEIKQ | 0/67 | 2/44 | 1.00 | 2.6 |
| CEKQ | 0/67 | 2/44 | 1.00 | 2.6 |
| CEIK | 10/67 | 2/44 | 0.17 | 0.4 |
| CEIQ | 10/67 | 2/44 | 0.17 | 0.4 |
| CEI | 30/67 | 12/44 | 0.29 | 0.6 |
| CEK | 20/67 | 12/44 | 0.38 | 0.9 |
| CEQ | 21/67 | 2/44 | 0.09 | 0.2 |
| CE | 57/67 | 32/44 | 0.36 | 0.7 |

*Fig. 29*

EFFICIENTLY COMPILING CO-ASSOCIATING BIOATTRIBUTES

This application claims priority to U.S. Provisional Application Ser. No. 60/895,236, which was filed on Mar. 16, 2007, and which is incorporated herein by reference in its entirety.

BRIEF DESCRIPTION OF THE DRAWINGS

The following detailed description will be better understood when read in conjunction with the appended drawings, in which there is shown one or more of the multiple embodiments of the present invention. It should be understood, however, that the various embodiments are not limited to the precise arrangements and instrumentalities shown in the drawings.

FIG. 3 illustrates examples of genetic attributes;

FIG. 4 illustrates examples of epigenetic attributes;

FIG. 9 illustrates an example of expansion and reformatting of attributes;

FIG. 10 illustrates the advantage of identifying attribute combinations in a two attribute example;

FIG. 11 illustrates the advantage of identifying attribute combinations in a three attribute example;

FIG. 12 illustrates an example of statistical measures & formulas useful for the methods;

FIG. 14 illustrates a 1st dataset example for a method of creating an attribute combinations database;

FIG. 15 illustrates 2nd dataset and combinations table examples for a method of creating an attribute combinations database;

FIG. 16 illustrates a 3rd dataset example for a method of creating an attribute combinations database;

FIG. 17 illustrates a 4th dataset example for a method of creating an attribute combinations database;

FIG. 18 illustrates a 4th dataset example for a method of creating an attribute combinations database;

FIG. 20 illustrates a rank-ordered tabulated results example for a method of identifying predisposing attribute combinations;

FIG. 22 illustrates 1st and 2nd dataset examples for a method of predisposition prediction;

FIG. 23 illustrates 3rd dataset and tabulated results examples for a method of predisposition prediction;

FIG. 25 illustrates 1st dataset, 3rd dataset and tabulated results examples for destiny modification of individual #113;

FIG. 26 illustrates 1st dataset, 3rd dataset and tabulated results examples for destiny modification of individual #114;

FIG. 29 illustrates 3rd dataset examples from a method of destiny modification for use in synergy discovery;

DETAILED DESCRIPTION

Figure 1:
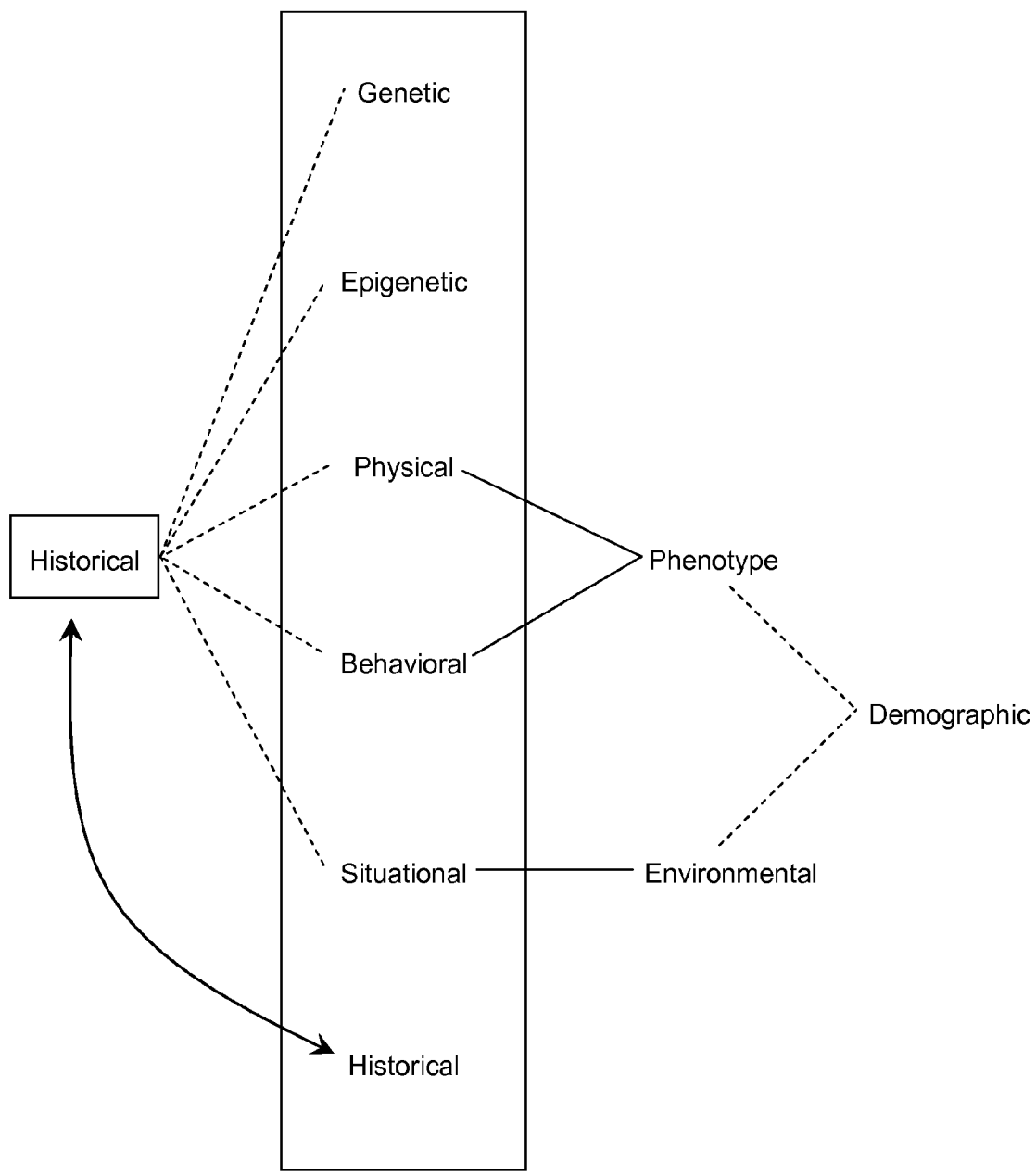
FIG. 1 illustrates attribute categories and their relationships.

Disclosed herein are methods, computer systems, databases and software for identifying combinations of attributes associated with individuals that co-occur (i.e., co-associate, co-aggregate) with attributes of interest, such as specific disorders, behaviors and traits. Disclosed herein are databases as well as database systems for creating and accessing databases describing those attributes and for performing analyses based on those attributes. The methods, computer systems and software are useful for identifying intricate combinations of attributes that predispose human beings toward having or developing specific disorders, behaviors and traits of interest, determining the level of predisposition of an individual towards such attributes, and revealing which attribute associations can be added or eliminated to effectively modify what may have been hereto believed to be destiny. The methods, computer systems and software are also applicable for tissues and non-human organisms, as well as for identifying combinations of attributes that correlate with or cause behaviors and outcomes in complex non-living systems including molecules, electrical and mechanical systems and various devices and apparatus whose functionality is dependent on a multitude of attributes.

Previous methods have been largely unsuccessful in determining the complex combinations of attributes that predispose individuals to most disorders, behaviors and traits. The level of resolution afforded by the data typically used is too low, the number and types of attributes considered is too limited, and the sensitivity to detect low frequency, high complexity combinations is lacking. The desirability of being able to determine the complex combinations of attributes that predispose an individual to physical or behavioral disorders has clear implications for improving individualized diagnoses, choosing the most effective therapeutic regimens, making beneficial lifestyle changes that prevent disease and promote health, and reducing associated health care expenditures. It is also desirable to determine those combinations of attributes that promote certain behaviors and traits such as success in sports, music, school, leadership, career and relationships.

Advances in technology within the field of genetics now provide the ability to achieve maximum resolution of the entire genome. Discovery and characterization of epigenetic modifications—reversible chemical modifications of DNA and structural modification of chromatin that dramatically alter gene expression—has provided an additional level of information that may be altered due to environmental conditions, life experiences and aging. Along with a collection of diverse nongenetic attributes including physical, behavioral, situational and historical attributes associated with an organism, the present invention provides the ability to utilize the above information to enable prediction of the predisposition of an organism toward developing a specific attribute of interest provided in a query.

There are approximately 25,000 genes in the human genome. Of these, approximately 1,000 of these genes are involved in monogenic disorders, which are disorders whose sole cause is due to the properties of a single gene. This collection of disorders represents less than two percent of all human disorders. The remaining 98 percent of human disorders, termed complex disorders, are caused by multiple genetic influences or a combination of multiple genetic and non-genetic influences, still yet to be determined due to their resistance to current methods of discovery.

Previous methods using genetic information have suffered from either a lack of high resolution information, very limited coverage of total genomic information, or both. Genetic markers such as single nucleotide polymorphisms (SNPs) do not provide a complete picture of a gene's nucleotide sequence or the total genetic variability of the individual. The SNPs typically used occur at a frequency of at least 5% in the population. However, the majority of genetic variation that exists in the population occurs at frequencies below 1%. Furthermore, SNPs are spaced hundreds of nucleotides apart and do not account for genetic variation that occurs in the genetic sequence lying between, which is vastly more sequence than the single nucleotide position represented by an SNP. SNPs are typically located within gene coding regions and do not allow consideration of 98% of the 3 billion base pairs of genetic code in the human genome that does not encode gene sequences. Other markers such as STS, gene locus markers and chromosome loci markers also provide very low resolution and incomplete coverage of the genome. Complete and partial sequencing of an individual's genome provides the ability to incorporate that detailed information into the analysis of factors contributing toward expressed attributes.

Genomic influence on traits is now known to involve more than just the DNA nucleotide sequence of the genome. Regulation of expression of the genome can be influenced significantly by epigenetic modification of the genomic DNA and chromatin (3-dimensional genomic DNA with bound proteins). Termed the epigenome, this additional level of information can make genes in an individual's genome behave as if they were absent. Epigenetic modification can dramatically affect the expression of approximately at least 6% of all genes.

Epigenetic modification silences the activity of gene regulatory regions required to permit gene expression. Genes can undergo epigenetic silencing as a result of methylation of cytosines occurring in CpG dinucleotide motifs, and to a lesser extent by deacetylation of chromatin-associated histone proteins which inhibit gene expression by creating 3-dimensional conformational changes in chromatin. Assays such as bisulfite sequencing, differential methyl hybridization using microarrays, methylation sensitive polymerase chain reaction, and mass spectrometry enable the detection of cytosine nucleotide methylation while chromosome immunoprecipitation (CHIP) can be used to detect histone acetylation states of chromatin.

In one embodiment, epigenetic attributes are incorporated in the present invention to provide certain functionality. First, major mental disorders such as schizophrenia and bipolar mood disorder are thought to be caused by or at least greatly influenced by epigenetic imprinting of genes. Second, all epigenetic modification characterized to date is reversible in nature, allowing for the potential therapeutic manipulation of the epigenome to alter the course and occurrence of disease and certain behaviors. Third, because epigenetic modification of the genome occurs in response to experiences and stimuli encountered during prenatal and postnatal life, epigenetic data can help fill gaps resulting from unobtainable personal data, and reinforce or even substitute for unreliable self-reported data such as life experiences and environmental exposures.

In addition to genetic and epigenetic attributes, which can be referred to collectively as pangenetic attributes, numerous other attributes likely influence the development of traits and disorders. These other attributes, which can be referred to collectively as non-pangenetic attributes, can be categorized individually as physical, behavioral, or situational attributes. FIG. 1 displays one embodiment of the attribute categories and their interrelationships according to the present invention and illustrates that physical and behavioral attributes can be collectively equivalent to the broadest classical definition of phenotype, while situational attributes can be equivalent to those typically classified as environmental. In one embodiment, historical attributes can be viewed as a separate category containing a mixture of genetic, epigenetic, physical, behavioral and situational attributes that occurred in the past. Alternatively, historical attributes can be integrated within the genetic, epigenetic, physical, behavioral and situational categories provided they are made readily distinguishable from those attributes that describe the individual's current state. In one embodiment, the historical nature of an attribute is accounted for via a time stamp or other time based marker associated with the attribute. As such, there are no explicit historical attributes, but through use of time stamping, the time associated with the attribute can be used to make a determination as to whether the attribute is occurring in what would be considered the present, or if it has occurred in the past. Traditional demographic factors are typically a small subset of attributes derived from the phenotype and environmental categories and can be therefore represented within the physical, behavioral and situational categories.

In the present invention the term 'attributes' rather than the term 'factors' is used since many of the entities are characteristics associated with an individual that may have no influence on the vast majority of their traits, behaviors and disorders. As such, there may be many instances during execution of the methods disclosed herein when a particular attribute does not act as a factor in determining predisposition. Nonetheless, every attribute remains a potentially important characteristic of the individual and may contribute to predisposition toward some other attribute or subset of attributes queried during subsequent or future implementation of the methods disclosed herein. In the present invention, the term 'bioattribute' can be used to refer to any attribute associated with a biological entity, such as an attribute associated with an organism or an attribute associated with a biologic molecule, for example. Therefore even a numerical address ZIP code, which is not a biological entity, can be a bioattribute when used to describe the residential location associated with a biological entity such as a person.

An individual possesses many associated attributes which may be collectively referred to as an 'attribute profile' associated with that individual. In one embodiment, an attribute profile can be considered as being comprised of the attributes that are present (i.e., occur) in that profile, as well as being comprised of the various combinations (i.e., combinations and subcombinations) of those attributes. The attribute profile of an individual is preferably provided to embodiments of the present invention as a dataset record whose association with the individual can be indicated by a unique identifier contained in the dataset record. An actual attribute of an individual can be represented by an attribute descriptor in attribute profiles, records, datasets, and databases. Herein, both actual attributes and attribute descriptors may be referred to simply as attributes. In one embodiment, statistical relationships and associations between attribute descriptors are a direct result of relationships and associations between actual attributes of an individual. In the present disclosure, the term 'individual' can refer to a singular group, person, organism, organ, tissue, cell, virus, molecule, thing, entity or state, wherein a state includes but is not limited to a state-of-being, an operational state or a status. Individuals, attribute profiles and attributes can be real and/or measurable, or they may be hypothetical and/or not directly observable.

In one embodiment the present invention can be used to discover combinations of attributes regardless of number or type, in a population of any size, that cause predisposition to an attribute of interest. In doing so, this embodiment also has the ability to provide a list of attributes one can add or subtract from an existing profile of attributes in order to respectively increase or decrease the strength of predisposition toward the attribute of interest. The ability to accurately detect predisposing attribute combinations naturally benefits from being supplied with datasets representing large numbers of individuals and having a large number and variety of attributes for each. Nevertheless, the present invention will function properly with a minimal number of individuals and attributes. One embodiment of the present invention can be used to detect not only attributes that have a direct (causal) effect on an attribute of interest, but also those attributes that do not have a direct effect such as instrumental variables (i.e., correlative attributes), which are attributes that correlate with and can be used to predict predisposition for the attribute of interest but are not causal. For simplicity of terminology, both types of attributes are referred to herein as predisposing attributes, or simply attributes, that contribute toward predisposition toward the attribute of interest, regardless of whether the contribution or correlation is direct or indirect.

It is beneficial, but not necessary, in most instances, that the individuals whose data is supplied for the method be representative of the individual or population of individuals for which the predictions are desired. In a preferred embodiment, the attribute categories collectively encompass all potential attributes of an individual. Each attribute of an individual can be appropriately placed in one or more attribute categories of the methods, system and software of the invention. Attributes and the various categories of attributes can be defined as follows:
 a) attribute: a quality, trait, characteristic, relationship, property, factor or object associated with or possessed by an individual;
 b) genetic attribute: any genome, genotype, haplotype, chromatin, chromosome, chromosome locus, chromosomal material, deoxyribonucleic acid (DNA), allele, gene, gene cluster, gene locus, gene polymorphism, gene mutation, gene marker, nucleotide, single nucleotide polymorphism (SNP), restriction fragment length polymorphism (RFLP), variable tandem repeat (VTR), genetic marker, sequence marker, sequence tagged site (STS), plasmid, transcription unit, transcription product, ribonucleic acid (RNA), and copy DNA (cDNA), including the nucleotide sequence and encoded amino acid sequence of any of the above;
 c) epigenetic attribute: any feature of the genetic material—all genomic, vector and plasmid DNA, and chromatin—that affects gene expression in a manner that is heritable during somatic cell divisions and sometimes heritable in germline transmission, but that is nonmutational to the DNA sequence and is therefore fundamentally reversible, including but not limited to methylation of DNA nucleotides and acetylation of chromatin-associated histone proteins;
 d) pangenetic attribute: any genetic or epigenetic attribute;
 e) physical attribute: any material quality, trait, characteristic, property or factor of an individual present at the atomic, molecular, cellular, tissue, organ or organism level, excluding genetic and epigenetic attributes;
 f) behavioral attribute: any singular, periodic, or aperiodic response, action or habit of an individual to internal or external stimuli, including but not limited to an action, reflex, emotion or psychological state that is controlled or created by the nervous system on either a conscious or subconscious level;
 g) situational attribute: any object, condition, influence, or milieu that surrounds, impacts or contacts an individual; and
 h) historical attribute: any genetic, epigenetic, physical, behavioral or situational attribute that was associated with or possessed by an individual in the past. As such, the historical attribute refers to a past state of the individual and may no longer describe the current state.

The methods, systems, software, and databases disclosed herein apply to and are suitable for use with not only humans, but for other organisms as well. The methods, systems, software and databases may also be used for applications that consider attribute identification, predisposition potential and destiny modification for organs, tissues, individual cells, and viruses both in vitro and in vivo. For example, the methods can be applied to behavior modification of individual cells being grown and studied in a laboratory incubator by providing pangenetic attributes of the cells, physical attributes of the cells such as size, shape and surface receptor densities, and situational attributes of the cells such as levels of oxygen and carbon dioxide in the incubator, temperature of the incubator, and levels of glucose and other nutrients in the liquid growth medium. Using these and other attributes, the methods, systems, software and databases can then be used to predict predisposition of the cells for such characteristics as susceptibility to infection by viruses, general growth rate, morphology, and differentiation potential. The methods, systems, software, and databases disclosed herein can also be applied to complex non-living systems to, for example, predict the behavior of molecules or the performance of electrical devices or machinery subject to a large number of variables.

Figure 2:
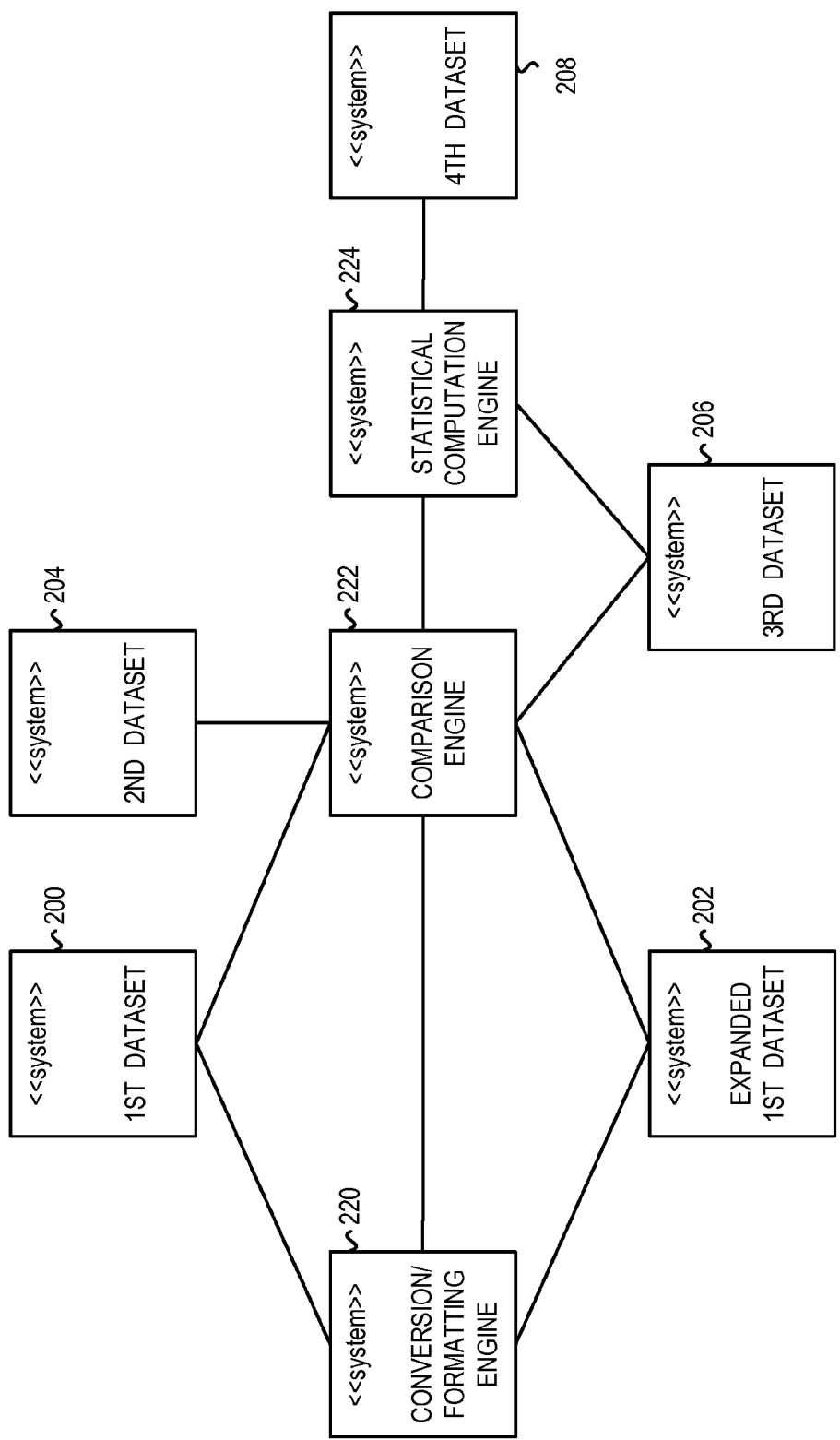
FIG. 2 illustrates a system diagram including data formatting, comparison, and statistical computation engines and dataset input/output for a method of creating an attribute combinations database.

FIG. 2 illustrates system components corresponding to one embodiment of a method, system, software, and databases for compiling predisposing attribute combinations. Attributes can be stored in the various datasets of the system. In one embodiment, 1st dataset 200 is a raw dataset of attributes that may be converted and expanded by conversion/formatting engine 220 into a more versatile format and stored in expanded 1st dataset 202. Comparison engine 222 can perform a comparison between attributes from records of the 1st dataset 200 or expanded 1st dataset 202 to determine candidate predisposing attributes which are then stored in 2nd dataset 204. Comparison engine 222 can tabulate a list of all possible combinations of the candidate attributes and then perform a comparison of those combinations with attributes contained within individual records of 1st dataset 200 or expanded 1st dataset 202. Comparison engine 222 can store those combinations that are found to occur and meet certain selection criteria in 3rd dataset 206 along with a numerical frequency of occurrence obtained as a count during the comparison. Statistical computation engine 224 can perform statistical computations using the numerical frequencies of occurrence to obtain results (values) for strength of association between attributes and attribute combinations and then store those results in 3rd dataset 206. Statistical computation engine 224, alone or in conjunction with comparison engine 222, can create a 4th dataset 208 containing attributes and attribute combinations that meet a minimum or maximum statistical requirement by applying a numerical or statistical filter to the numerical frequencies of occurrence or the values for strength of association stored in 3rd dataset 206. Although represented as a system and engines, the system and engines can be considered subsystems of a larger system, and as such referred to as subsystems. Such subsystems may be implemented as sections of code, objects, or classes of objects within a single system, or may be separate hardware and software platforms which are integrated with other subsystems to form the final system.

FIGS. 3A and 3B show a representative form for genetic attributes as DNA nucleotide sequence with each nucleotide position associated with a numerical identifier. In this form, each nucleotide is treated as an individual genetic attribute, thus providing maximum resolution of the genomic information of an individual. FIG. 3A depicts a portion of the known gene sequence for the HTR2A gene for two individuals having a nucleotide difference at nucleotide sequence position number 102. Comparing known genes simplifies the task of properly phasing nucleotide sequence comparisons. However, for comparison of non-gene sequences, due to the presence of insertions and deletions of varying size in the genome of one individual versus another, markers such as STS sequences can be used to allow for a proper in-phase comparison of the DNA sequences between different individuals. FIG. 3B shows genomic DNA plus-strand sequence for two individuals beginning at the STS#68777 forward primer which provides a known location of the sequence within the genome and facilitates phasing of the sequence with other sequences from that region of the genome during sequence comparison.

Conversion/formatting engine 220 of FIG. 2 can be used in conjunction with comparison engine 222 to locate and number the STS marker positions within the sequence data and store the resulting data in expanded 1st dataset 202. In one embodiment, comparison engine 222 has the ability to recognize strings of nucleotides with a word size large enough to enable accurately phased comparison of individual nucleotides in the span between marker positions. This function is also valuable in comparing known gene sequences. Nucleotide sequence comparisons in the present invention can also involve transcribed sequences in the form of mRNA, tRNA, rRNA, and cDNA sequences which all derive from genomic DNA sequence and are handled in the same manner as nucleotide sequences of known genes.

FIGS. 3C and 3D show two other examples of genetic attributes that may be compared in one embodiment of the present invention and the format they may take. Although not preferred because of the relatively small amount of information provided, SNP polymorphisms (FIG. 3C) and allele identity (FIG. 3D) can be processed by one or more of the methods herein to provide a limited comparison of the genetic content of individuals.

FIGS. 4A and 4B show examples of epigenetic data that can be compared, the preferred epigenetic attributes being methylation site data. FIG. 4A represents a format of methylation data for hypothetical Gene X for two individuals, where each methylation site (methylation variable position) is distinguishable by a unique alphanumeric identifier. The identifier may be further associated with a specific gene, site or chromosomal locus of the genome. In this embodiment, the methylation status at each site is an attribute that can have either of two values: methylated (M) or unmethylated (U). Other epigenetic data and representations of epigenetic data can be used to perform the methods disclosed herein, and to construct the systems, software and databases disclosed herein, as will be understood by one skilled in the art.

As shown in FIG. 4B, an alternative way to organize epigenetic methylation data is to append it directly to the corresponding genetic sequence attribute dataset as methylation status at each candidate CpG dinucleotide occurring in that genomic nucleotide sequence, in this example for hypothetical Gene Z for two individuals. The advantage of this format is that it inherently includes chromosome, gene and nucleotide position information. In this format, which is the most complete and informative format for the raw data, the epigenetic data can be extracted and converted to another format at any time. Both formats (that of FIG. 4A as well as that of FIG. 4B) provide the same resolution of methylation data, but it is preferable to adhere to one format in order to facilitate comparison of epigenetic data between different individuals. Regarding either data format, in instances where an individual is completely lacking a methylation site due to a deletion or mutation of the corresponding CpG dinucleotide, the corresponding epigenetic attribute value should be omitted (i.e., assigned a null).

Figure 5:
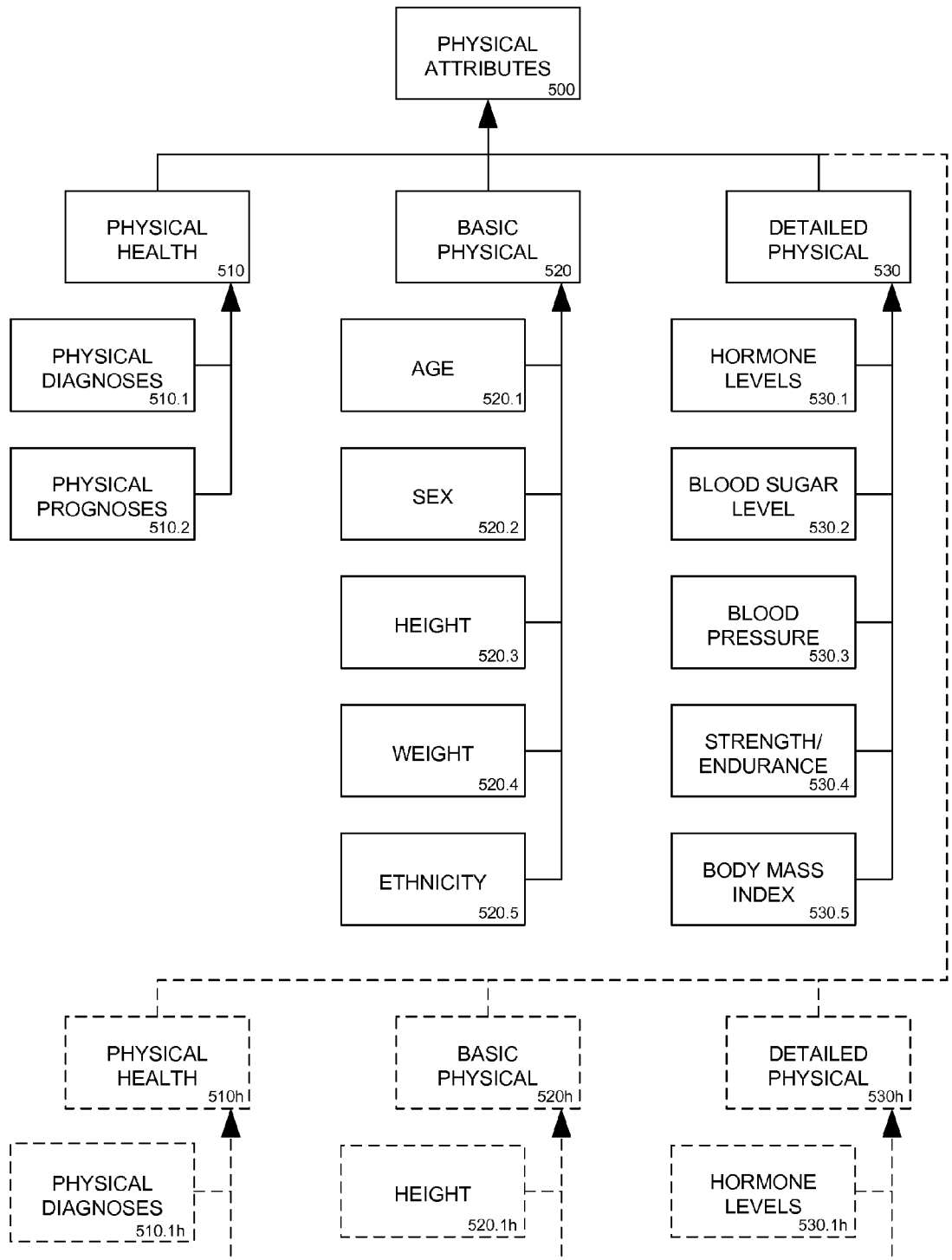
FIG. 5 illustrates representative physical attributes classes.

FIG. 5 illustrates representative classes of physical attributes as defined by physical attributes metaclass 500, which can include physical health class 510, basic physical class 520, and detailed physical class 530, for example. In one embodiment physical health class 510 includes a physical diagnoses subclass 510.1 that includes the following specific attributes (objects), which when positive indicate a known physical diagnoses:

510.1.1 Diabetes
510.1.2 Heart Disease
510.1.3 Osteoporosis
510.1.4 Stroke
510.1.5 Cancer
510.1.5.1 Prostate Cancer
510.1.5.2 Breast Cancer
510.1.5.3 Lung Cancer
510.1.5.4 Colon Cancer
510.1.5.5 Bladder Cancer
510.1.5.6 Endometrial Cancer
510.1.5.7 Non-Hodgkin's Lymphoma
510.1.5.8 Ovarian Cancer
510.1.5.9 Kidney Cancer
510.1.5.10 Leukemia
510.1.5.11 Cervical Cancer
510.1.5.12 Pancreatic Cancer
510.1.5.13 Skin melanoma
510.1.5.14 Stomach Cancer
510.1.6 Bronchitis
510.1.7 Asthma
510.1.8 Emphysema The above classes and attributes represent the current condition of the individual. In the event that the individual (e.g. consumer 810) had a diagnosis for an ailment in the past, the same classification methodology can be applied, but with an "h" placed after the attribute number to denote a historical attribute. For example, 510.1.4h can be used to create an attribute to indicate that the individual suffered a stroke in the past, as opposed to 510.1.4 which indicates the individual is currently suffering a stroke or the immediate aftereffects. Using this approach, historical classes and attributes mirroring the current classes and attributes can be created, as illustrated by historical physical health class 510h, historical physical diagnoses class 510.1h, historical basic physical class 520h, historical height class 520.1h, historical detailed physical class 530h, and historical hormone levels class 530.1h. In an alternate embodiment historical classes and historical attributes are not utilized. Rather, time stamping of the diagnoses or event is used. In this approach, an attribute of 510.1.4-05FEB03 would indicate that the individual suffered a stroke on Feb. 5, 2003. Alternate classification schemes and attribute classes/classifications can be used and will be understood by one of skill in the art. In one embodiment, time stamping of attributes is preferred in order to permit accurate determination of those attributes or attribute combinations that are associated with an attribute of interest (i.e., a query attribute or target attribute) in a causative or predictive relationship, or alternatively, those attributes or attribute combinations that are associated with an attribute of interest in a consequential or symptomatic relationship. In one embodiment, only attributes bearing a time stamp that predates the time stamp of the attribute of interest are processed by the methods. In another embodiment, only attributes bearing a time stamp that postdates the time stamp of the attribute of interest are processed by the methods. In another embodiment, both attributes that predate and attributes that postdate an attribute of interest are processed by the methods.

As further shown in FIG. 5, physical prognoses subclass 510.2 can contain attributes related to clinical forecasting of the course and outcome of disease and chances for recovery. Basic physical class 520 can include the attributes age 520.1, sex 520.2, height 520.3, weight 520.4, and ethnicity 520.5, whose values provide basic physical information about the individual. Hormone levels 530.1 and strength/endurance 530.4 are examples of attribute subclasses within detailed physical class 530. Hormone levels 530.1 can include attributes for testosterone level, estrogen level, progesterone level, thyroid hormone level, insulin level, pituitary hormone level, and growth hormone level, for example. Strength/endurance 530.4 can include attributes for various weight lifting capabilities, stamina, running distance and times, and heart rates under various types of physical stress, for example. Blood sugar level 530.2, blood pressure 530.3 and body mass index 530.5 are examples of attributes whose values provide detailed physical information about the individual. Historical physical health class 510h, historical basic physical class 520h and historical detailed physical class 530h are examples of historical attribute classes. Historical physical health class 510h can include historical attribute subclasses such as historical physical diagnoses class 510.h which would include attributes for past physical diagnoses of various diseases and physical health conditions which may or may not be representative of the individual's current health state. Historical basic physical class 520h can include attributes such as historical height class 520.1h which can contain heights measured at particular ages. Historical detailed physical class 530h can include attributes and attribute classes such as the historical hormone levels class 530.1h which would include attributes for various hormone levels measured at various time points in the past.

In one embodiment, the classes and indexing illustrated in FIG. 5 and disclosed above can be matched to health insurance information such as health insurance codes, such that information collected by health care professionals (such as clinician 820 of FIG. 8, which can be a physician, nurse, nurse practitioner or other health care professional) can be directly incorporated as attribute data. In this embodiment, the heath insurance database can directly form part of the attribute database, such as one which can be constructed using the classes of FIG. 5.

Figure 6:
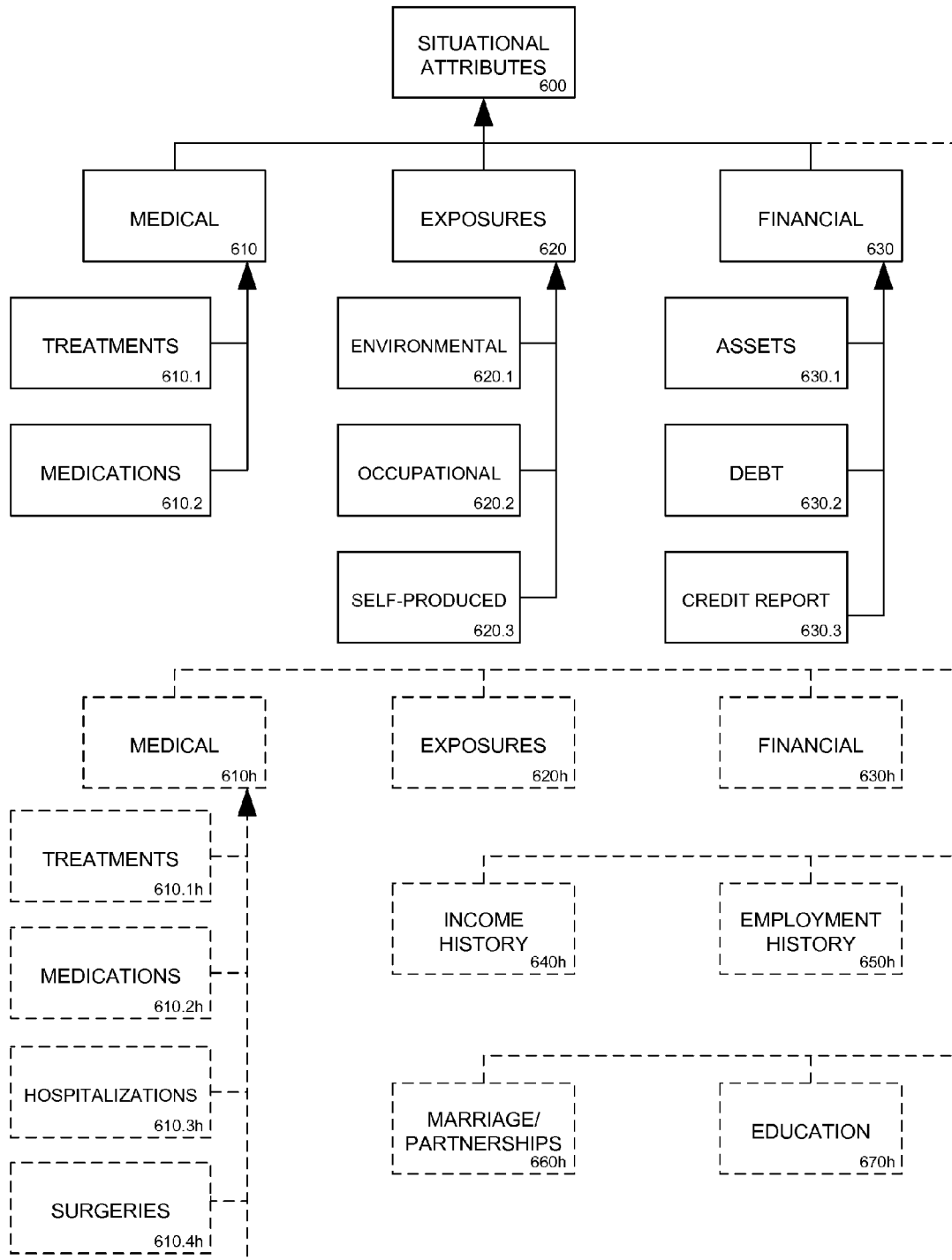
FIG. 6 illustrates representative situational attributes classes.

FIG. 6 illustrates classes of situational attributes as defined by situational attributes metaclass 600, which in one embodiment can include medical class 610, exposures class 620, and financial class 630, for example. In one embodiment, medical class 610 can include treatments subclass 610.1 and medications subclass 610.2; exposures class 620 can include environmental exposures subclass 620.1, occupational exposures subclass 620.2 and self-produced exposures 620.3; and financial class 630 can include assets subclass 630.1, debt subclass 630.2 and credit report subclass 630.3. Historical medical class 610h can include historical treatments subclass 610.1h, historical medications subclass 610.2h, historical hospitalizations subclass 610.3h and historical surgeries subclass 610.4h. Other historical classes included within the situational attributes metaclass 600 can be historical exposures subclass 620h, historical financial subclass 630h, historical income history subclass 640h, historical employment history subclass 650h, historical marriage/partnerships subclass 660h, and historical education subclass 670h.

In one embodiment, commercial databases such as credit databases, databases containing purchase information (e.g. frequent shopper information) can be used as either the basis for extracting attributes for the classes such as those in financial subclass 630 and historical financial subclass 630h, or for direct mapping of the information in those databases to situational attributes. Similarly, accounting information such as that maintained by the consumer 810 of FIG. 8, or a representative of the consumer (e.g. the consumer's accountant) can also be incorporated, transformed, or mapped into the classes of attributes shown in FIG. 6.

Measurement of financial attributes such as those illustrated and described with respect to FIG. 6 allows financial attributes such as assets, debt, credit rating, income and historical income to be utilized in the methods, systems, software and databases described herein. In some instances, such financial attributes can be important with respect to a query attribute. Similarly, other situational attributes such as the number of marriages/partnerships, length of marriages/partnership, number jobs held, income history, can be important attributes and will be found to be related to certain query attributes. In one embodiment a significant number of attributes described in FIG. 6 are extracted from public or private databases, either directly or through manipulation, interpolation, or calculations based on the data in those databases.

Figure 7:
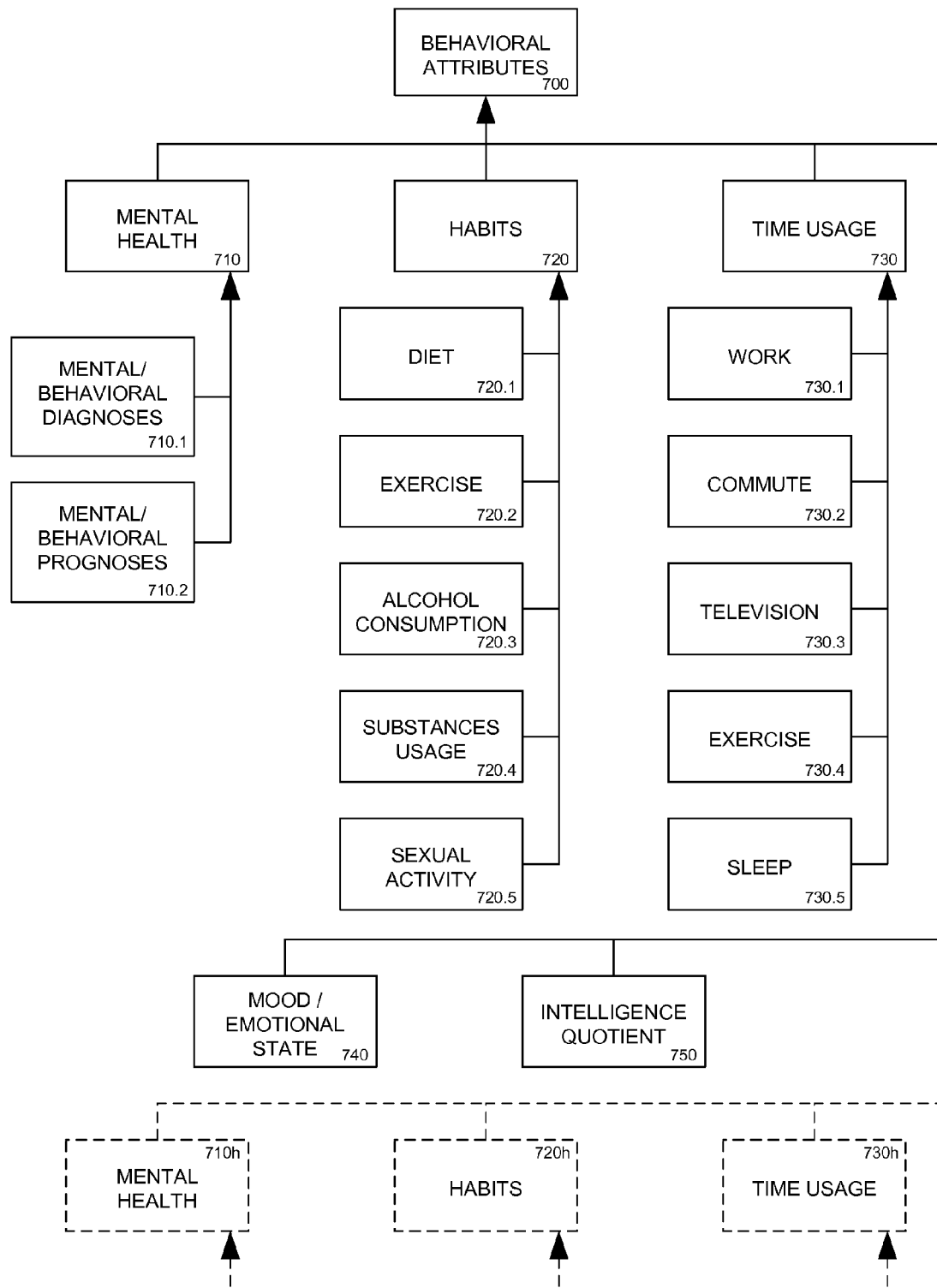
FIG. 7 illustrates representative behavioral attributes classes.

FIG. 7 illustrates classes of behavioral attributes as defined by behavioral attributes metaclass 700, which in one embodiment can include mental health class 710, habits class 720, time usage class 730, mood/emotional state class 740, and intelligence quotient class 750, for example. In one embodiment, mental health class 710 can include mental/behavioral diagnoses subclass 710.1 and mental/behavioral prognoses subclass 710.2; habits class 720 can include diet subclass 720.1, exercise subclass 720.2, alcohol consumption subclass 720.3, substances usage subclass 720.4, and sexual activity subclass 720.5; and time usage class 730 can include work subclass 730.1, commute subclass 730.2, television subclass 730.3, exercise subclass 730.4 and sleep subclass 730.5. Behavioral attributes metaclass 700 can also include historical classes such as historical mental health class 710h, historical habits 720h, and historical time usage class 730h.

As discussed with respect to FIGS. 5 and 6, in one embodiment, external databases such as health care provider databases, purchase records and credit histories, and time tracking systems can be used to supply the data which constitutes the attributes of FIG. 7. Also with respect to FIG. 7, classification systems such as those used by mental health professionals such as classifications found in the DSM-IV can be used directly, such that the attributes of mental health class 710 and historical prior mental health class 710*h* have a direct correspondence to the DSM-IV. The classes and objects of the present invention, as described with respect to FIGS. 5, 6 and 7, can be implemented using a number of database architectures including, but not limited to flat files, relational databases and object oriented databases.

Unified Modeling Language ("UML") can be used to model and/or describe methods and systems and provide the basis for better understanding their functionality and internal operation as well as describing interfaces with external components, systems and people using standardized notation. When used herein, UML diagrams including, but not limited to, use case diagrams, class diagrams and activity diagrams, are meant to serve as an aid in describing the embodiments of the present invention but do not constrain implementation thereof to any particular hardware or software embodiments. Unless otherwise noted, the notation used with respect to the UML diagrams contained herein is consistent with the UML 2.0 specification or variants thereof and is understood by those skilled in the art.

Figure 8:
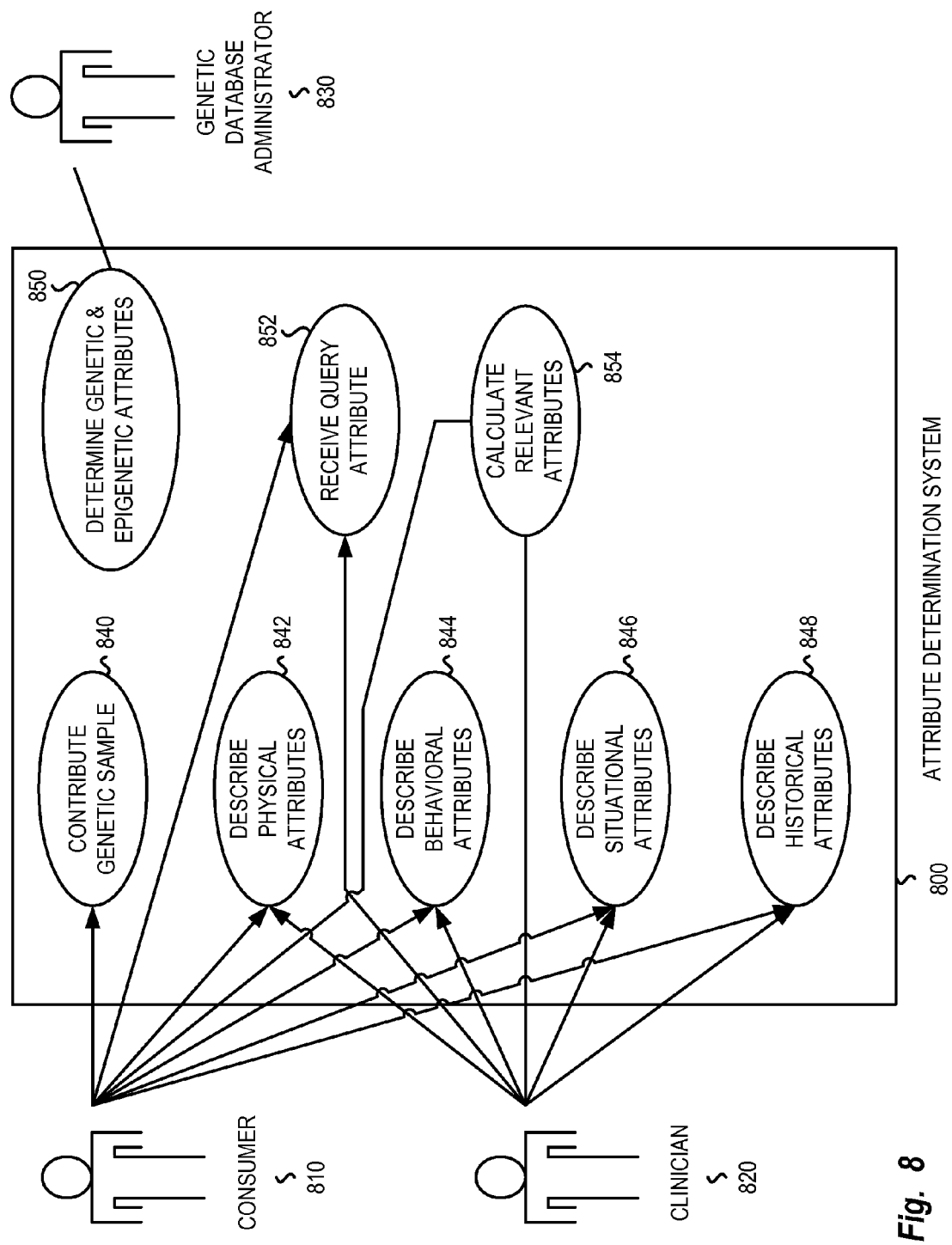
FIG. 8 illustrates an attribute determination system.

FIG. 8 illustrates a use case diagram for an attribute determination system 800 which, in one embodiment, allows for the determination of attributes which are statistically relevant or related to a query attribute. Attribute determination system 800 allows for a consumer 810, clinician 820, and genetic database administrator 830 to interact, although the multiple roles may be filled by a single individual, to input attributes and query the system regarding which attributes are relevant to the specified query attribute. In a contribute genetic sample use case 840 a consumer 810 contributes a genetic sample.

In one embodiment this involves the contribution by consumer 810 of a swab of the inside of the cheek, a blood sample, or contribution of other biological specimen associated with consumer 810 from which genetic and epigenetic data can be obtained. In one embodiment, genetic database administrator 830 causes the genetic sample to be analyzed through a determine genetic and epigenetic attributes use case 850. Consumer 810 or clinician 820 may collect physical attributes through a describe physical attributes use case 842. Similarly, behavioral, situational, and historical attributes are collected from consumer 810 or clinician 820 via describe behavioral attributes use case 844, describe situational attributes use case 846, and describe historical attributes use case 848, respectively. Clinician 820 or consumer 810 can then enter a query attribute through receive query attribute use case 852. Attribute determination system 800 then, based on attributes of large query-attribute-positive and query-attribute-negative populations, determines which attributes and combinations of attributes, extending across the pangenetic (genetic/epigenetic), physical, behavioral, situational, and historical attribute categories, are statistically related to the query attribute. As previously discussed, and with respect to FIG. 1 and FIGS. 4-6, historical attributes can, in certain embodiments, be accounted for through the other categories of attributes. In this embodiment, describe historical attributes use case 848 is effectively accomplished through determine genetic and epigenetic attributes use case 850, describe physical attributes use case 842, describe behavioral attributes use case 844, and describe situational attributes use case 846.

With respect to the aforementioned method of collection, inaccuracies can occur, sometimes due to outright misrepresentations of the individual's habits. For example, it is not uncommon for patients to self-report alcohol consumption levels which are significantly below actual levels. This can occur even when a clinician/physician is involved, as the patient reports consumption levels to the clinician/physician that are significantly below their actual consumption levels. Similarly, it is not uncommon for an individual to over-report the amount of exercise they get.

In one embodiment, disparate sources of data including consumption data as derived from purchase records, data from blood and urine tests, and other observed characteristics are used to derive attributes such as those shown in FIGS. 5-7. By analyzing sets of disparate data, corrections to self-reported data can be made to produce more accurate determinations of relevant attributes. In one embodiment, heuristic rules are used to generate attribute data based on measured, rather than self-reported attributes. Heuristic rules are defined as rules which relate measurable (or accurately measurable) attributes to less measurable or less reliable attributes such as those from self-reported data. For example, an individual's recorded purchases including cigarette purchases can be combined with urine analysis or blood test results which measure nicotine levels or another tobacco related parameter and heuristic rules can be applied to estimate cigarette consumption level. As such, one or more heuristic rules, typically based on research which statistically links a variety of parameters, can be applied by data conversion/formatting engine 220 to the data representing the number of packs of cigarettes purchased by an individual or household, results of urine or blood tests, and other studied attributes, to derive an estimate of the extent to which the individual smokes.

In one embodiment, the heuristic rules take into account attributes such as household size and self-reported data to assist in the derivation of the desired attribute. For example, if purchase data is used in a heuristic rule, household size and even the number of self-reported smokers in the household, can be used to help determine actual levels of consumption of tobacco by the individual. In one embodiment, household members are tracked individually, and the heuristic rules provide for the ability to approximately assign consumption levels to different people in the household. Details such as individual brand usages or preferences may be used to help assign consumptions within the household. As such, in one embodiment the heuristic rules can be applied by data conversion/formatting engine 220 to a number of disparate pieces of data to assist in extracting one or more attributes.

Physical, behavioral, situational and historical attribute data may be stored or processed in a manner that allows retention of maximum resolution and accuracy of the data while also allowing flexible comparison of the data so that important shared similarities between individuals are not overlooked. This can be important when processing narrow and extreme attribute values, or when using smaller populations of individuals where the reduced number of individuals makes the occurrence of identical matches of attributes rare. In these and other circumstances, flexible treatment and comparison of attributes can reveal predisposing attributes that are related to or legitimately derive from the original attribute values but have broader scope, lower resolution, and extended or compounded values compared to the original attributes. In one embodiment, attributes and attribute values can be qualitative (categorical) or quantitative (numerical). In another embodiment, attributes and attribute values can be discrete or continuous numerical values.

There are several ways flexible treatment and comparison of attributes can be accomplished. As shown in FIG. 2, one approach is to incorporate data conversion/formatting engine 220 which is able to create expanded 1st dataset 202 from 1st dataset 200. In one embodiment, 1st dataset 200 can comprise one or more primary attributes, or original attribute profiles containing primary attributes, and expanded 1st dataset 202 can comprise one or more secondary attributes, or expanded attribute profiles containing secondary attributes. A second approach is to incorporate functions into attribute comparison engine 222 that allow it to expand the original attribute data into additional values or ranges during the comparison process. This provides the functional equivalent of reformatting the original dataset without having to create and store the entire set of expanded attribute values.

In one embodiment, original attributes (primary attributes) can be expanded into one or more sets containing derived attributes (secondary attributes) having values, levels or degrees that are above, below, surrounding or including that of the original attributes. In one embodiment, original attributes can be used to derive attributes that are broader or narrower in scope than the original attributes. In one embodiment, two or more original attributes can be used in a computation (i.e., compounded) to derive one or more attributes that are related to the original attributes. As shown in FIG. 9A, a historical situational attribute indicating a time span of smoking, from age 25-27, and a historical behavioral attribute indicating a smoking habit, 10 packs per week, may be compounded to form a single value for the historical situational attribute of total smoking exposure to date, 1560 packs, as shown in FIG. 9B, by simply multiplying 156 weeks by 10 packs/week. Similar calculations enable the derivation of historical situational attributes such as total nicotine and total cigarette tar exposure based on known levels nicotine and tar in the specific brand smoked, Marlboro as indicated by the cigarette brand attribute, multiplied by the total smoking exposure to date. In another example, a continuous numerical attribute, {time=5.213 seconds}, can be expanded to derive the discrete numerical attribute, {time=5 seconds}.

Attribute expansion of a discrete numerical attribute, such as age, can be exemplified in one embodiment using a population comprised of four individuals ages 80, 66, 30 and 15. In this example, Alzheimer's disease is the query attribute, and both the 80 year old and the 66 year old individual have Alzheimer's disease, as indicated by an attribute for a positive Alzheimer's diagnosis in their attribute profiles. Therefore, for this small population, the 80 and 66 year old individuals constitute the query-attribute-positive group (the group associated with the query attribute). If a method of discovering attribute associations is executed, none of the attribute combinations identified as being statistically associated with the query attribute will include age, since the numerical age attributes 80 and 66 are not identical. However, it is already known from empirical scientific research that Alzheimer's disease is an age-associated disease, with prevalence of the disease being much higher in the elderly. By using the original (primary) age attributes to derive new (secondary) age attributes, a method of discovering attribute associations can appropriately identify attribute combinations that contain age as a predisposing attribute for Alzheimer's disease based on the query-attribute-positive group of this population. To accomplish this, a procedure of attribute expansion derives lower resolution secondary age attributes from the primary age attributes and consequently expands the attribute profiles of the individuals in this population. This can be achieved by either categorical expansion or numerical expansion.

In one embodiment of a categorical attribute expansion, primary numerical age attributes are used to derive secondary categorical attributes selected from the following list: infant (ages 0-1), toddler (ages 1-3), child (ages 4-8), preadolescent (ages 9-12), adolescent (ages 13-19), young adult (ages 20-34), mid adult (ages 35-49), late adult (ages 50-64), and senior (ages 65 and up). This particular attribute expansion will derive the attribute 'senior' for the 80 year old individual, 'senior' for the 66 year old, 'young adult' for the 30 year old, and 'adolescent' for the 15 year old. These derived attributes can be added to the respective attribute profiles of these individuals to create an expanded attribute profile for each individual. As a consequence of this attribute expansion procedure, the 80 and 66 year old individuals will both have expanded attribute profiles containing an identical age attribute of 'senior', which will be then be identified in attribute combinations that are statistically associated with the query attribute of Alzheimer's disease, based on a higher frequency of occurrence of this attribute in the query-attribute-positive group for this example.

As an alternative to the above categorical expansion, a numerical attribute expansion can be performed in which numerical age is used to derive a set of secondary numerical attributes comprising a sequence of inequality statements containing progressively larger numerical values than the actual age and a set of secondary attributes comprising a sequence of inequality statements containing progressively smaller quantitative values than the actual age. For example, attribute expansion can produce the following two sets of secondary age attributes for the 80 year old: {110>age, 109>age . . . , 82>age, 81>age} and {age>79, age>78 . . . , age>68, age>67, age>66, age>65, age>64 . . . age>1, age>0}. And attribute expansion can produce the following two sets of secondary age attributes for the 66 year old: {110>age, 109>age . . . , 82>age, 81>age, 80>age, 79>age, 78>age . . . , 68>age, 67>age} and {age>65, age>64 . . . , age>1, age>0}.

Identical matches of age attributes found in the largest attribute combination associated with Alzheimer's disease, based on the 80 and 66 year old individuals that have Alzheimer's in this sample population, would contain both of the following sets of age attributes: {110>age, 109>age . . . , 82>age, 81>age} and {age>65, age>64 . . . , age>1, age>0}. This result indicates that being less than 81 years of age but greater than 65 years of age (i.e., having an age in the range: 81>age>65) is a predisposing attribute for having Alzheimer's disease in this population. This particular method of attribute expansion of age into a numerical sequence of inequality statements provides identical matches between at least some of the age attributes between individuals, and provides an intermediate level of resolution between actual age and the broader categorical age attribute of 'senior' derived in the first example above.

Expansion of age attributes can be also be used for instances in which age is used to designate a point in life at which a specific activity or behavior occurred. For example, FIG. 9 demonstrates an example in which the actual ages of exposure to smoking cigarettes, ages 25-27, are expanded into a low resolution categorical age attribute of 'adult', a broader numerical age range of '21-30', and a set of age attributes comprising a sequence of progressively larger numerical inequality statements for age of the individual, {age>24, age>23 . . . , age>2, age>1}.

Attribute expansion can also be used to reduce the amount of genetic information to be processed by the methods of the present invention, essentially 3 billion nucleotides of information per individual and numerous combinations comprised thereof. For example, attribute expansion can be used to derive a set of lower resolution genetic attributes (e.g., categorical genetic attributes such as names) that can be used instead of the whole genomic sequence in the methods. Categorical genetic attributes can be assigned based on only one or a few specific nucleotide attributes out of hundreds or thousands in a sequence segment (e.g., a gene, or a DNA or RNA sequence read). However, using only lower resolution categorical genetic attributes may cause the same inherent limitations of sensitivity as using only SNPs and genomic markers, which represent only a portion of the full genomic sequence content. So, while categorical genetic attributes can be used to greatly decrease processing times required for execution of the methods, they extract a cost in terms of loss of information when used in place of the full high resolution genomic sequence, and the consequence of this can be the failure to identify certain predisposing genetic variations during execution of the methods. In one embodiment, this can show up statistically in the form of attribute combinations having lower strengths of association with query attributes and/or an inability to identify any attribute combination having an absolute risk of 1.0 for association with a query attribute. So the use of descriptive genetic attributes would be most suitable, and accuracy and sensitivity the methods increased, once the vast majority of influential genetic variations in the genome (both in gene encoding regions and non-coding regions) have been identified and can be incorporated into rules for assigning categorical genetic attributes.

Instead of being appended to the whole genome sequence attribute profile of an individual, categorical genetic attributes can be used to create a separate genetic attribute profile for the individual that comprises thousands of genetic descriptors, rather than billions of nucleotide descriptors. As an example, 19 different nucleotide mutations have been identified in the Cystic Fibrosis Conductance Regulator Gene, each of which can disrupt function of the gene's encoded protein product resulting in clinical diagnosis of cystic fibrosis disease. Since this is the major known disease associated with this gene, the presence of any of the 19 mutations can be the basis for deriving a single lower resolution attribute of 'CFCR gene with cystic fibrosis mutation' with a status value of {1=Yes} to represent possession of the genomic sequence of one of the diseased variations of this gene, with the remaining sequence of the gene ignored. For individuals that do not possess any of the 19 mutations in their copies of the gene, the attribute 'CFCR gene with cystic fibrosis mutation' and a status value {0=No} can be derived. This approach not only reduces the amount of genetic information that needs to be processed, it allows for creation of an identical genetic attribute associated with 19 different individuals, each possessing one of 19 different nucleotide mutations in the Cystic Fibrosis Conductance Regulator Gene, but all having the same gene mutated and sharing the same disease of cystic fibrosis. This allows for identification of identical genetic attribute within their attribute profiles with respect to defect of the CFCR gene without regard for which particular nucleotide mutation is responsible for the defect. This type of attribute expansion can be performed for any genetic sequence, not just gene encoding sequences, and need not be related to disease phenotypes. Further, the genetic attribute descriptors can be names or numeric codes, for example. In one embodiment, a single categorical genetic attribute descriptor can be used to represent a collection of nucleotide variations occurring simultaneously across multiple locations of a genetic sequence or genome.

Similar to expansion of genetic attributes, attribute expansion can be performed with epigenetic attributes. For example, multiple DNA methylation modifications are known to occur simultaneously at different nucleotide positions within DNA segments and can act in a cooperative manner to effect regulation of expression of one gene, or even a collection of genes located at a chromosomal locus. Based on information which indicates that several different patterns of epigenetic DNA methylation, termed epigenetic polymorphisms, can produce the same phenotypic effect, a single categorical epigenetic attribute descriptor can be derived as a descriptor for that group of epigenetic DNA methylation patterns, thereby ensuring the opportunity for an epigenetic attribute match between individuals sharing predisposition to the same outcome but having a different epigenetic polymorphism that produces that outcome. For example, it has been suggested by researchers that several different patterns of epigenetic modification of the HTR2A serotonin gene locus are capable of predisposing an individual to schizophrenia. For individuals associated with one of these particular schizophrenia-predisposing epigenetic patterns, the same categorical epigenetic attribute of 'HTR2A epigenetic schizophrenia pattern' with a status value of {1=yes} can be derived. For an individual who is negative for all known schizophrenia-predisposing epigenetic patterns in the HTR2A gene, the categorical epigenetic attribute of 'HTR2A epigenetic schizophrenia pattern' with a status value {0=no} can be derived to indicate that the individual does not possess any of the epigenetic modifications of the HTR2A serotonin gene locus that are associated with predisposition to schizophrenia.

In one embodiment, the original attribute value is retained and the expanded attribute values provided in addition to allow the opportunity to detect similarities at both the maximal resolution level provided by the original attribute value and the lower level of resolution and/or broader coverage provided by the expanded attribute values or attribute value range. In one embodiment, attribute values are determined from detailed questionnaires which are completed by the consumer/patient directly or with the assistance of clinician 820. Based on these questionnaires, attribute values such as those shown in FIGS. 9A and 9B can be derived. In one or more embodiments, when tabulating, storing, transmitting and reporting results of methods of the present invention, wherein the results include both narrow attributes and broad attributes that encompass those narrow attributes, the broader attributes may be included and the narrow attributes eliminated, filtered or masked in order to reduce the complexity and lengthiness of the final results.

Attribute expansion can be used in a variety of embodiments, many of which are described in the present disclosure, in which statistical associations between attribute combinations and one or more query attributes are determined, identified or used. As such, attribute expansion can be performed to create expanded attribute profiles that are more strongly associated with a query attribute than the attribute profiles from which they were derived. As explained previously, attribute expansion can accomplish this by introducing predisposing attributes that were missing or introducing attributes of the correct resolution for maximizing attribute identities between attribute profiles of a group of query-attribute-positive individuals. In effect, expansion of attribute profiles can reveal predisposing attributes that were previously masked from detection and increase the ability of a method that uses the expanded attribute profiles to predict an individual's risk of association with a query attribute with greater accuracy and certainty as reflected by absolute risk results that approach either 1.0 (certainty of association) or 0.0 (certainty of no association) and have higher statistical significance. To avoid introducing bias error into methods of the present invention, expansion of attribute profiles should be performed according to a set of rules, which can be predetermined, so that identical types of attributes are expanded in the attribute profiles of all individuals processed by the methods. For example, if a method processes the attribute profiles of a group of query-positive individuals and a group of query-attribute-negative individuals, and the query-attribute-positive individuals have had their primary age attributes expanded into secondary categorical age attributes which have been added to their attribute profiles, then attribute expansion of the primary age attributes of the query-attribute-negative individuals should also be performed according to the same rules used for the query-attribute-positive individuals before processing any of the attribute profiles by the method. Ensuring uniform application of attribute expansion across a collection of attribute profiles will minimize introducing considerable bias into those methods that use expanded attribute profiles or data derived from them.

Consistent with the various embodiments of the present invention disclosed herein, computer based systems (which can comprise a plurality of subsystems), datasets, databases and software can be implemented for methods of generating and using secondary attributes and expanded attribute profiles.

In one embodiment, a computer based method for compiling attribute combinations using expanded attribute combinations is provided. A query attribute is received, and a set of expanded attribute profiles associated with a group of query-attribute-positive individuals and a set of expanded attribute profiles associated with a group of query-attribute-negative individuals are accessed, both sets of expanded attribute profiles comprising a set of primary attributes and a set of secondary attributes, wherein the set of secondary attributes is derived from the set of primary attributes and has lower resolution than the set of primary attributes. Attribute combinations having a higher frequency of occurrence in the set of expanded attribute profiles associated with the group of query-attribute-positive individuals than in the set of expanded attribute profiles associated with the group of query-attribute-negative individuals are identified. The identified attribute combinations are stored to create a compilation of attribute combinations that co-occur (i.e., co-associate, co-aggregate) with the query attribute, thereby generating what can be termed an 'attribute combination database'.

In one embodiment, a computer based method for expanding attribute profiles to increase the strength of association between a query attribute and a set of attribute profiles associated with query-attribute-positive individuals is provided. A query attribute is received, and a set of attribute profiles associated with a group of query-attribute-positive individuals and a set of attribute profiles associated with a group of query-attribute-negative individuals are accessed. A first statistical result indicating strength of association of the query attribute with an attribute combination having a higher frequency of occurrence in the set of attribute profiles associated with the group of query-attribute-positive individuals than in the set of attribute profiles associated with the group of query-attribute-negative individuals is determined. One or more attributes in the set of attribute profiles associated with the group of query-attribute-positive individuals and one or more attributes in the set of attribute profiles associated with the query-attribute-negative individuals are expanded to create a set of expanded attribute profiles associated with the group of query-attribute-positive individuals and a set of expanded attribute profiles associated with the group of query-attribute-negative individuals. A second statistical result indicating strength of association of the query attribute with an attribute combination having a higher frequency of occurrence in the set of expanded attribute profiles associated with the group of query-attribute-positive individuals than in the set of expanded attribute profiles associated with the group of query-attribute-negative individuals is determined. If the second statistical result is higher than the first statistical result, the expanded attribute profiles associated with the group of query-attribute-positive individuals and the expanded attribute profiles associated with the group of query-attribute-negative individuals are stored.

In one embodiment, a computer based method for determining attribute associations using an expanded attribute profile is provided. A query attribute is received, and one or more primary attributes in an attribute profile associated with a query-attribute-positive individual are accessed. One or more secondary attributes are the derived from the primary attributes such that the secondary attributes are lower resolution attributes than the primary attributes. The secondary attributes are stored in association with the attribute profile to create an expanded attribute profile. Attribute combinations that are associated with the query attribute are determined by identifying attribute combinations from the expanded attribute profile that have higher frequencies of occurrence in a set of attribute profiles associated with a group of query-attribute-positive individuals than in a set of attribute profiles associated with a group of query-attribute-negative individuals.

In one embodiment, a computer based method for determining attribute associations using an expanded attribute profile is provided in which one or more primary attributes in an attribute profile are accessed. One or more secondary attributes are generated from the primary attributes such that the secondary attributes have lower resolution than the primary attributes. The secondary attributes are stored in association with the attribute profile to create an expanded attribute profile. The strength of association between the expanded attribute profile and a query attribute is determined by comparing the expanded attribute profile to a set of attribute combinations that are statistically associated with the query attribute.

The methods, systems, software and databases disclosed herein are able to achieve determination of complex combinations of predisposing attributes not only as a consequence of the resolution and breadth of data used, but also as a consequence of the process methodology used for discovery of predisposing attributes. An attribute may have no effect on expression of another attribute unless it occurs in the proper context, the proper context being co-occurrence with one or more additional predisposing attributes. In combination with one or more additional attributes of the right type and degree, an attribute may be a significant contributor to predisposition of the organism for developing the attribute of interest. This contribution is likely to remain undetected if attributes are evaluated individually. As an example, complex diseases require a specific combination of multiple attributes to promote expression of the disease. The required disease-predisposing attribute combinations will occur in a significant percentage of those that have or develop the disease and will occur at a lower frequency in a group of unaffected individuals.

FIG. 10 illustrates an example of the difference in frequencies of occurrence of attributes when considered in combination as opposed to individually. In the example illustrated, there are two groups of individuals referred to based on their status of association with a query attribute (a specific attribute of interest that can be submitted in a query). One group does not possess (is not associated with) the query attribute, the query-attribute-negative group, and the other does possess (is associated with) the query attribute, the query-attribute-positive group. In one embodiment, the query attribute of interest is a particular disease or trait. The two groups are analyzed for the occurrence of two attributes, A and X, which are candidates for causing predisposition to the disease. When frequencies of occurrence are computed individually for A and for X, the observed frequencies are identical (50%) for both groups. When the frequency of occurrence is computed for the combination of A with X for individuals of each group, the frequency of occurrence is dramatically higher in the positive group compared to the negative group (50% versus 0%). Therefore, while both A and X are significant contributors to predisposition in this theoretical example, their association with expression of the disease in individuals can only be detected by determining the frequency of co-occurrence of A with X in each individual.

FIG. 11 illustrates another example of the difference in frequencies of occurrence of attributes when considered in combination as opposed to individually. In this example there are again two groups of individuals that are positive or negative for an attribute of interest submitted in a query, which could again be a particular disease or trait of interest. Three genes are under consideration as candidates for causing predisposition to the query attribute. Each of the three genes has three possible alleles (each labeled A, B, or C for each gene). This example not only illustrates the requirement for attributes occurring in combination to cause predisposition, but also the phenomenon that there can be multiple different combinations of attributes that produce the same outcome. In the example, a combination of either all A, all B, or all C alleles for the genes can result in predisposition to the query attribute. The query-attribute-positive group is evenly divided among these three attribute combinations, each having a frequency of occurrence of 33%. The same three combinations occur with 0% frequency in the query-attribute-negative group. However, if the attributes are evaluated individually, the frequency of occurrence of each allele of each gene is an identical 33% in both groups, which would appear to indicate no contribution to predisposition by any of the alleles in one groups versus the other. As can be seen from FIG. 11, this is not the case, since every gene allele considered in this example does contribute to predisposition toward the query attribute when occurring in a particular combination of alleles, specifically a combination of all A, all B, or all C. This demonstrates that a method of attribute predisposition determination needs to be able to detect attributes that express their predisposing effect only when occurring in particular combinations. It also demonstrates that the method should be able to detect multiple different combinations of attributes that may all cause predisposition to the same query attribute.

Although the previous two figures present frequencies of occurrence as percentages, for the methods of the present invention the frequencies of occurrence of attribute combinations are can be stored as ratios for both the query-attribute-positive individuals and the query-attribute-negative individuals. Referring to FIG. 12A and FIG. 12B, the frequency of occurrence for the query-attribute-positive group is the ratio of the number of individuals of that group having the attribute combination (the exposed query-attribute-positive individuals designated 'a') to the total number of individuals in that group ('a' plus 'c'). The number of individuals in the query-attribute-positive group that do not possess the attribute combination (the unexposed query-attribute-positive individuals designated 'c') can either be tallied and stored during comparison of attribute combinations, or computed afterward from the stored frequency as the total number of individuals in the group minus the number of exposed individuals in that group (i.e., (a+c)−a=c). For the same attribute combination, the frequency of occurrence for the query-attribute-negative group is the ratio of the number of individuals of that group having the attribute combination (the exposed query-attribute-negative individuals designated 'b') to the total number of individuals in that group ('b' plus 'd').

The number of individuals in the query-attribute-negative group that do not possess the attribute combination (the unexposed query-attribute-negative individuals designated 'd') can either be tallied and stored during comparison of attribute combinations or can be computed afterward from the stored frequency as the total number of individuals in the group minus the number of exposed individuals in that group (i.e., (b+d)−b=d).

The frequencies of occurrence of an attribute or attribute combination, when compared for two or more groups of individuals with respect to a query attribute, are statistical results (values) that can indicate strength of association of the attribute combination with a query attribute and can therefore be referred to as corresponding statistical results in one or more embodiments of the present invention. Frequencies of occurrence can also be utilized by statistical computation engine 224 to compute additional statistical results for strength of association (i.e., strength of association values) of the attribute combinations with the query attribute, and these statistical results may also be referred to as corresponding statistical results in one or more embodiments. The statistical measures used to compute these statistical results may include, but are not limited to, prevalence, incidence, probability, absolute risk, relative risk, attributable risk, excess risk, odds (a.k.a. likelihood), and odds ratio (a.k.a. likelihood ratio). Absolute risk (a.k.a. probability), relative risk, odds, and odds ratio are the preferred statistical computations for the present invention. Among these, absolute risk and relative risk are the more preferable statistical computations because their values can still be calculated for an attribute combination in instances where the frequency of occurrence of the attribute combination in the query-attribute-negative group is zero. Odds and odds ratio are undefined in instances where the frequency of occurrence of the attribute combination in the query-attribute-negative group is zero, because in that situation their computation requires division by zero which is mathematically undefined. One embodiment of the present invention, when supplied with ample data, is expected to routinely yield frequencies of occurrence of zero in query-attribute-negative groups because of its ability to discover large predisposing attribute combinations that are exclusively associated with the query attribute.

FIG. 12B illustrates formulas for the statistical measures that can be used to compute statistical results. In one embodiment absolute risk is computed as the probability that an individual has or will develop the query attribute, given exposure to an attribute combination. In one embodiment, relative risk is computed as the ratio of the probability that an exposed individual has or will develop the query attribute to the probability that an unexposed individual has or will develop the query attribute. In one embodiment, odds is computed as the ratio of the probability that an exposed individual has or will develop the query attribute (absolute risk of the exposed query-attribute-positive individuals) to the probability that an exposed individual does not have and will not develop the query attribute (absolute risk of the exposed query-attribute-negative individuals). In one embodiment, the odds ratio is computed as the ratio of the odds that an exposed individual has or will develop the query attribute to the odds that an unexposed individual has or will develop the query attribute.

In one embodiment, results for absolute risk and relative risk can be interpreted as follows with respect to an attribute combination predicting association with a query attribute: 1) if absolute risk=1.0, and relative risk is mathematically undefined, then the attribute combination is sufficient and necessary to cause association with the query attribute, 2) if absolute risk=1.0, and relative risk is not mathematically undefined, then the attribute combination is sufficient but not necessary to cause association with the query attribute, 3) if absolute risk <1.0, and relative risk is not mathematically undefined, then the attribute combination is neither sufficient nor necessary to cause association with the query attribute, and 4) if absolute risk <1.0, and relative risk is mathematically undefined, then the attribute combination is not sufficient but is necessary to cause association with the query attribute. In an alternate embodiment, a relative risk that is mathematically undefined can be interpreted to mean that there are two or more attribute combinations, rather than just one attribute combination, that can cause association with the query attribute. In one embodiment, an absolute risk <1.0 can be interpreted to mean one or more of the following: 1) the association status of one or more attributes, as provided to the methods, is inaccurate or missing (null), 2) not enough attributes have been collected, provided to or processed by the methods, or 3) the resolution afforded by the attributes that have been provided is too narrow or too broad. These interpretations can be used to increase accuracy and utility of the methods for use in many applications including but not limited to attribute combination discovery, attribute prediction, predisposition prediction, predisposition modification and destiny modification.

The statistical results obtained from computing the statistical measures, as well as the attribute combinations to which they correspond, can be subjected to inclusion, elimination, filtering, and evaluation based on meeting one or more statistical requirements which may be predetermined, predesignated, preselected or alternatively, computed de novo based on the statistical results. Statistical requirements can include, but are not limited to, numerical thresholds, statistical minimum or maximum values, and statistical significance (confidence) values which may collectively be referred to as predetermined statistical thresholds. Ranks (e.g., numerical rankings) assigned to attribute combinations based on their attribute content and/or the corresponding statistical results can likewise be subjected to inclusion, elimination, filtering, and evaluation based on a predetermined threshold, in this case applied to rank, which can be specified by a user or by the computer system implementing the methods.

One embodiment of the present invention can be used in many types of statistical analyses including but not limited to Bayesian analyses (e.g., Bayesian probabilities, Bayesian classifiers, Bayesian classification tree analyses, Bayesian networks), linear regression analyses, non-linear regression analyses, multiple linear regression analyses, uniform analyses, Gaussian analyses, hierarchical analyses, recursive partitioning (e.g., classification and regression trees), resampling methods (e.g., bootstrapping, cross-validation, jackknife), Markov methods (e.g., Hidden Markov Models, Regular Markov Models, Markov Blanket algorithms), kernel methods (e.g., Support Vector Machine, Fisher's linear discriminant analysis, principle components analysis, canonical correlation analysis, ridge regression, spectral clustering, matching pursuit, partial least squares), multivariate data analyses including cluster analyses, discriminant analyses and factor analyses, parametric statistical methods (e.g., ANOVA), non-parametric inferential statistical methods (i.e., binomial test, Anderson-Darling test, chi-square test, Cochran's Q, Cohen's kappa, Efron-Petrosian Test, Fisher's exact test, Friedman two-way analysis of variance by ranks, Kendall's tau, Kendall's W, Kolmogorov-Smirnov test, Kruskal-Wallis one-way analysis of variance by ranks, Kuiper's test, Mann-Whitney U or Wilcoxon rank sum test, McNemar's test, median test, Pitman's permutation test, Siegel-Tukey test, Spearman's rank correlation coefficient, Student-Newman-Keuls test, Wald-Wolfowitz runs test, Wilcoxon signed-rank test).

In one embodiment, the methods, databases, software and systems of the present invention can be used to produce data for use in and/or results for the above statistical analyses. In another embodiment, the methods, databases, software and systems of the present invention can be used to independently verify the results produced by the above statistical analyses.

In one embodiment a method is provided which accesses a first dataset containing attributes associated with a set of query-attribute-positive individuals and query-attribute-negative individuals, the attributes being pangenetic, physical, behavioral and situational attributes associated with individuals, and creates a second dataset of attributes associated with a query-attribute-positive individual but not associated with one or more query-attribute-negative individuals. A third dataset can be created which contains combinations of attributes from the second dataset (i.e., attribute combinations) that are either associated with one or more query-attribute-positive individuals or are not present in any of the query-attribute-negative individuals, along with the frequency of occurrence in the query-attribute-positive individuals and the frequency of occurrence in the query-attribute-negative individuals. Statistical computations based on the frequencies of occurrence can be performed for each attribute combination, where the statistical computation results indicate the strength of association, as measured by one or more well known statistical measures, between each attribute combination and the query attribute. The process can be repeated for a number of query attributes, and multiple query-positive individuals can be studied to create a computer-stored and machine-accessible compilation of different attribute combinations that co-occur with the queried attributes. The compilation can be ranked (i.e., attribute combinations can be assigned individual ranks) and co-occurring attribute combinations not meeting a statistical requirement for strength of association with the query attribute and/or at least a minimum rank can be eliminated from the compilation. The statistical requirement can be a minimum or maximum statistical value and/or a value of statistical significance applied to one or more statistical results. In a further embodiment, ranking the attribute combinations can also be based on the attribute content of the attribute combinations, such as whether certain attributes are present or absent in a particular attribute combination, what percentage of attributes in a particular attribute combination are modifiable, what specific modifiable attributes are present in a particular attribute combination, and/or what types or categories of attributes (i.e., epigenetic, genetic, physical, behavioral, situational) are present in a particular attribute and in what relative percentages. These methods of ranking attribute combinations can be applied in various embodiments of the present invention disclosed herein.

Similarly, a system can be developed which contains a subsystem for accessing a query attribute, a second subsystem for accessing a set of databases containing pangenetic, physical, behavioral, and situational attributes associated with a plurality of query-attribute-positive, and query-attribute-negative individuals, a data processing subsystem for identifying combinations of pangenetic, physical, behavioral, and situational attributes associated with query-attribute-positive individuals, but not with query-attribute-negative individuals, and a calculating subsystem for determining a set of statistical results that indicates a strength of association between the combinations of pangenetic, physical, behavioral, and situational attributes with the query attribute. The system can also include a communications subsystem for retrieving at least some of pangenetic, physical, behavioral, and situational attributes from at least one external database; a ranking subsystem for ranking the co-occurring attributes according to the strength of the association of each co-occurring attribute with the query attribute; and a storage subsystem for storing the set of statistical results indicating the strength of association between the combinations of pangenetic, physical, behavioral, and situational attributes and the query attribute. The various subsystems can be discrete components, configurations of electronic circuits within other circuits, software modules running on computing platforms including classes of objects and object code, or individual commands or lines of code working in conjunction with one or more Central Processing Units (CPUs). A variety of storage units can be used including but not limited to electronic, magnetic, electromagnetic, optical, opto-magnetic and electro-optical storage.

In one application the method and/or system is used in conjunction with a plurality of databases, such as those that would be maintained by health-insurance providers, employers, or health-care providers, which serve to store the aforementioned attributes. In one embodiment the pangenetic (genetic and epigenetic) data is stored separately from the other attribute data and is accessed by the system/method. In another embodiment the pangenetic data is stored with the other attribute data. A user, such as a clinician, physician or patient, can input a query attribute, and that query attribute can form the basis for determination of the attribute combinations associated with that query attribute. In one embodiment the associations will have been previously stored and are retrieved and displayed to the user, with the highest ranked (most strongly associated) combinations appearing first. In an alternate embodiment the calculation is made at the time the query is entered, and a threshold can be used to determine the number of attribute combinations that are to be displayed.

Figure 13:
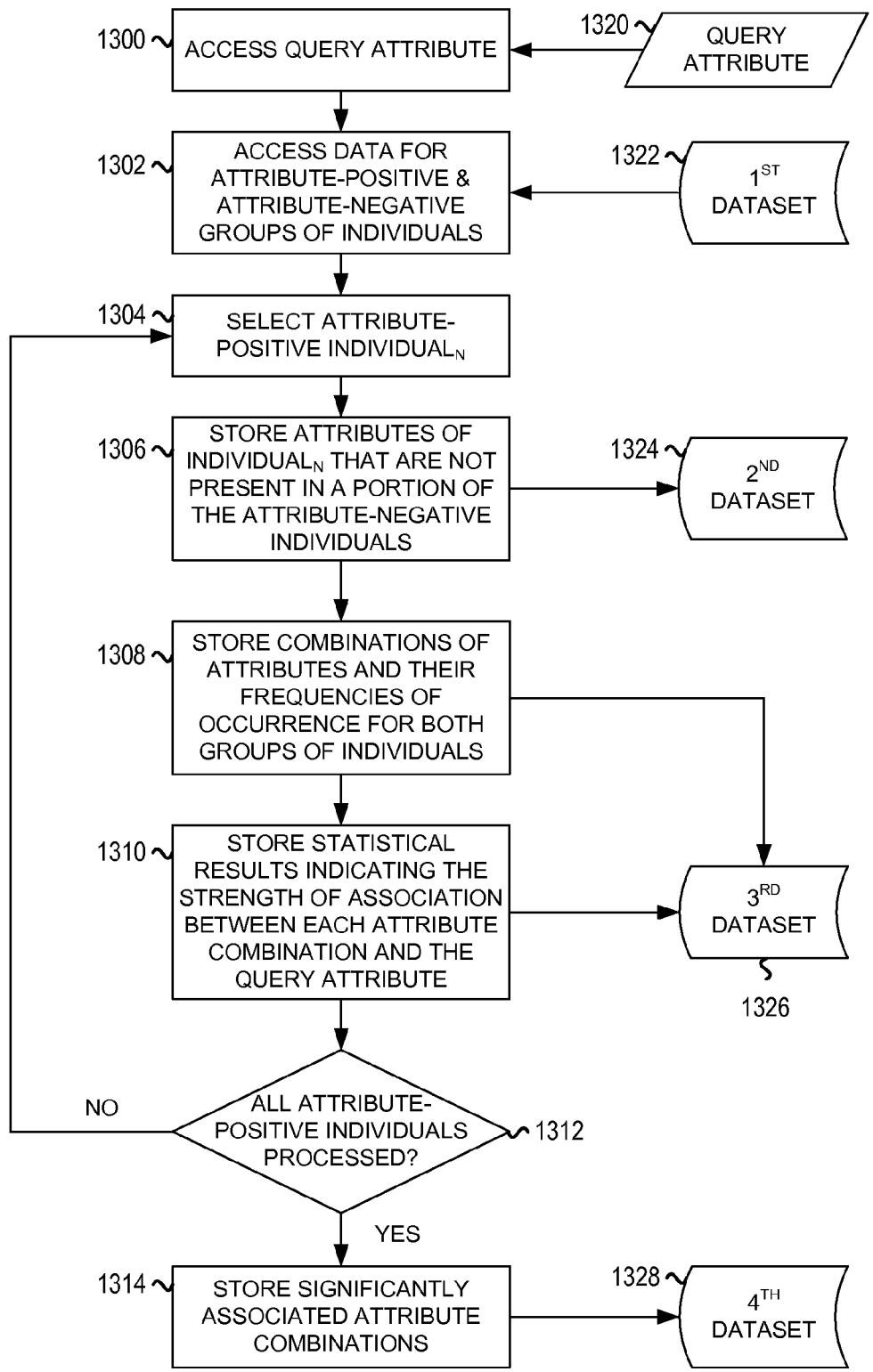
FIG. 13 illustrates a flow chart for a method of creating an attribute combinations database.

FIG. 13 illustrates a flowchart of one embodiment of a method for creation of a database of attribute combinations, wherein 1st dataset 1322, 2nd dataset 1324, 3rd dataset 1326 and 4th dataset 1328 correspond to 1st dataset 200, 2nd dataset 204, 3rd dataset 206 and 4th dataset 208 respectively of the system illustrated in FIG. 2. Expanded 1st dataset 202 of FIG. 2 is optional for this embodiment of the method and is therefore not illustrated in the flowchart of FIG. 13. One aspect of this method is the comparison of attributes and attribute combinations of different individuals in order to identify those attributes and attribute combinations that are shared in common between those individuals. Any attribute that is present in the dataset record of an individual is said to be associated with that individual.

1st dataset 1322 in the flow chart of FIG. 13 represents the initial dataset containing the individuals' attribute dataset records to be processed by the method. FIG. 14 illustrates an example of the content of a 1st dataset representing attribute data for 111 individuals. Each individual's association with attributes A-Z is indicated by either an association status value of 0 (no, does do not possess the attribute) or a status value of 1 (yes, does possess the attribute). In one embodiment, this is preferred format for indicating the presence or absence of association of an attribute with an individual. In an alternate embodiment, an individual's attribute profile or dataset record contains the complete set of attributes under consideration and a 0 or 1 status value for each. In other embodiments, representation of association of an attribute with an individual can be more complex than the simple binary value representations of yes or no, or numerical 1 or 0. In one embodiment, the presence of attributes themselves, for example the actual identity of nucleotides, a brand name, or a trait represented by a verbal descriptor, can be used to represent the identity, degree and presence of association of the attribute. In one embodiment, the absence of an attribute is itself an attribute that can be referred to and/or represented as a 'not-attribute'. In one embodiment, a not-attribute simply refers to an attribute having a status value of 0, and in a further embodiment, the not-attribute is determined to be associated with an individual or present in an attribute profile (i.e., dataset, database or record) if the corresponding attribute has a status value of 0 associated with the individual or is present in the attribute profile as an attribute with a status value of 0, respectively. In another embodiment, a not-attribute can be an attribute descriptor having a 'not' prefix, minus sign, or alternative designation imparting essentially the same meaning. In a further embodiment, not-attributes are treated and processed no differently than other attributes. In circumstances where data for an attribute or an attribute's association status cannot be obtained for an individual, the attribute or attribute status may be omitted and represented as a null. Typically, a null should not be treated as being equivalent to a value of zero, since a null is not a value. A null represents the absence of a value, such as when no attribute or attribute association status is entered into a dataset for a particular attribute.

In the example illustrated in FIG. 14, individuals #1-10 and #111 possess unique attribute content which is not repeated in other individuals of this population. Individuals #11-20 are representative of individuals #21-100, so that the data for each of the individuals #11-20 is treated as occurring ten times in this population of 111 individuals. In other words, there are nine other individuals within the group of individuals #21-100 (not shown in the table) that have A-Z attribute values identical to those of individual #11. The same is true for individuals #12, #13, #14, #15, #16, #17, #18, #19 and #20.

As shown in the flowchart of FIG. 13, in one embodiment the method begins with access query attribute step 1300 in which query attribute 1320, provided either by a user or by automated submission, is accessed. For this example the query attribute is 'A'. In access data for attribute-positive and attribute-negative groups of individuals step 1302, the attribute data for attribute-positive (i.e., query-attribute-positive) and attribute-negative (i.e., query-attribute-negative) individuals as stored in 1st dataset 1322 are accessed. The differentiation of the two groups of individuals is based upon query attribute 1320 which determines the classification of the individuals as either query-attribute-positive individuals (those individuals that possess the query attribute in their 1st dataset record) or query-attribute-negative individuals (those individuals that do not possess the query attribute in their dataset record). For query attribute 'A', individuals #1-10 are the query-attribute-positive individuals, and individuals #11-111 are the query-attribute-negative individuals.

In select attribute-positive individual, step 1304, individual #1 is selected in this example for comparison of their attributes with those of other individuals. In store attributes of individual$_N$ that are not present in a portion of the attribute-negative individuals step 1306, those attributes of the selected individual #1 that are not associated with a portion (e.g., one or more; a fraction having a specified value; a percentage such as 0.1%, 1%, 5%, 10%, 15%, 20%, or 25%, or more; or a continuous non-integer value resulting from, for example, a statistical computation) of the query-attribute-negative group of individuals, or a randomly selected subgroup of the query-attribute-negative group of individuals, are stored in 2nd dataset 1324 as potential candidate attributes for contributing to predisposition toward the query attribute. In one embodiment this initial comparison step is used to increase efficiency of the method by eliminating those attributes that are associated with all of the query-attribute-negative individuals. Because such attributes occur with a frequency of 100% in the query-attribute-negative group, they cannot occur at a higher frequency in the query-attribute-positive group and are therefore not candidates for contributing to predisposition toward the query attribute. Therefore, this step ensures that only attributes of the individual that occur with a frequency of less than 100% in the query-attribute-negative group are stored in the 2nd dataset. This step is especially useful for handling genetic attributes since the majority of the approximately three billion nucleotide attributes of the human genome are identically shared among individuals and may be eliminated from further comparison before advancing to subsequent steps.

As mentioned above, this initial comparison to effectively eliminate attributes that are not potential candidates may be performed against a randomly selected subgroup of query-attribute-negative individuals. Using a small subgroup of individuals for the comparison increases efficiency and prevents the need to perform a comparison against the entire query-attribute-negative population which may consist of thousands or even millions of individuals. In one embodiment, such a subgroup preferably consists of at least 20, but as few as 10, randomly selected query-attribute-negative individuals.

For the present example, only those attributes having a status value of 1 for individual #1 and a status value of 0 for one or more query-attribute-negative individuals are stored as potential candidate attributes, but in one embodiment those attributes having a status value of 0 for individual #1 and a status value of 1 for one or more query-attribute-negative individuals (i.e., attributes I, K, Q and W) can also be stored as candidate attributes, and may be referred to as candidate not-attributes of individual #1. FIG. 15A illustrates the 2nd dataset which results from processing the attributes of individual #1 for query attribute 'A' in a comparison against individuals #11-111 of the query-attribute-negative subgroup. The stored candidate attributes consist of C, E, F, N, T and Y. FIG. 15B illustrates a tabulation of all possible combinations of these attributes. In store combinations of attributes and their frequencies of occurrence for both groups of individuals step 1308, those combinations of attributes of 2nd dataset 1324 that are found by comparison to be associated with one or more query-attribute-positive individuals of 1st dataset 1322 are stored in 3rd dataset 1326 along with the corresponding frequencies of occurrence for both groups determined during the comparison. Although not relevant to this example, there may be instances in which a particular attribute combination is rare enough, or the group sizes small enough, that the selected query-attribute-positive individual is the only individual that possesses that particular attribute combination. Under such circumstances, no other individual of the query-attribute-positive group and no individual of the query-attribute-negative group will be found to possess that particular attribute combination. To ensure that the attribute combination is stored as a potential predisposing attribute combination, one embodiment of the method can include a requirement that any attribute combination not present in any of the query-attribute-negative individuals be stored in the 3rd dataset along with the frequencies of occurrence for both groups. Any attribute combination stored according to this rule necessarily has a frequency of occurrence equal to zero for the query-attribute-negative group and a frequency of occurrence having a numerator equal to one for the attribute-positive group.

FIG. 16 illustrates a 3rd dataset containing a representative portion of the stored attribute combinations and their frequencies of occurrence for the data of this example. Each frequency of occurrence is preferably stored as a ratio of the number of individuals of a group that are associated with the attribute combination in the numerator and the total number of individuals of that group in the denominator.

In store statistical results indicating the strength of association between each attribute combination and the query attribute step 1310, the frequencies of occurrence previously stored in 3rd dataset 1326 are used to compute statistical results for the attribute combinations which indicate the strength of association of each attribute combination with the query attribute. As mentioned previously, the statistical computations used may include prevalence, incidence, absolute risk (a.k.a. probability), attributable risk, excess risk, relative risk, odds and odds ratio. In one embodiment, absolute risk, relative risk, odds and odds ratio are the statistical computations performed (see formulas in FIG. 12B). Computed statistical results stored with their corresponding attribute combinations are shown in the 3rd dataset illustrated by FIG. 16. The odds and odds ratio computations for the attribute combinations CEFNTY, CEFNT, CEFNY, CFNTY and CEFN are shown as undefined in this 3rd dataset example because the frequencies of occurrence of these attribute combinations in the query-attribute-positive group are zero.

For the sake of brevity, only the individual #1 was selected and processed in the method, thereby determining only the predisposing attribute combinations of individual #1 and those individuals of the group that also happen to possess one or more of those attribute combinations. However, one can proceed to exhaustively determine all predisposing attribute combinations in the query-attribute-positive group and build a complete 3rd dataset for the population with respect to query attribute 'A'. As shown in the flow chart of FIG. 13, this is achieved by simply including all attribute-positive individuals processed? step 1312 to provide a choice of selecting successive individuals from the query-attribute-positive group and processing their attribute data through successive iteration of steps 1300-1310 one individual at a time until all have been processed. The selection of successive individuals may include the selection of every individual in the query-attribute-positive group, or alternatively, may be restricted to a randomly or non-randomly selected representative subset of individuals from the query-attribute-positive group of individuals. The resulting data for each additional individual is simply appended into the 3rd dataset during each successive iteration. When selecting and processing multiple individuals, data in the 2nd dataset is preferably deleted between iterations, or uniquely identified for each individual. This will ensure that any data in the 2nd dataset originating from a previous iteration is not reconsidered in current and subsequent iterations of other individuals in the group. Alternate techniques to prevent reconsideration of the data can be utilized.

In store significantly associated attribute combinations step 1314, 4th dataset 1328 may be created by selecting and storing only those attribute combinations and their associated data from the 3rd dataset having a minimum statistical association with the query attribute. The minimum statistical association can be a positive, negative or neutral association, or combination thereof, as determined by the user or the system. This determination can be made based on the statistical results previously stored in 3rd dataset 1326. As an example, the determination can be made based on the results computed for relative risk. Statistically, a relative risk of >1.0 indicates a positive association between the attribute combination and the query attribute, while a relative risk of 1.0 indicates no association, and a relative risk of <1.0 indicates a negative association.

FIG. 17 illustrates a 4th dataset consisting of attribute combinations with a relative risk >1.0, from which the attribute combinations CETY and CE are excluded because they have associated relative risks < or =1.0. FIG. 18 illustrates another example of a 4th dataset that can be created. In this example, a minimum statistical association requirement of either relative risk >4.0 or absolute risk >0.3 produce this 4th dataset.

It can be left up to the user or made dependent on the particular application as to which statistical measure and what degree of statistical association is used as the criteria for determining inclusion of attribute combinations in the 4th dataset. In this way, 4th dataset 1328 can be presented in the form of a report which contains only those attribute combinations determined to be predisposing toward the query attribute above a selected threshold of significant association for the individual or population of individuals.

In many applications it will be desirable to determine predisposing attribute combinations for additional query attributes within the same population of individuals. In one embodiment this is accomplished by repeating the entire method for each additional query attribute and either creating new 2nd, 3rd and 4th datasets, or appending the results into the existing datasets with associated identifiers that clearly indicate what data results correspond to which query attributes. In this way, a comprehensive database containing datasets of predisposing attribute combinations for many different query attributes may be created.

In one embodiment of a method for creating an attribute combinations database, attribute profile records of individuals that have nulls for one or more attribute values are not processed by the method or are eliminated from the 1st dataset before initiating the method. In another embodiment, attribute profile records of individuals that have nulls for one or more attribute values are only processed by the method if those attribute values that are nulls are deemed inconsequential for the particular query or application. In another embodiment, a population of individuals having one or more individual attribute profile records containing nulls for one or more attribute values are only processed for those attributes that have values (non-nulls) for every individual of that population.

In one embodiment of a method for creating an attribute combinations database, frequencies of occurrence and statistical results for strength of association of existing attribute combinations in the attribute combinations dataset are updated based on the attribute profile of an individual processed by the method. In another embodiment, frequencies of occurrence and statistical results for strength of association of existing attribute combinations in the attribute combinations dataset are not updated based on the attribute profile of an individual processed by the method. In another embodiment, the processing of an individual by the method can require first comparing the individuals' attribute profile to the preexisting attribute combinations dataset to determine which attribute combinations in the dataset are also present in the individual's attribute profile, and then in a further embodiment, based on the individual's attribute profile, updating the frequencies of occurrence and statistical results for strength of association of those attribute combinations in the dataset that are also present in the individual's attribute profile, without further processing the individual or their attributes by the method.

The 3rd and 4th datasets created by performing the above methods for creation of a database of attribute combinations can be used for additional methods of the invention that enable: 1) identification of predisposing attribute combinations toward a key attribute of interest, 2) predisposition prediction for an individual toward a key attribute of interest, and 3) destiny modification provided as predisposition predictions resulting from the addition or elimination of specific attribute associations.

A method for compiling an attribute combination database that requires determining all possible combinations of attributes that can be formed from an attribute profile, and then computing the strength of association of each of those attribute combinations with the query attribute, can present a considerable computational challenge. For example, forming all possible subcombinations of 50 attributes from an attribute profile comprising just 100 attributes requires a minimum of $1 \times 10^{29}$ operations (i.e., 100 choose 50=$1 \times 10^{29}$), which would be expected to take $3.2 \times 10^6$ years of computing time on a 1 petaFLOPS supercomputer. One method for streamlining the identification of attribute combinations that co-associate with a query attribute is to compare attribute profiles with one another and only evaluate those attribute combinations which constitute the intersection in attribute content (i.e., shared attribute combinations) between the attribute profiles. This approach eliminates the computational expense of forming attribute combinations that are unique to only a single attribute profile.

One approach to determining co-associating attributes requires determining the intersection of attributes for every possible combination of attribute profiles that can be formed from a set of attribute profiles. Briefly, this method requires forming all possible 2-tuple combinations of attribute profiles from the set of attribute profiles and comparing the attribute profiles within each 2-tuple. The largest combination of attributes that occurs within both attribute profiles of each 2-tuple is identified and stored as the largest attribute combination co-occurring in that 2-tuple. Next, all possible 3-tuple combinations of the attribute profiles are formed. For each 3-tuple, the largest attribute combination that occurs within all three attribute profiles of that 3-tuple combination is identified and stored as the largest attribute combination co-occurring in that 3-tuple. Next 4-tuples are formed and the largest co-occurring attribute combination within each 4-tuple identified. This approach is repeated for progressively larger tuples by simply increasing the n-tuple size by one at each step. Computational burden can be reduced in part by incorporating a requirement that prevents the formation of any (n+1)-tuple combination from an n-tuple combination for which no co-occurring attribute combination was identified. With this requirement, identification of attribute combinations is completed at the point at which every n-tuple combination generated at a particular step is null for a co-occurring attribute combination (i.e., not a single one of the newly generated n-tuple combinations contains attribute profiles having at least one shared attribute combination in common).

The shortcomings of the immediately previous method are two-fold. The first shortcoming relates to the very large number of attribute comparisons that may be required in the initial step alone. For example, when comparing 1,000 genetic attribute profiles comprising 1 million SNPs per attribute profile, $5 \times 10^{11}$ individual attribute comparisons are required just for the initial step of comparing all possible pairs of the 1,000 genetic attribute profiles (($5 \times 10^5$ possible pairings of attribute profiles)$\times$($10^6$ attributes per attribute profile)=$5 \times 10^{11}$ individual attribute comparisons). If each attribute profile contained the full complement of 3 billion nucleotides of whole genomic sequence, then $1.5 \times 10^{15}$ individual attribute comparisons would be required in the first step of comparing all possible pairs of attribute profiles, resulting in a computationally intensive method requiring a supercomputer. The second shortcoming of this particular method is that it only identifies the largest attribute combination that is shared within each n-tuple combination of attribute profiles. The method does not enable identification of smaller attribute combinations, contained within each largest identified attribute combination, which may be responsible for the bulk of the strength of association of the larger attribute combinations with the query attribute. A smaller attribute combination would not be identified by this particular method unless there is at least one individual that possesses only that smaller attribute combination without having any of the other attributes present in the larger attribute combination. To exemplify this deficiency, consider a query-attribute-positive group consisting of genetically identical individuals (i.e., identical siblings or clones) all having blue eyes, for which the submitted query attribute is blue eyes. Applying the above method to process the genetic attribute profiles of these query-attribute-positive individuals would yield an attribute combination potentially containing their entire genomic sequence, since that is the largest attribute combination shared in common between these genetically identical individuals. Such a large combination of attributes yields little or no useful information about which particular attributes directly predispose an individual to having blue eye color. Although this is an extreme example, it clearly demonstrates a deficiency of this approach. The above shortcomings limit the usefulness of this approach for determining attribute combinations associated with a query attribute and make it a nonpreferred method.

It is desirable that a method for compiling co-associating attributes identify not only the largest attribute combinations shared by attribute profiles, but also smaller attribute combinations as well, to determine the smallest and most strongly associated core attribute combinations that co-associate with a particular query attribute. A core attribute combination can, for example, be defined as the smallest subset of attributes having a statistically significant association with the query attribute. An alternative definition of a core attribute combination can be the smallest subset of attributes that confers an absolute risk of association with the query attribute above a predetermined threshold. Other definitions of a core attribute combination can be formulated, for example, based on needs arising from user implementation, population and sample sizes, statistical constraints, or available computing power. Identification of this core attribute combination and its attribute content is of great importance because a core attribute combination should contain attributes that directly predispose the individual toward association with the query attribute. Subsets of attributes from this core attribute combination may therefore provide the most efficient and direct means of acquiring or eliminating an association with the query attribute, which is central to effectively modifying an individual's predisposition toward that query attribute.

In one embodiment of a computationally efficient method for compiling co-associating attributes, attribute combinations associated with a query attribute, including core attribute combinations, are identified without the need for supercomputing, even when evaluating populations comprising millions of individuals and attribute profiles each comprising billions of attributes. To help accomplish this, a representative subset of query-attribute-positive attribute profiles can be selected from a larger set of query-attribute-positive attribute profiles. The representative subset of attribute profiles can be used to identify candidate attributes and attribute combinations associated with the query attribute much more efficiently than using the entire set of query-attribute-profiles, while still providing the potential to identify relevant co-associating attributes. While not absolutely required, selecting a representative subset of attribute profiles may be advantageous when the set of query-attribute-positive attribute profiles includes thousands or millions of attribute profiles. The selection of a subset of query-attribute-positive attribute profiles can be a random selection or another appropriate and/or statistically valid method of selection. The size of this subset can vary, but for example, can comprise as few as 10 or as many as 100 or more attribute profiles. There may be several very different core attribute combinations associated with a given query attribute, potentially representing different pathways to achieve association with that query attribute. In a case where three or fewer core attribute combinations are expected to be associated with a given query attribute, as few as 10 randomly selected query-attribute-positive attribute profiles may enable the identification of those attribute combinations. If it is expected that more than three core attribute combinations are associated with the query attribute, then selecting a higher number of query-attribute-positive attribute profiles for the subset may be advisable.

In one embodiment of a computationally efficient method for compiling co-associating attributes, a very beneficial step to the successful and efficient identification of co-associating attributes involves eliminating consideration of attributes in query-attribute-positive attribute profiles that also occur in a large portion of the query-attribute-negative attribute profiles. As previously described herein, this can be accomplished by comparing one or more query-attribute-positive attribute profiles with an appropriately selected (e.g., randomly selected) subset of query-attribute-negative individuals to eliminate those attributes possessed by query-attribute-positive individuals that occur at a high frequency in the query-attribute-negative group (for example at 80% or greater frequency) and are therefore likely to either have no association with the query attribute, or a negative association. Failure to eliminate such commonly occurring attributes may add complexity to an attribute combination without increasing the strength of association of its core attribute combination with the query attribute. It is therefore advantageous to eliminate such attributes initially, in order to arrive at determination of the core attribute combinations as quickly, efficiently and accurately as possible. While not absolutely required, this approach greatly increases efficiency when comparing numerous attribute profiles each containing large numbers of attributes, as for example when processing whole genomic attribute profiles of a large population where each attribute profile contains at least 3 billion nucleotide attributes which on average will be 99.9% identical between any given pair of individuals. The comparison of a query-attribute-positive attribute profile with a subset of query-attribute-negative attribute profiles can identify a subset of attributes from the query-attribute-positive attribute profile that do not occur in a portion of the query-attribute-negative attribute profiles. This identified subset of attributes can be referred to as a set of candidate attributes. A set of candidate attributes can be further processed to identify combinations of the candidate attributes that co-associate with the query attribute.

In a further embodiment of a computationally efficient method for compiling co-associating attributes, a divide-and-conquer approach can be used to greatly increase the efficiency of identifying attribute combinations that are associated with a query attribute. This approach partitions (subdivides, divides up, or segments) a set of attribute profiles into subsets of attribute profiles, each subset comprising those attribute profiles that share the most attributes in common. Each iteration of the divide-and-conquer approach partitions the query-attribute-positive set (or subset) of attribute profiles into at least two subsets, and multiple iterations can be used to generate additional subsets. The attribute profiles that comprise each subset are evaluated to identify the largest attribute combination that they share in common. Initially a first query-attribute-positive attribute profile is selected from the query-attribute-positive set of attribute profiles. As an example using a set of 10 attribute profiles, a first attribute profile is selected from the set of 10 attribute profiles. This first attribute profile, attribute profile #1, can then be used in a series of pairwise comparisons with each of the other query-attribute-positive attribute profiles in the set. In a preferred embodiment, all possible pairwise comparisons of the first attribute profile with the other attribute profiles are performed. In this example, the possible pairings are {#1,#2}, {#1,#3}, {#1,#4}, {#1,#5}, {#1,#6}, {#1,#7}, {#1,#8}, {#1, #9}, and {#1,#10}, for a total of nine pairwise attribute profile comparisons. If each of the 10 individuals has an associated attribute profile consisting of $10^6$ attributes, then this example would require performing $9 \times 10^6$ individual attribute comparisons (9 paired attribute profiles × $10^6$ attributes per attribute profile). Sets of attributes (i.e., attribute combinations) constituting the intersection in content between the two attribute profiles of each pairwise comparison can be stored to generate a first set of attribute combinations, wherein each attribute combination can be stored in association with the pair of attribute profiles from which it was generated. The largest attribute combination occurring in the first set of attribute combinations can be identified and referred to as the primary attribute combination. As an example, if the largest intersection of attributes occurs in the paired comparison {#1,#4}, then this intersection produces the primary attribute combination for the subset of attribute profiles #1-#10 under consideration. This primary attribute combination can serve as the basis for partitioning the query-attribute-positive set of attribute profiles into subsets of attribute profiles, one of which can include attribute profiles that are most similar to #1 and #4. This is achieved by using the primary attribute combination in a series of pairwise comparisons with each of the other attribute combinations previously stored in the first set of attribute combinations. Sets of attributes constituting the intersection in content between the two attribute combinations of each pairwise comparison are stored to generate a second set of attribute combinations, wherein each attribute combination is stored in association with the three corresponding attribute profiles from it was generated. Continuing from the example above, by using the primary attribute combination corresponding to {#1,#4} in pairwise comparisons with each of the other attribute combinations in the first set corresponding to {#1,#2}, {#1,#3}, {#1,#5}, {#1,#6}, {#1, #7}, {#1,#8}, {#1,#9}, and {#1,#10}, the resulting eight intersections of attributes corresponding to the triplets of attribute profiles {#1,#2,#4}, {#1,#3,#4}, {#1,#4,#5}, {#1, #4,#6}, {#1,#4,#7}, {#1,#4,#8}, {#1,#4,#9}, and {#1,#4,#10} can be stored as a second set of attribute combinations. The query-attribute-positive subset of attribute profiles can then be divided into at least two subsets based on the sizes of the attribute combinations in the second set as compared with the size of the primary attribute combination. More specifically, the attribute profiles which correspond to attribute combinations in the second set that are equal to or larger than a predetermined fraction of the size of the primary attribute combination, for example those that are at least 50% of the size of the primary attribute combination, can be assigned to a first subset of attribute profiles, while the attribute profiles corresponding to the remaining attribute combinations which are less than the predetermined fraction of the size of the primary attribute combination, for example those that are less than 50% of the size of the primary attribute combination, can be assigned to a second subset of attribute profiles. By doing this, the attribute profiles that are most similar to the two attribute profiles which generated the primary attribute combination in the current iteration are clustered together into the first subset. The choice of 50% as the predetermined fraction of the size of the primary attribute combination is arbitrary in these examples, and can be adjusted higher or lower to respectively increase or decrease the degree of similarity desired of attribute profiles that are partitioned into a subset. As such, the predetermined fraction of the size of the primary attribute combination essentially acts as a stringency parameter for including and excluding attribute profiles from the subsets, and it can have substantial influence on the number of attributes profiles partitioned into each subset, as well as the number of subsets that will ultimately be formed.

Continuing with the above example in which the primary attribute combination derived from comparison of attribute profiles #1 and #4, the first subset will include attribute profiles #1 and #4 as well as any other attribute profiles that correspond with attribute combinations in the second set that are at least 50% of the size of that primary attribute combination. For this example, assume that attribute profile triplets {#1,#4,#6} and {#1,#4,#9} are associated with attribute combinations in the second set that are equal to or greater than 50% of the size of the primary attribute combination. Attribute profiles #6 and #9 would therefore be included in the first subset of attribute profiles along with attribute profiles #1 and #4. Attribute profiles #2, #3, #5, #7, #8, and #10 on the other hand are assigned to the second subset because they are associated with attribute combinations in the second set that are less than 50% of the size of the primary attribute combination. The largest attribute combination shared by the attribute profiles of the first subset can then be stored as a candidate attribute combination in a set of candidate attribute combinations.

The attribute profiles in the second subset can then be processed through a reiteration of the method, where the second subset can be redesignated as the subset of attribute profiles, a new first attribute profile can be selected from this subset of attribute profiles, a new first set of attribute combinations can be generated from pairwise comparison of the first attribute profile with the other attribute profiles of this subset, a new primary attribute combination can be determined, a new second set of attribute combinations can be generated from the pairwise comparison of the primary attribute combination with the other attribute combinations in the first set of attribute combinations, and the current subset of attribute profiles can be divided into a new first subset and a new second subset based on the comparison of each of the attribute combinations in the second set with the primary attribute combination. The largest attribute combination occurring in all the attribute profiles of the new first subset can be stored as a candidate attribute combination in the set of candidate attribute combinations. Reiteration can continue in this manner, beginning with the current second subset redesignated as the subset of attribute profiles, until an iteration is reached where a new second subset containing one or more attribute profiles cannot be formed (i.e., the new second subset formed is an empty/null set).

To exemplify this reiteration process continuing with the attribute profiles from the above example, the second subset comprising attribute profiles #2, #3, #5, #7, #8, and #10 is redesignated as the subset of attribute profiles, and attribute profile #2 can be selected as a first attribute profile for this subset. The selected attribute profile #2 is then used to determine the attribute intersections of the five pairwise attribute profile comparisons corresponding to {#2,#3}, {#2,#5}, {#2, #7}, {#2,#8}, and {#2,#10}. Assuming attribute profiles #5 and #10 are found to cluster with attribute profile #2 as a result of evaluating the intersection in attribute content of the pairwise comparisons as described above, partition of this subset of attribute profiles creates a new first subset containing attribute profiles #2, #5 and #10, and a new second subset containing attribute profiles #3, #7, and #8. The largest attribute combination corresponding to the intersection of attribute profiles #2, #5 and #10 is stored as a candidate attribute combination in the set of candidate attribute combinations. Reiterative processing of the second subset comprising attribute profiles #3, #7 and #8 proceeds with attribute profile #3 selected as the first attribute profile, which is then used to perform the two pairwise comparisons {#3,#7} and {#3,#8}. Assuming a comparison finds these three attribute profiles to cluster together, no new second subset can be generated. The largest attribute combination corresponding to the intersection of attribute profiles #3, #7 and #8 is stored as a candidate attribute combination in the set of candidate attribute combinations. Frequencies of occurrence of each of the candidate attribute combinations that were generated and stored in the set of candidate attribute combinations can be determined in the query-attribute-positive set of attribute profiles and in the query-attribute-negative set of attribute profiles so that strength of association of the candidate attribute combinations with the query attribute can be determined and used as desired for other methods.

By clustering the attribute profiles into subsets, the divide-and-conquer approach substantially increases efficiency because no comparisons of attribute profiles are performed across subsets. Consequently, the number of attribute profile comparisons required by the divide-and-conquer approach is much less than that required by just the first step of the nonpreferred method described previously which compares all possible combinations of attribute profiles that can be formed from a set of attribute profiles. To demonstrate this, consider again the above example which used the divide-and-conquer approach to partition a set of 10 query-attribute-positive attribute profiles into three nearly equally sized subsets of attribute profiles to generate three candidate attribute combinations. That example required a total of 16 pairwise comparisons of attribute profiles over three iterations (9+5+2=16). In contrast, the nonpreferred method would require 45 pairwise comparisons of attribute profiles in its first step (10 choose 2=45). When processing a much larger set, for example a set of 1,000 query-attribute-positive attribute profiles, the divide-and-conquer approach would require 1,996 pairwise attribute profile comparisons in a scenario in which the 1,000 attribute profiles cluster into three nearly equally sized subsets of attribute profiles (999+665+332=1,996), while the nonpreferred method would require 499,500 pairwise comparisons in its first step (1,000 choose 2=499,500). Therefore, as the number of attribute profiles in the query-attribute-positive set increases, the computational burden of the divide-and-conquer approach increases linearly, while the computational burden of the nonpreferred method increases exponentially. This represents a tremendous advantage in computational efficiency of the divide-and-conquer approach.

In one embodiment, a plurality of sets of attributes (e.g., attribute profiles) are evaluated and clustered into subsets according to the divide-and-conquer approach described herein, wherein the subsets formed can be mapped to a first half and second half of the plurality of sets of attributes by clustering the two most similar attribute sets with other attribute sets that are highly similar to those two. Alternatively, other clustering methods which look for similarities and which provide a basis for aggregation of attributes can be used (e.g., seeding). In one embodiment all attributes are given binary values (present or not present) and the clustering is performed based on the presence of combinations of attributes within the query-attribute-positive group. In an alternate embodiment some attributes are continuous or multi-valued (e.g. obesity) and described on a continuous value or discrete multi-valued basis. A number of clustering algorithms, including but not limited to K-means clustering, as well as determination of similarity measures including geometric distance or angles can be used to determine one or more of the subsets. Additionally, seeding techniques can be used to generate subsets, for example by requiring that one or more attribute profiles that nucleate formation of one or more subsets contain a minimal specified or predetermined set of attributes (i.e., a core attribute combination). In one embodiment, if a particular attribute or set of attributes is known to be causally associated with a particular outcome (i.e., a query attribute), that attribute or set of attributes can be used as the basis for clustering attributes, attribute profiles, and/or individuals into subsets (clusters).

Each candidate attribute combination generated by the divide-and-conquer approach constitutes the largest combination of attributes occurring within all of the attribute profiles of a particular subset of attribute profiles. As explained previously, the largest attribute combination identified may contain smaller combinations of attributes (i.e., core attribute combinations) that also co-associate with query attribute. A further embodiment of a computationally efficient method for compiling co-associating attributes is able to identify core attribute combinations, contained within a larger candidate attribute combination for example, using a top-down approach. These smaller core attribute combinations, by virtue of the way in which they are identified, can contain attributes which are the most essential attributes for contributing to co-association with the query attribute. Candidate attribute combinations determined by the divide-and-conquer approach are preferably used as the starting point for identifying core attribute combinations. The following top-down approach to identifying a core attribute combination begins with generating subcombinations of attributes selected from a candidate attribute combination, the number of attributes in each subcombination being less than that of the candidate attribute combination. In one embodiment, the number of attributes in each attribute subcombination is one less than the candidate attribute combination from which the attributes are selected. In a further embodiment, all possible attribute subcombinations containing one less attribute than the candidate attribute combination are generated, so that for every attribute comprising the candidate attribute combination there will be exactly one attribute subcombination generated which lacks that attribute. The frequencies of occurrence of each of the candidate attribute combinations and attribute subcombinations can be determined in the query-attribute-positive set of attribute profiles and in the query-attribute-negative set of attribute profiles, and based on the frequencies of occurrence, each subcombination having a lower strength of association with the query attribute than the candidate attribute combination from which it was generated is identified. A lower strength of association would be expected to result from an increased frequency of occurrence, in the query-attribute-negative set of attribute profiles, of the attribute subcombination relative to the candidate attribute combination from which it was generated. Because each attribute subcombination is missing at least one attribute relative to the candidate attribute combination from which it was generated, a missing attribute can be readily identified as a core attribute responsible for the lower strength of association since it constitutes the only difference between the attribute subcombination and the candidate attribute combination. By evaluating all of the attribute subcombinations that are generated from a particular candidate attribute combination with respect to strength of association with the query attribute as above, a set of attributes constituting a core attribute combination can be identified. The identified core attributes can be stored as candidate attributes, or as a combination of candidate attributes (i.e., a candidate attribute combination). Various combinations of the core attributes can be independently evaluated for frequencies of occurrence and strength of association with the query attribute to determine a set containing even smaller attribute combinations comprised of subsets of core attributes, each of these even smaller core attribute combinations potentially having very different strengths of association with the query attribute. When compiled into attribute combination databases, these numerous small core attribute combinations can enable methods of predisposition prediction and predisposition modification to provide considerably more accurate, comprehensive, flexible and insightful results.

In another embodiment of a computationally efficient method for compiling co-associating attributes, a bottom-up approach is used for determining attribute combinations that are associated with a query attribute. This bottom-up approach generates sets of attributes in stages, starting with small attribute combinations and progressively building on those to generate larger and larger attribute combinations. At each stage, only the attribute combinations that are determined to be statistically associated with the query attribute are used as building blocks for the next stage of generating larger attribute combinations. The attributes used for generating these attribute combinations can be selected from an attribute profile, from an attribute combination, from a set of candidate attributes, or from a candidate attribute combination, for example. At each stage, all of the attribute combinations that are generated contain the same number of attributes, and can therefore be referred to as a set of n-tuple combinations of attributes, where n is a specified positive integer value designating the number of attributes in each n-tuple combination of attributes. This method can be used for de novo identification of attribute combinations that are statistically associated with a query attribute, as well as for identifying one or more core attribute combinations from a previously identified candidate attribute combination. The method can begin by generating n-tuples of any chosen size, size being limited only by the number of attributes present in the attribute profile, attribute combination, or set of attributes from which attributes are selected for generating the n-tuple combinations. However, it is preferable to begin with small size n-tuple combinations if using this bottom-up approach for the de novo identification of attribute combinations because this method typically requires generating all possible n-tuple combinations for the chosen starting value of n in the first step. If the n-tuple size chosen is too large, an unmanageable computational problem can be created. For example, if n=50 is chosen as the starting n-tuple size with a set of 100 attributes, all possible 50-tuple combinations from the 100 attributes would be $1 \times 10^{29}$ combinations, which is a currently unmanageable even with current supercomputing power. Therefore, it is more reasonable to choose 2-tuple, 3-tuple, 4-tuple, or 5-tuple sized combinations to start with, depending on the size of the set of attributes from which the n-tuple combinations will be generated and the amount of computing time and computer processor speed available. Once a first set of n-tuple combinations of attributes is generated, frequencies of occurrence are determined for each n-tuple combination in a query-attribute-positive set of attribute profiles and in a query-attribute-negative set of attribute profiles. Each n-tuple combination that is statistically associated with the query attribute is identified based on the frequencies of occurrence and stored in a compilation containing attribute combinations that are associated with the query attribute. If no n-tuple combinations are determined to be statistically associated with the query attribute, the value of n can be incremented by one and the method can be reiterated, beginning at the first step, for the larger n-tuple size. If, on the other hand, at least one n-tuple was determined to be statistically associated with the query attribute and stored in the compilation, a set of (n+1)-tuple combinations are generated by combining each stored n-tuple combination with each attribute in the set of attributes that does not already occur in that n-tuple (combining an n-tuple with an attribute from the set that already occurs in that n-tuple would create an (n+1)-tuple containing an attribute redundancy, which is undesirable). Next, frequencies of occurrence of the (n+1)-tuple combinations are determined and those (n+1)-tuple combinations which have a higher strength of association with the query attribute than the n-tuple combinations from which they were generated are stored in the compilation containing attribute combinations that are associated with the query attribute. Storing an (n+1)-tuple combination that does not have a higher strength of association with the query attribute than the n-tuple combination from which it is generated effectively adds an attribute combination to the compilation which contains an additional attribute that is not positively associated with the query attribute, something that is undesirable. Provided at least one (n+1)-tuple combination has a stronger statistical association with the query attribute and was stored, the value of n is incremented by one and a next iteration of the method is performed, so that the (n+1)-tuple combinations generated during the current iteration become the n-tuple combinations of the next iteration. By generating progressively larger n-tuple combinations at each iteration and storing those that have increasingly stronger statistical association with the query attribute than the ones before, a compilation of attribute combinations that are associated with the query attribute is generated which can be used effectively for methods of attribute prediction, predisposition prediction and predisposition modification.

In one embodiment a method of identifying predisposing attribute combinations is provided which accesses a first dataset containing attribute combinations and statistical computation results that indicate the potential of each attribute combination to co-occur with a query attribute, the attributes being pangenetic, physical, behavioral, and situational attributes. A tabulation can be performed to provide, based on the statistical computation results, those attribute combinations that are most likely to co-occur with the query attribute, or a rank-ordering of attribute combinations of the first dataset that co-occur with the query attribute. In a further embodiment, ranking of the attribute combinations can include consideration of the attribute content of the attribute combinations, such as whether certain attributes are present or absent in a particular attribute combination, what percentage of attributes in a particular attribute combination are modifiable, what specific modifiable attributes are present in a particular attribute combination, and/or what types or categories of attributes (i.e., epigenetic, genetic, physical, behavioral, situational) are present in a particular attribute and in what relative percentages.

Similarly, a system can be developed which contains a subsystem for accessing or receiving a query attribute, a second subsystem for accessing a dataset containing attribute combinations comprising pangenetic, physical, behavioral and situational attributes that co-occur with one or more query attributes, a communications subsystem for retrieving the attribute combinations from at least one external database, and a data processing subsystem for tabulating the attribute combinations. The various subsystems can be discrete components, configurations of electronic circuits within other circuits, software modules running on computing platforms including classes of objects and object code, or individual commands or lines of code working in conjunction with one or more Central Processing Units (CPUs). A variety of storage units can be used including but not limited to electronic, magnetic, electromagnetic, optical, opto-magnetic and electro-optical storage.

In one application the method and/or system is used in conjunction with one or more databases, such as those that would be maintained by health-insurance providers, employers, or health-care providers, which can serve to store the aforementioned attribute combinations and corresponding statistical results. In one embodiment the attribute combinations are stored in a separate dataset from the statistical results and the correspondence is achieved using identifiers or keys present in (shared across) both datasets. In another embodiment the attribute combinations and corresponding statistical results data are stored with other attribute data. A user, such as a clinician, physician or patient, can input a query attribute, and that query attribute can form the basis for tabulating attribute combinations associated with that query attribute. In one embodiment the associations have been previously stored and are retrieved and displayed to the user, with the highest ranked (most strongly associated) combinations appearing first. In an alternate embodiment the tabulation is performed at the time the query attribute is entered and a threshold used to determine the number of attribute combinations to be displayed.

Figure 19:
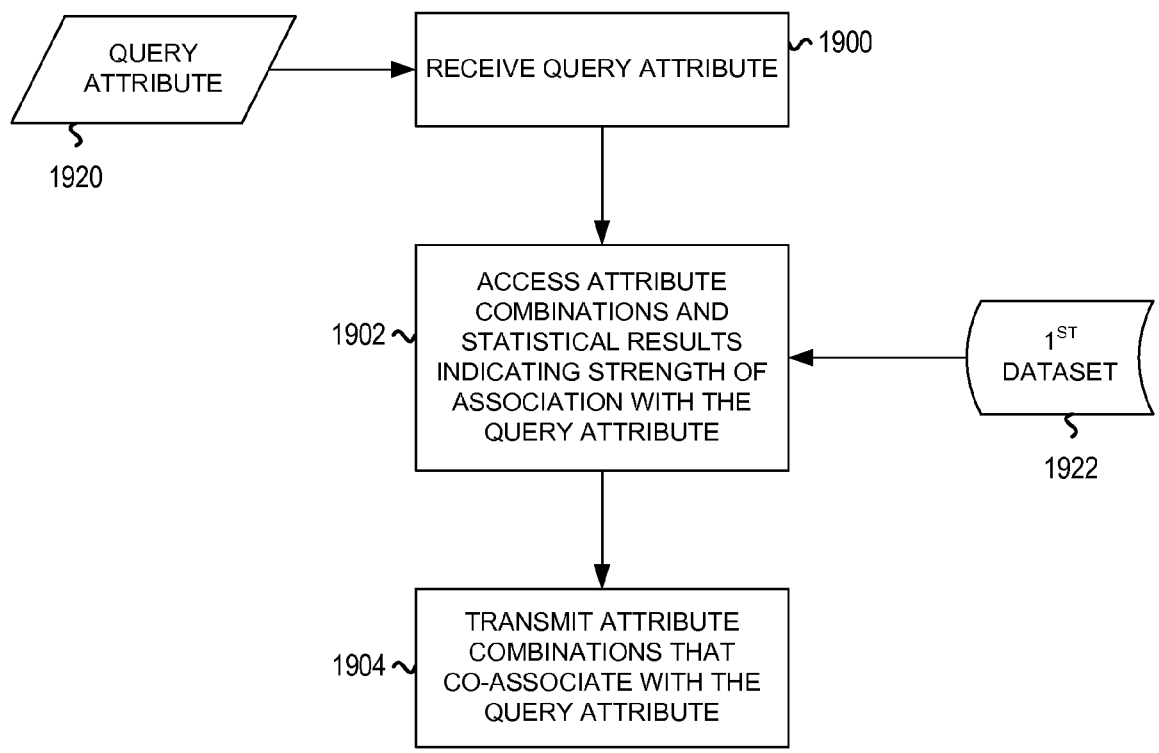
FIG. 19 illustrates a flowchart for a method of identifying predisposing attribute combinations.

FIG. 19 illustrates a flow chart for a method of attribute identification providing tabulation of attribute combinations that co-associate with an attribute of interest provided in a query. In receive query attribute step 1900, query attribute 1920 can be provided as one or more attributes in a query by a user. Alternatively, query attribute 1920 can be provided by automated submission, as part of a set of one or more stored attributes for example. In access attribute combinations and statistical results indicating strength of association with the query attribute step 1902, 1st dataset 1922 containing attribute combinations that co-occur with the query attribute and statistical results that indicate the corresponding strength of association of each of the attribute combinations with the query attribute is accessed. For this example the query attribute is 'A', and a representative 1st dataset is shown in FIG. 16. In transmit attribute combinations that co-associate with the query attribute step 1904, attribute combinations that co-occur with the query attribute are transmitted as output, preferably to at least one destination such as a user, a database, a dataset, a computer readable memory, a computer readable medium, a computer processor, a computer network, a printout device, a visual display, a digital electronic receiver and a wireless receiver. In a further embodiment, the output may be transmitted as a tabulation having the attribute combinations ordered according to a rank assigned to each attribute combination based on their strength of association with the query attribute and/or attribute content, and the corresponding statistical results which indicate the strength of association of the attribute combinations with the query attribute can also be included in the tabulation. Further, attribute combinations can be included or excluded based on a predetermined statistical threshold and/or attribute content. For example, attribute combinations below a minimum strength of association (i.e., a predetermined statistical threshold) and/or those containing certain user specified attributes may be excluded. In one embodiment, a minimum strength of association can be specified by the user in reference to one or more statistical measures. In an alternative embodiment, a predetermined statistical threshold can be computed de novo by the computer system based on statistical results associated with the dataset. This can provide flexible thresholds that can be tailored to the range of data values in a particular dataset or tailored to a particular application, thereby potentially yielding more useful results.

As an example, a minimum strength of association requiring relative risk > or =1.0 may be chosen. Based on this chosen requirement, the tabulated list of attribute combinations shown in FIG. 20 would result from processing the 1st dataset represented in FIG. 16. The attribute combinations are ordered according to rank. In this example, rank values were automatically assigned to each attribute combination based on the number of attributes in each attribute combination and the magnitude of the corresponding absolute risk value. The higher the absolute risk value, the lower the numerical rank assigned. For attribute combinations having the same absolute risk, those with more total attributes per combination receive a lower numerical rank. This treatment is based on two tendencies of larger predisposing attribute combinations. The first is the general tendency of predisposing attribute combinations containing more attributes to possess a higher statistical strength of association with the query attribute. The second is the general tendency for elimination of a single attribute from larger combinations of predisposing attributes to have less of an effect on strength of association with the query attribute. The resulting tabulated list of FIG. 20 therefore provides an rank-ordered listing of predisposing attribute combinations toward attribute 'A', where the first attribute combination in the listing is ranked as the most predisposing attribute combination identified and the last attribute combination in the listing is ranked as the least predisposing attribute combination of all predisposing attribute combinations identified for the population of this example.

In one embodiment a method for predicting predisposition of an individual for query attributes of interest is provided which accesses a first dataset containing attributes associated with an individual and a second dataset containing attribute combinations and statistical computation results that indicate strength of association of each attribute combination with a query attribute, the attributes being pangenetic, physical, behavioral and situational attributes. A comparison can be performed to determine the largest attribute combination of the second dataset that is also present in the first dataset and that meets a minimum statistical requirement, the result being stored in a third dataset. The process can be repeated for a plurality of query attributes to generate a predisposition profile of the individual, which can be in the form of a data file, a record or a report, containing the individual's predisposition toward (potential for association with) each of the plurality of query attributes. In one embodiment, a tabulation can be performed to provide a predisposition prediction profile, record or report indicating the predisposition of the individual for each of the query attributes. In one embodiment, predisposition can be defined as a statistical result indicating strength of association between an attribute or attribute combination and a query attribute.

Similarly, a system can be developed which contains a subsystem for accessing or receiving a query attribute, a second subsystem for accessing a dataset containing attributes of an individual, a third subsystem for accessing attribute combinations of pangenetic, physical, behavioral, and situational attributes that co-occur with one or more query attributes, a communications subsystem for retrieving the attribute combinations from at least one external database, and a data processing subsystem for comparing and tabulating the attribute combinations. The various subsystems can be discrete components, configurations of electronic circuits within other circuits, software modules running on computing platforms including classes of objects and object code, or individual commands or lines of code working in conjunction with one or more Central Processing Units (CPUs). A variety of storage units can be used including but not limited to electronic, magnetic, electromagnetic, optical, opto-magnetic and electro-optical storage.

In one application the method and/or system is used in conjunction with one or more databases, such as those that would be maintained by health-insurance providers, employers, or health-care providers, which can serve to store the aforementioned attribute combinations and corresponding statistical results. In one embodiment the attribute combinations are stored in a separate dataset from the statistical results and the correspondence is achieved using identifiers, links or keys present in (shared across) both datasets. In another embodiment the attribute combinations and corresponding statistical results data is stored with the other attribute data. A user, such as a clinician, physician or patient, can input a query attribute, and that query attribute can form the basis for tabulating attribute combinations associated with that query attribute. In one embodiment the associations will have been previously stored and are retrieved and displayed to the user, with the highest ranked (most strongly associated) combinations appearing first. In an alternate embodiment the tabulation is performed at the time the query attribute is entered, and a threshold can be used to determine the number of attribute combinations that are to be displayed.

Figure 21:
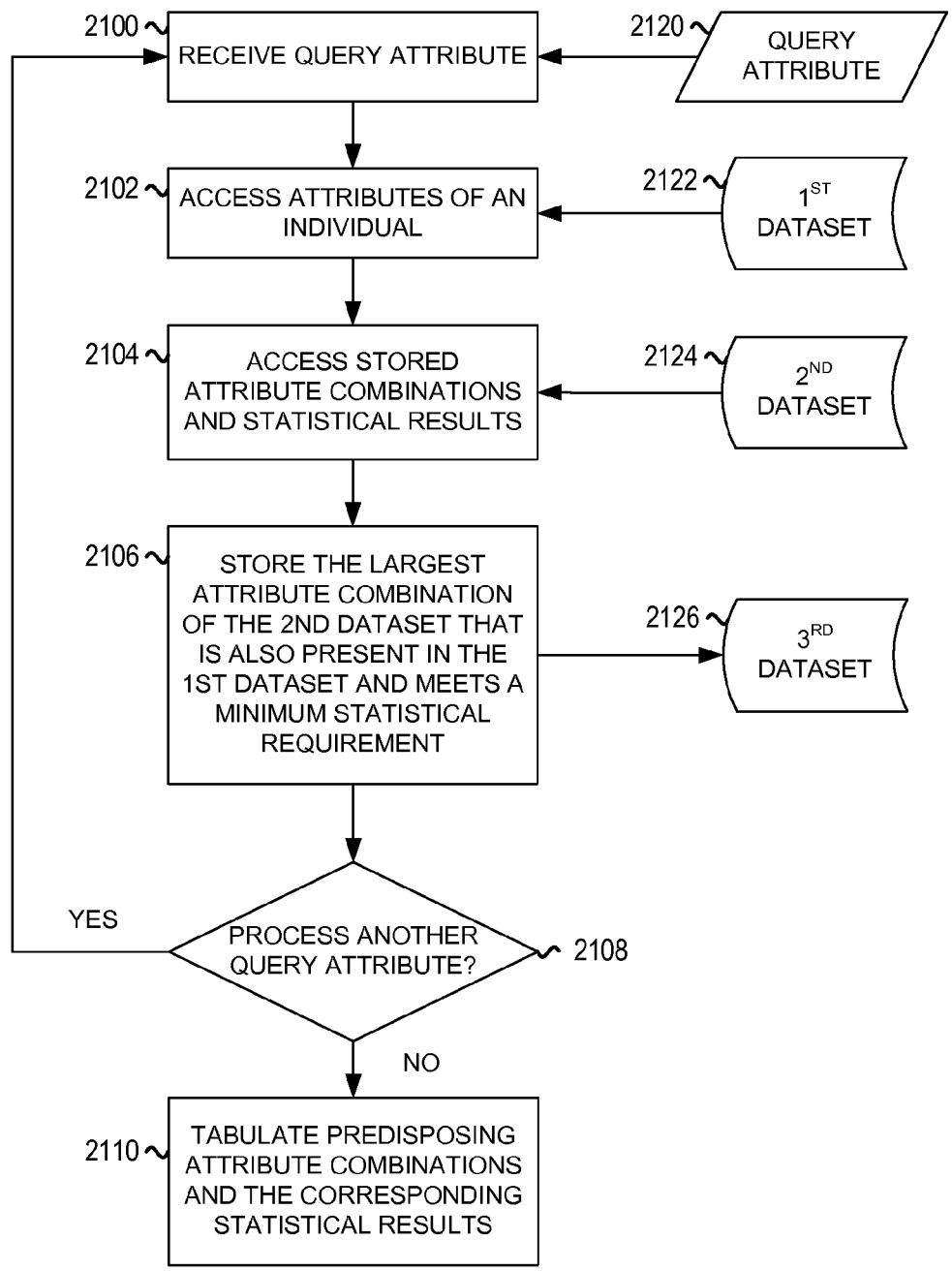
FIG. 21 illustrates a flowchart for a method of predisposition prediction.

FIG. 21 illustrates a flowchart for a method of predicting predisposition of an individual toward an attribute of interest with which they currently have no association or their association is currently unknown. In receive query attribute step 2100, query attribute 2120 can be provided as one or more attributes in a query by a user. Alternatively, query attribute 2120 can be provided by automated submission, as part of a set of one or more stored attributes that may be referred to as key attributes. These key attributes can be submitted as a list, or they may be designated attributes within a dataset that also contains predisposing attribute combinations with corresponding statistical results indicating their strength of association with one or more of the key attributes.

For this example, query attribute 'A' is submitted by a user in a query. In access attributes of an individual step 2102 the attributes of an individual whose attribute profile is contained in a 1st dataset 2122 are accessed. A representative 1st dataset for individual #112 is shown in FIG. 22A. In access stored attribute combinations and statistical results step 2104, attribute combinations and corresponding statistical results for strength of association with query attribute 2120 contained in 2nd dataset 2124 are accessed. A representative 2nd dataset for this example is shown in FIG. 22B. In store the largest attribute combination of the 2nd dataset that is also present in the 1st dataset and meets a minimum statistical requirement step 2106, attribute combinations of 2nd dataset 2124 that are also present in 1st dataset 2122 are identified by comparison, and the largest identified attribute combination shared by both datasets and its corresponding statistical results for strength of association with the query attribute are stored in 3rd dataset 2126 if a minimum statistical requirement for strength of association is met. Absolute risk and relative risk are the preferred statistical results, although other statistical computations such as odds and odds ratio can also be used. A representative 3rd dataset is shown in FIG. 23A. Individual #112 possesses the largest predisposing attribute combination CEFNTY, for which the corresponding statistical results for strength of association with attribute 'A' are an absolute risk of 1.0 and a relative risk of 15.3. In process another query attribute? step 2108, a decision is made whether to perform another iteration of steps 2100-2106 for another attribute of interest. Continuing with this example, attribute 'W' is received and another iteration is performed. For this example, after completing this iteration there are no additional attributes of interest submitted, so upon reaching process another query attribute? step 2108, a decision is made not to perform any further iterations. The method concludes with tabulate predisposing attribute combinations and the corresponding statistical results step 2110, wherein all or a portion of the data of 3rd dataset 2126 is tabulated to provide statistical predictions for predisposition of the individual toward each of the query attributes of interest. In one embodiment, the tabulation can include ordering the tabulated data based on the magnitude of the statistical results, or the importance of the query attributes.

In one embodiment, the tabulation can be provided in a form suitable for visual output, such as a visual graphic display or printed report. Attribute combinations do not need to be reported in predisposition prediction and can be omitted or masked so as to provide only the query attributes of interest and the individual's predisposition prediction for each. In creating a tabulated report for viewing by a consumer, counselor, agent, physician, patient or consumer, tabulating the statistical predictions can include substituting the terminology 'absolute risk' and 'relative risk' with the terminology 'absolute potential' and 'relative potential', since the term 'risk' carries negative connotations typically associated with the potential for developing undesirable conditions like diseases. This substitution may be desirable when the present invention is used to predict predisposition for desirable attributes such as specific talents or success in careers and sports. Also, the numerical result of absolute risk is a mathematical probability that can be converted to chance by simply multiplying it by 100%. It may be desirable to make this conversion during tabulation since chance is more universally understood than mathematical probability. Similarly, relative risk can be represented as a multiplier, which may facilitate its interpretation. The resulting tabulated results for this example are shown in FIG. 23B, in which all of the aforementioned options for substitution of terminology and conversion of statistical results have been exercised. The tabulated results of FIG. 23B indicate that individual #112 has a 100% chance of having or developing attribute 'A' and is 15.3 times as likely to have or develop attribute 'A' as someone in that population not associated with attribute combination CEFNTY. The results further indicate that individual #112 has a 36% chance of having or developing attribute 'W' and is 0.7 times as likely to have or develop attribute 'W' as someone in that population not associated with attribute combination CE.

In one embodiment a method for individual destiny modification is provided which accesses a first dataset containing attributes associated with an individual and a second dataset containing attribute combinations and statistical computation results that indicate strength of association of each attribute combination with a query attribute, the attributes being pan-genetic, physical, behavioral and situational attributes. A comparison can be performed to identify the largest attribute combination of the second dataset that consists of attributes of the first dataset. Then, attribute combinations of the second dataset that either contain that identified attribute combination or consist of attributes from that identified attribute combination can be stored in a third dataset. The content of the third dataset can be transmitted as a tabulation of attribute combinations and corresponding statistical results which indicate strengths of association of each attribute combination with the query attribute, thereby providing predisposition potentials for the individual toward the query attribute given possession of those attribute combinations. In one embodiment destiny can be defined as statistical predisposition toward having or acquiring one or more specific attributes.

Similarly, a system can be developed which contains a subsystem for accessing or receiving a query attribute, a second subsystem for accessing a dataset containing attributes of an individual, a third subsystem for accessing attribute combinations comprising pangenetic, physical, behavioral, and/or situational attributes that co-occur with one or more query attributes, a communications subsystem for retrieving the attribute combinations from at least one external database, and a data processing subsystem for comparing and tabulating the attribute combinations. The various subsystems can be discrete components, configurations of electronic circuits within other circuits, software modules running on computing platforms including classes of objects and object code, or individual commands or lines of code working in conjunction with one or more Central Processing Units (CPUs). A variety of storage units can be used including but not limited to electronic, magnetic, electromagnetic, optical, opto-magnetic, and electro-optical storage.

In one application the method and/or system is used in conjunction with one or more databases, such as those that would be maintained by health-insurance providers, employers, or health-care providers, which can serve to store the aforementioned attribute combinations and corresponding statistical results. In one embodiment the attribute combinations are stored in a separate dataset from the statistical results and the correspondence is achieved using identifiers, links or keys present in (shared across) both datasets. In another embodiment the attribute combinations and corresponding statistical results data is stored with the other attribute data. A user, such as a clinician, physician or patient, can input a query attribute, and that query attribute can form the basis for tabulating attribute combinations associated with that query attribute. In one embodiment the associations will have been previously stored and are retrieved and displayed to the user, with the highest ranked (most strongly associated) combinations appearing first. In an alternate embodiment the tabulation is performed at the time the query attribute is entered, and a threshold can be used to determine the number of attribute combinations that are to be displayed.

Figure 24:
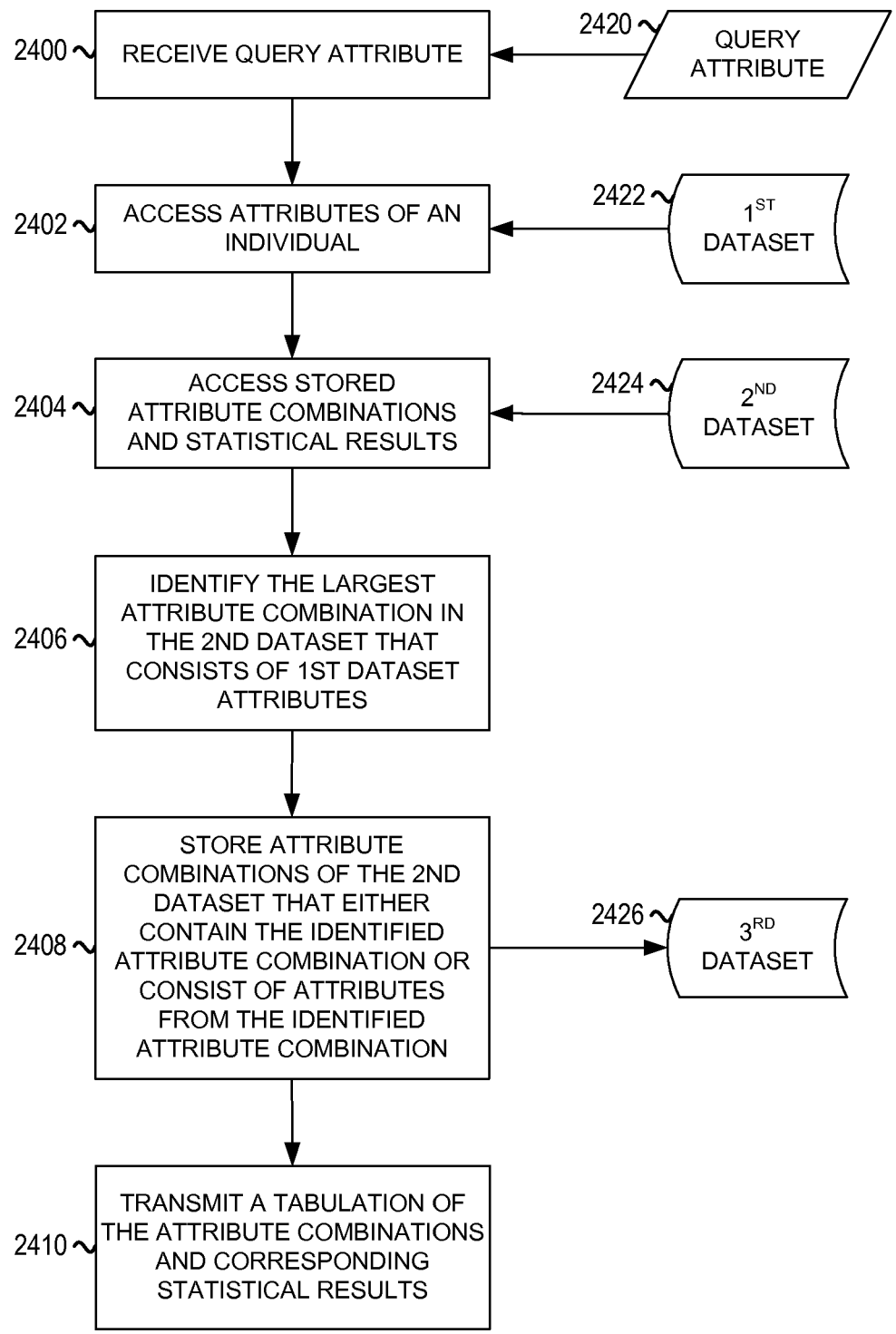
FIG. 24 illustrates a flowchart for a method of destiny modification.

FIG. 24 illustrates a flow chart for a method of providing intelligent destiny modification in which statistical results for changes to an individual's predisposition toward a query attribute that result from the addition or elimination of specific attribute associations in their attribute profile are determined. In receive query attribute step 2400, query attribute 2420 can be provided as one or more attributes in a query by a user or by automated submission. In this example query attribute 'A' is received. In access attributes of an individual step 2402, the attribute profile of a selected individual contained in 1st dataset 2422 is accessed. For this example, a representative 1st dataset for individual #113 is shown in FIG. 25A. In access stored attribute combinations and statistical results step 2404, attribute combinations from 2nd dataset 2424 and corresponding statistical results for strength of association with query attribute 2420 are accessed. FIG. 16 illustrates a representative 2nd dataset. In identify the largest attribute combination in the 2nd dataset that consists of 1st dataset attributes step 2406, the largest attribute combination in 2nd dataset 2424 that consists entirely of attributes present in 1st dataset 2422 is identified by comparison. In this example, the largest attribute combination identified for individual #113 is CEF. In store attribute combinations of the 2nd dataset that either contain the identified attribute combination or consist of attributes from the identified attribute combination step 2408, those attribute combinations of 2nd dataset 2424 that either contain the largest attribute combination identified in step 2406 or consist of attributes from that attribute combination are selected and stored in 3rd dataset 2426. For this example both types of attributes are stored, and the resulting representative 3rd dataset for individual #113 is shown in FIG. 25B. In transmit a tabulation of the attribute combinations and corresponding statistical results step 2410, attribute combinations from 3rd dataset 2426 and their corresponding statistical results are tabulated into an ordered list of attribute combinations and transmitted as output, wherein the ordering of combinations can be based on the magnitudes of the corresponding statistical results such as absolute risk values. Further, the tabulation may include only a portion of the attribute combinations from 3rd dataset 2426 based on subselection. A subselection of attribute combinations that are larger that the largest attribute combination identified in step 2406 may require the inclusion of only those that have at least a minimum statistical association with the query attribute. For example, a requirement can be made that the larger attribute combinations have an absolute risk value greater than that of the attribute combination identified in step 2406. This will ensure the inclusion of only those larger attribute combinations that show increased predisposition toward the query attribute relative to the attribute combination identified in step 2406. Similarly, a subselection of attribute combinations that are smaller than the attribute combination identified in step 2406 may require the inclusion of only those that have less than a maximum statistical association with the query attribute. For example, a requirement can be made that the smaller attribute combinations must have an absolute risk less than that of the attribute combination identified in step 2406. This will ensure the inclusion of only those smaller attribute combinations with decreased predisposition toward the query attribute relative to the attribute combination identified in step 2406.

In one embodiment the method for individual destiny modification is used to identify and report attributes that the individual may modify to increase or decrease their chances of having a particular attribute or outcome. In one embodiment, the tabulation of attribute combinations produced by the method of destiny modification is filtered to eliminate those attribute combinations that contain one or more attributes that are not modifiable. In an alternate embodiment, modifiable attributes are prioritized for modification in order to enable efficient destiny (i.e., predisposition) modification. In one embodiment, non-historical attributes (attributes that are not historical attributes) are considered modifiable while historical attributes are considered not modifiable. In another embodiment, non-historical behavioral attributes are considered to be the most easily or readily modifiable attributes. In another embodiment, non-historical situational attributes are considered to be the most easily or readily modifiable attributes. In another embodiment, non-historical physical attributes are considered the most easily or readily modifiable attributes. In another embodiment, non-historical pangenetic attributes are considered the most easily or readily modifiable attributes. In one embodiment, the modifiable attributes are ranked or otherwise presented in a manner indicating which are most easily or readily modifiable, which may include creating categories or classes of modifiable attributes, or alternatively, reporting attributes organized according to the attribute categories of the invention.

FIG. 25C illustrates an example of tabulation of attribute combinations for individual #113 without statistical subselection of the larger and smaller attribute combinations. The larger attribute combinations show how predisposition is altered by adding additional attributes to the largest attribute combination possessed by individual #113 (bolded), and the smaller attribute combinations show how predisposition is altered by removal of attributes from the largest attribute combination possessed by individual.

FIGS. 26A, 26B and 26C illustrate 1st dataset, 3rd dataset and tabulated results, respectively, for a different individual, individual #114, processed by the method for destiny modification using the same query attribute 'A' and the 2nd dataset of FIG. 16. The largest attribute combination possessed by individual #114 is CET, which has an absolute risk of 0.14 for predisposition toward query attribute 'A'. In this case, the tabulation of attribute combinations in FIG. 26C is obtained by imposing statistical subselection requirements. The subselection required that only those larger attribute combinations having an absolute risk greater than 0.14 be included and that only those smaller attribute combinations having an absolute risk less than 0.14 be included. These subselection requirements result in the exclusion of larger attribute combination CETY and smaller attribute combination CT from the tabulation. In this example, the tabulation also exemplifies how the nomenclature and statistical computations may be altered to increase ease of interpretation. Absolute risk results have been converted to percentages, relative risk results have been converted to multipliers, and the terms absolute potential and relative potential have been substituted for the terms absolute risk and relative risk respectively. The tabulated listing of attribute combinations indicates what individual #114 can do to increase or decrease their predisposition toward query attribute 'A'.

In one embodiment, a method for predisposition modification utilizing pangenetic, physical, behavioral, and/or situational attributes is provided in which a set of attributes for selective modification of the attribute profile of an individual are determined to enable the individual to modify their predisposition for acquiring an attribute of interest. The attribute of interest can be provided in the form of a query attribute received from a user or computer automated query. Additionally, a minimum strength of association value can also be provided as input to serve as a threshold for ensuring that the resulting set of attributes for predisposition modification will provide at least a minimum degree of statistical certainty that the individual will acquire the attribute of interest (i.e., a minimum potential for association with the query attribute) upon modifying their attribute profile. A minimum strength of association value can be a value or result of a statistical measure such as absolute risk or relative risk, that is used as a threshold for selecting attribute combinations having corresponding strength of association values at or above that threshold value, such as was previously described with respect to compiling attribute combination databases. Following receipt of a query attribute and minimum strength of association value, an attribute profile of an individual and a set containing attribute combinations and corresponding strength of association values (i.e., statistical measure results/values that can indicate the strength of association of an attribute combination with a query attribute, such as absolute risk and relative risk) can be accessed. One or more of the attribute combinations having corresponding strength of association values equal to or greater than the minimum strength of association value can be identified. From the identified attribute combinations, an attribute combination containing one or more attributes that do not occur in the attribute profile of the individual can be identified. The one or more attributes that do not occur in the attribute profile of the individual can be stored as a set of attributes for predisposition modification of the individual. The corresponding strength of association value of the selected attribute combination can be stored in association with the set of attributes for predisposition modification as an indicator of the individual's potential for association with the query attribute that would result from modifying the attribute profile of the individual with the set of attributes for predisposition modification.

Additionally, in one embodiment corresponding strength of association values can be stored for each of the attributes in the set of attributes for predisposition modification of the individual, to indicate the contribution of each of the attributes toward modifying the individual's potential for acquiring the query attribute. These corresponding strength of association values can be derived from the set containing attribute combinations and corresponding strength of association values. For example, in one embodiment the corresponding strength of association value of a first attribute combination can be subtracted from the strength of association value of a second attribute combination that differs from the first attribute combination only by possession of a single additional attribute. That single additional attribute can be considered to be responsible for any difference between the corresponding strength of association values of the two attribute combinations. Therefore, the strength of association value derived by this subtraction procedure can be assigned as a corresponding strength of association value to that single attribute which constitutes the difference in content between the two attribute combinations (pair of attribute combinations). If multiple pairs of attribute combinations in the set containing attribute combinations happen to differ by the same single attribute, then a plurality of corresponding strength of association values can be derived and then averaged to generate a the corresponding strength of association value for that single attribute.

A corresponding strength of association value derived for a single attribute as described above can be used to indicate that particular attribute's contribution (or potential/predicted contribution) toward predisposition to the query attribute. The single attribute can be an attribute selected from the set of attributes for predisposition modification. As such, a corresponding strength of association value can be derived for each attribute contained in the set of attributes for predisposition modification of the individual, and then stored in association with the particular attribute to which it refers (corresponds). Corresponding strength of association values can be stored within the set of attributes for predisposition modification, or they can be stored in a different set or database and linked to the attributes to which they correspond.

In one embodiment, if a particular subset of attributes are selected from the set of attributes for predisposition modification, a corresponding strength of association value can be derived for that particular subset of attributes by adding or mathematically compounding the corresponding strength of association values of the attributes that comprise that subset.

As such, a composite strength of association value can be generated to indicate the contribution toward predisposition that the subset of attributes will provide if used collectively to modify the individual's attribute profile. This composite strength of association value can be added to the individual's original strength of association with the query attribute, which can be determined by a method of predisposition prediction disclosed previously herein using the individual's original attribute profile. In this way a statistical prediction can be generated which indicates the individual's statistical potential for acquiring the query attribute upon modifying their original attribute profile with only a subset of attributes selected from the set of attributes for predisposition modification. In another embodiment, the corresponding strength of association value for a subset of attributes can be determined by directly deriving the value from a pair of attribute combinations, from the set of containing attribute combinations corresponding strength of association values, which differ in content by the full complement of attributes constituting the subset. This can provide a more accurate statistical prediction for the contribution of the subset to predisposition modification than the alternative of adding or compounding corresponding strength of association values that were individually determined for each of the attributes that comprise the subset. In one embodiment, corresponding strength of association values are generated using each approach, and the two values averaged to generate a single corresponding strength of association value for a subset of attributes for predisposition modification.

Similarly, a computer based system for predisposition modification utilizing pangenetic, physical, behavioral, and/or situational attributes can be developed which contains a data receiving subsystem for receiving a query attribute and a minimum strength of association value; a first data accessing subsystem for accessing an attribute profile of an individual; a second data accessing subsystem for accessing a set (e.g., an attribute combination database) containing attribute combinations and corresponding strength of association values that indicate the strength of association of each of the attribute combinations with the query attribute; a data processing subsystem comprising a data comparison subsystem for identifying one or more of the attribute combinations having corresponding strength of association values equal to or greater than the minimum strength of association value, and for identifying non-historical attributes within the set of attributes for predisposition modification of the individual as potentially modifiable attributes; a data processing subsystem comprising a data selection subsystem for selecting, from the identified attribute combinations, an attribute combination containing one or more attributes that do not occur in the attribute profile of the individual; a data storage subsystem for storing the one or more attributes that do not occur in the attribute profile of the individual as a set of attributes for predisposition modification of the individual; and a data storage subsystem for storing one or more corresponding strength of association values for the attributes in the set of attributes for predisposition modification. The various subsystems can be discrete components, configurations of electronic circuits within other circuits, software modules running on computing platforms including classes of objects and object code, or individual commands or lines of code working in conjunction with one or more Central Processing Units (CPUs). A variety of storage units can be used including but not limited to electronic, magnetic, electromagnetic, optical, opto-magnetic, and electro-optical storage.

In one application the method and/or system is used in conjunction with one or more databases, such as those that would be maintained by health-insurance providers, employers, or health-care providers, which can serve to store the aforementioned query attributes, attribute profiles, attribute combinations, corresponding strength of association values, and sets of attributes for predisposition modification. In one embodiment the attribute combinations are stored in a separate dataset from the corresponding strength of association values and the correspondence is achieved using identifiers, links or keys present in (shared across) both datasets. In another embodiment the attribute combinations and corresponding strength of association values data are stored with other attribute data. A user, such as a clinician, physician or patient, can input a query attribute (and optionally, a minimum strength of association value) which can form the basis for generating the set of attributes for predisposition modification. In one embodiment the attributes for predisposition modification can be stored and then retrieved and displayed to the user. They can be ranked, with the highest ranked attributes (those having the greatest influence on predisposition toward the query attribute or a plurality of query attributes, or those that are most readily or easily modified) appearing higher on a tabulation that can be presented to the user. In an alternate embodiment the tabulation can be performed using a predetermined threshold to determine the number of attributes to be displayed, stored or transmitted.

Figure 27:
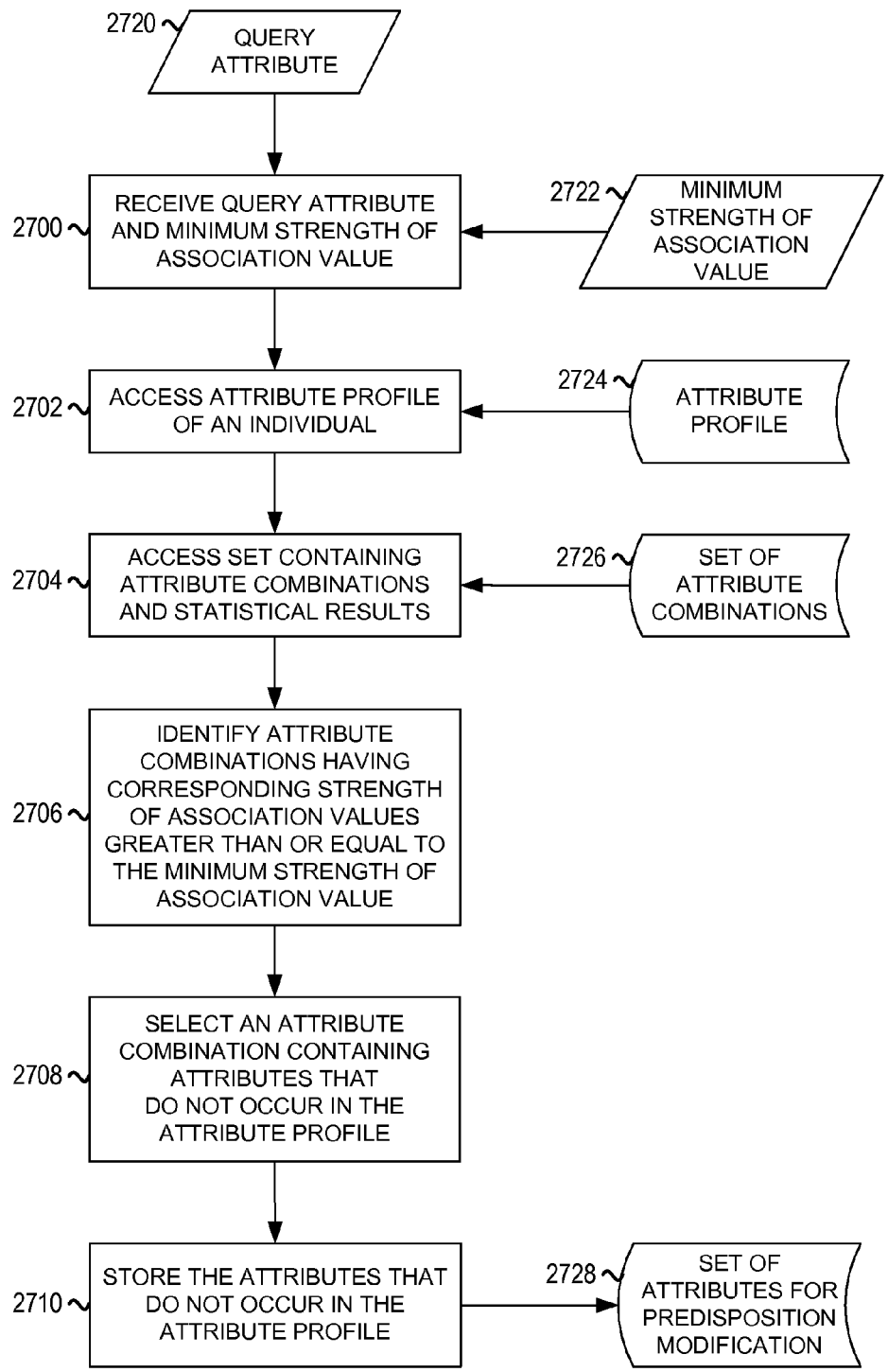
FIG. 27 illustrates a flowchart for a method of predisposition modification.

FIG. 27 illustrates a flow chart for a method of predisposition modification. In receive query attribute and minimum strength of association value step 2700, a query attribute 2720 and a minimum strength of association value 2722 are received from a user or automated submission. In access attribute profile of an individual step 2702, an attribute profile 2724 of an individual is accessed in preparation for comparison with a set of attribute combinations. In access set containing attribute combinations and statistical results step 2704, a set of attribute combinations 2726 which contains attribute combinations and corresponding strength of association values that indicate the strength of association of the attribute combinations with the query attribute are accessed. In identify attribute combinations having corresponding strength of association values greater than or equal to the minimum strength of association value step 2706, attribute combinations from the set of attribute combinations 2726 that have corresponding strength of association values above the minimum strength of association value received in step 2700 are identified for further processing. In select an attribute combination containing attributes that do not occur in the attribute profile step 2708, a single attribute combination containing one or more attributes that do not occur within attribute profile 2724 is selected from among the attribute combinations identified in previous step 2706. If more than one attribute combination from among those identified in step 2706 satisfies the requirement of containing one or more attributes that do not occur in the attribute profile of the individual, a requirement of selecting the attribute combination containing the fewest number of attributes that do not occur in the attribute profile of the individual can be imposed within step 2708. In store the attributes that do not occur in the attribute profile step 2710, the one or more attributes from the selected attribute combination that do not occur within attribute profile 2724 are stored as a set of attributes for predisposition modification 2728.

In one embodiment the method for predisposition modification can be repeated for a succession of query attributes to generate a plurality of sets of attributes for predisposition modification of the individual. In another embodiment, one or more sets of attributes for predisposition modification of the individual can be transmitted (i.e., output) to a user, a computer readable memory, a computer readable medium, a database, a computer processor, a computer on a network, a visual display, a printout device, a wireless receiver and/or a digital electronic receiver. In another embodiment, one or more sets of attributes for predisposition modification of the individual can be transmitted to generate a predisposition modification report or record. In another embodiment, non-historical attributes can be identified within the set of attributes for predisposition modification of the individual as potentially modifiable attributes. In a further embodiment, the identified non-historical attributes can be transmitted (i.e., output) to generate a report or record regarding potentially modifiable attributes for predisposition modification. In another embodiment, a requirement can be imposed that the one or more attributes that do not occur in the attribute profile of the individual must be non-historical attributes. In another embodiment, historical attributes can be eliminated from the set of attributes for predisposition modification of the individual. In another embodiment, genetic and/or epigenetic attributes can be eliminated from the set of attributes for predisposition modification of the individual. In another embodiment, genetic and/or epigenetic attributes can be considered not modifiable and consequently classified and/or treated as historical attributes that are not modifiable. In another embodiment, the set of attributes for predisposition modification of the individual (i.e., the output) can be linked to (i.e., stored in association with) an identifier of the individual, the attribute profile of the individual, and/or a record of the individual. In another embodiment the identity of the individual can be masked or anonymized. In another embodiment, corresponding strength of association values derived for the attributes in the set of attributes for predisposition modification can be stored along with those attributes in the set. In a further embodiment, the attributes in the set of attributes for predisposition modification of the individual can be rank-ordered based on the stored corresponding strength of association values. In another embodiment, each attribute occurring within a plurality of sets of attributes for predisposition modification toward one or more query attributes can be tabulated as a rank-ordered list of attributes that indicates which of the attributes have the greatest influence on predisposition toward the one or more query attributes, based on the number of sets that contain each attribute and the corresponding strength of association value (s) for each attribute. In one embodiment, the magnitude of effect that each attribute has on predisposition can be computed and used as a comparative measure to rank-order the predisposing attributes in the sets. For example, the magnitude of effect of each attribute on a plurality of query attributes can be calculated by adding the corresponding statistical results for an attribute with respect to one or more of the plurality of query attributes, to generate a composite statistical value for the effect of the attribute. This can be repeated for each of the predisposing attributes with respect to the particular query attributes they influence, and the resulting composite statistical values for each of the predisposing attributes compared with one another to rank the attributes, in order to indicate those that have the largest or smallest influence on predisposition to the plurality of query attributes, for example.

In a preferred mode of comparing genetic attributes, specifically nucleotide sequences, for embodiments of the present invention disclosed herein, the comparison can be a direct sequence comparison requiring two or more sequences to be the same at the nucleotide sequence level, wherein each nucleotide can be represented by an individual attribute containing both nucleotide sequence position and nucleotide identity information. Therefore, a nucleotide sequence can be presented as a set of genetic attributes containing individual genetic attributes comprising nucleotide sequence information, such a nucleotide position and nucleotide identity information for nucleotides constituting a contiguous genetic sequence like a chromosome, or a gene located within a chromosome. To increase efficiency, at the cost of loosing any important information contained in non-gene-coding regions of the genome, a direct sequence comparison between genomic sequences can use only gene coding and gene regulatory sequences since these represent the expressed and expression-controlling portions of the genome, respectively. In embodiments where computing power and time are available, a comparison of the whole genome can be performed as opposed to using only the 2% of the genome which encodes genes and gene regulatory sequences, since the noncoding region of the genome may still have effects on genome expression which influence attribute predisposition. that cont With respect to regions of the genome ain genes encoding proteins, in one embodiment, comparison engine 222 is permitted some degree of flexibility during comparison of nucleotide sequences, so that identical nucleotides at the same nucleotide positions within two nucleotide sequences encoding the same protein is not always required. For example, when a single nucleotide difference between two sequences encoding the same protein is deemed unlikely to result in a functional difference between the two encoded proteins, it is beneficial to make the determination that the two sequences are the same (i.e., equivalent, or identical) even though they are actually not identical. The reason for allowing non-identical matches being that since the nucleotide difference is functionally silent with respect to the encoded protein that is ultimately expressed, it should not have a differential effect on attribute predisposition. A number of equivalence rules can be provided to comparison engine 222 to guide such decision making. These rules are based on the knowledge of several phenomena. For example, within an open reading frame of a nucleotide sequence encoding a protein, a single nucleotide difference in the 3rd nucleotide position of a codon—termed the wobble position—often does not change the identity of the amino acid encoded by the codon, and therefore does not change the amino acid sequence of the encoded protein. Determination of whether or not a particular nucleotide change in a wobble position alters the encoded protein amino acid sequence is easily made based on published information known to those in the art. Types of changes that are unlikely to affect protein function are those that are known to be functionally silent (i.e., silent mutations, and silent amino acid substitutions), those that result in conservative amino acid changes particularly in non-enzymatic, non-catalytic, nonantigenic or non-transmembrane domains of the protein, and those that simply alter the location of truncation of a protein within the same domain of one protein relative to another. Truncation of a protein can result from a nonsense mutation introduced by nucleotide substitution (i.e., point mutations), or alternatively, by nucleotide insertions or deletions which cause a frameshift within the open reading frame that introduces a stop codon acting as a premature translation termination signal of the encoded protein.

Allowing flexibility in sequence matching can increase the number of sequences determined to be identical, but may also reduce the sensitivity of the invention to detect predisposing attributes. There may be sequence changes which are thought to be innocuous or inconsequential based on current scientific knowledge that in actuality are not. For example, nucleotide changes in the wobble codon position that do not change the amino acid sequence may appear to be inconsequential, but may actually impact the stability of the intermediary RNA transcript required for translation of nucleotide sequence into the encoded protein, thus having a significant effect on ultimate levels of expressed protein. Therefore, application of the rules can be left to up the user's discretion or automatically applied when processing small populations of individuals where the low opportunity for exact matches resulting from small sample size increases the probability of obtaining an uninformative result.

In one embodiment, when a particular set of rules fails to provide sufficient detection of predisposing attributes, the rules can be modified in order to provide higher granularity or resolution for the discovery of predisposing attributes. As such, nucleotide changes in the wobble codon position may be examined in certain applications. By varying the rules, the appropriate level of granularity or resolution can be determined. In one embodiment, the rules are varied on a test population (which can be comprised of both attribute-positive and attribute-negative individuals) in an effort to determine the most appropriate rules for the greater population.

Based on this knowledge, the following equivalence rules can be applied by comparison engine 222 when comparing two nucleotide sequences:

- a) a direct sequence comparison may determine two protein-encoding nucleotide sequences to be equivalent if they encode the same protein and differ only by one or more nucleotides within the open reading frame that do not alter the amino acid sequence of the encoded protein;
- b) a direct sequence comparison may determine two protein-encoding nucleotide sequences to be equivalent if they encode the same protein and differ only by one or more nucleotides within the open reading frame that result in conservative amino acid substitutions within the amino acid sequence of the encoded protein;
- c) a direct sequence comparison may determine two protein-encoding nucleotide sequences to be equivalent if they encode the same protein and differ only by one or more nucleotides within the open reading frame that result in conservative amino acid substitutions anywhere within the amino acid sequence of the encoded protein except for enzymatic, transmembrane or antigen-recognition domains;
- d) a direct sequence comparison may determine two protein-encoding nucleotide sequences to be equivalent if they encode the same protein and differ only by one or more nucleotides within the open reading frame that result in silent amino acid substitutions;
- e) a direct sequence comparison may determine two nucleotide sequences that do not encode amino acid sequences to be equivalent if they differ only by the identity of nucleotide mutations occurring at the same position within both sequences;
- f) a direct sequence comparison may determine two protein-encoding nucleotide sequences to be equivalent if they encode the same protein and differ only by one or more conservative missense mutations within the open reading frame of the encoded protein;
- g) a direct sequence comparison may determine two protein-encoding nucleotide sequences to be equivalent if they encode the same protein and differ only by one or more conservative missense mutations anywhere within the open reading frame encoding the protein except for those regions of the open reading frame that encode enzymatic, transmembrane or antigen-recognition domains of the protein;
- h) a direct sequence comparison may determine two protein-encoding nucleotide sequences to be equivalent if they encode the same protein and differ only by one or more silent mutations within the open reading frame;
- i) a direct sequence comparison may determine two protein-encoding nucleotide sequences to be equivalent if they encode the same protein and differ only by the locations of nonsense mutations within the open reading frame that occur within a same domain of the encoded protein;
- j) a direct sequence comparison may determine two protein-encoding nucleotide sequences to be equivalent if they encode the same protein and differ only by the locations of frameshift mutations within the open reading frame that occur within the same respective domain of the encoded protein.

A method and system for genetic attribute analysis can be developed in which non-identical sets of genetic attributes comprising nucleotide sequence are compared to determine whether proteins encoded by those nucleotide sequences are functionally equivalent, and therefore whether genetic information contained in the sets of genetic attributes can be considered to be equivalent (i.e., a match, the same, and/or identical). A determination of equivalence between two or more non-identical yet essentially equivalent sets of genetic attributes can enable the compression of thousands of individual DNA nucleotide attributes into a single categorical genetic attribute assigned to represent those sets of genetic attributes, which is useful for methods such as attribute discovery, predisposition prediction and predisposition modification where a reduction in the amount of genomic data can enhance processing efficiency of the methods. Sets of genetic attributes can be determined to be equivalent based on whether they are able to satisfy one or more equivalence rules (i.e., requirements for equivalence) applied to their comparison. In one embodiment, the equivalence rules can be those listed as (a)-(j) above.

In one embodiment a computer based method for genetic attribute analysis is provided in which a first set of genetic attributes associated with a first individual (or a first group of individuals) comprising a first nucleotide sequence containing an open reading frame encoding a protein can be accessed. A second set of genetic attributes associated with a second individual (or a second group of individuals) comprising a second nucleotide sequence containing the open reading frame encoding the protein can also be accessed, wherein one or more nucleotides of the second nucleotide sequence differ from one or more nucleotides of the first nucleotide sequence. The first nucleotide sequence and the second nucleotide sequence can be compared to identify whether they are equivalent based on one or more equivalence rules for comparison of non-identical protein-encoding nucleotide sequences. A determination indicating that the first set of genetic attributes is identical to the second set of genetic attributes can be generated if the first nucleotide sequence and the second nucleotide sequence were identified to be equivalent, and the generated determination can be stored.

In one embodiment, a determination that two sets of genetic attributes are identical can be a determination assigned to each of the attributes of one set of genetic attributes with respect to their counterpart attributes in the other set. For example, the determination can indicate that the attribute containing the identity of the nucleotide in position 1 of the open reading frame comprised by the first set of genetic attributes is identical to (i.e., a match with) the attribute containing the identity of the nucleotide in position 1 of the open reading frame comprised by the second set of genetic attributes, and so forth for successive attributes representing nucleotides in successive positions of that open reading frame, for both sets of genetic attributes. In one embodiment, the determination is an indicator, flag, marker, or record of a match between two sets of attributes, or between individual attributes of the two sets of attributes. In another embodiment the determination can be one of two possible outcomes of a binary decision regarding whether the two sets of attributes are a match (i.e., equivalent, the same, or identical). In a further embodiment, the two possible outcome choices for a determination of identity or a match between attributes or attribute sets resulting from a comparison involving a binary decision can be, for example, any of the following: yes or no, 1 or 0, match or no match, identical or non-identical, equivalent or not equivalent, and same or different. In one embodiment, the determination can be linked to an attribute combination, a set of attributes, an attribute profile of an individual, a dataset, and/or a record in a database. In one embodiment, the determination can be transmitted to a user, a computer readable memory, a computer readable medium, a database, a dataset, a computer processor, a computer on a network, a visual display, a printout device, a wireless receiver and/or a digital electronic receiver.

Figure 28:
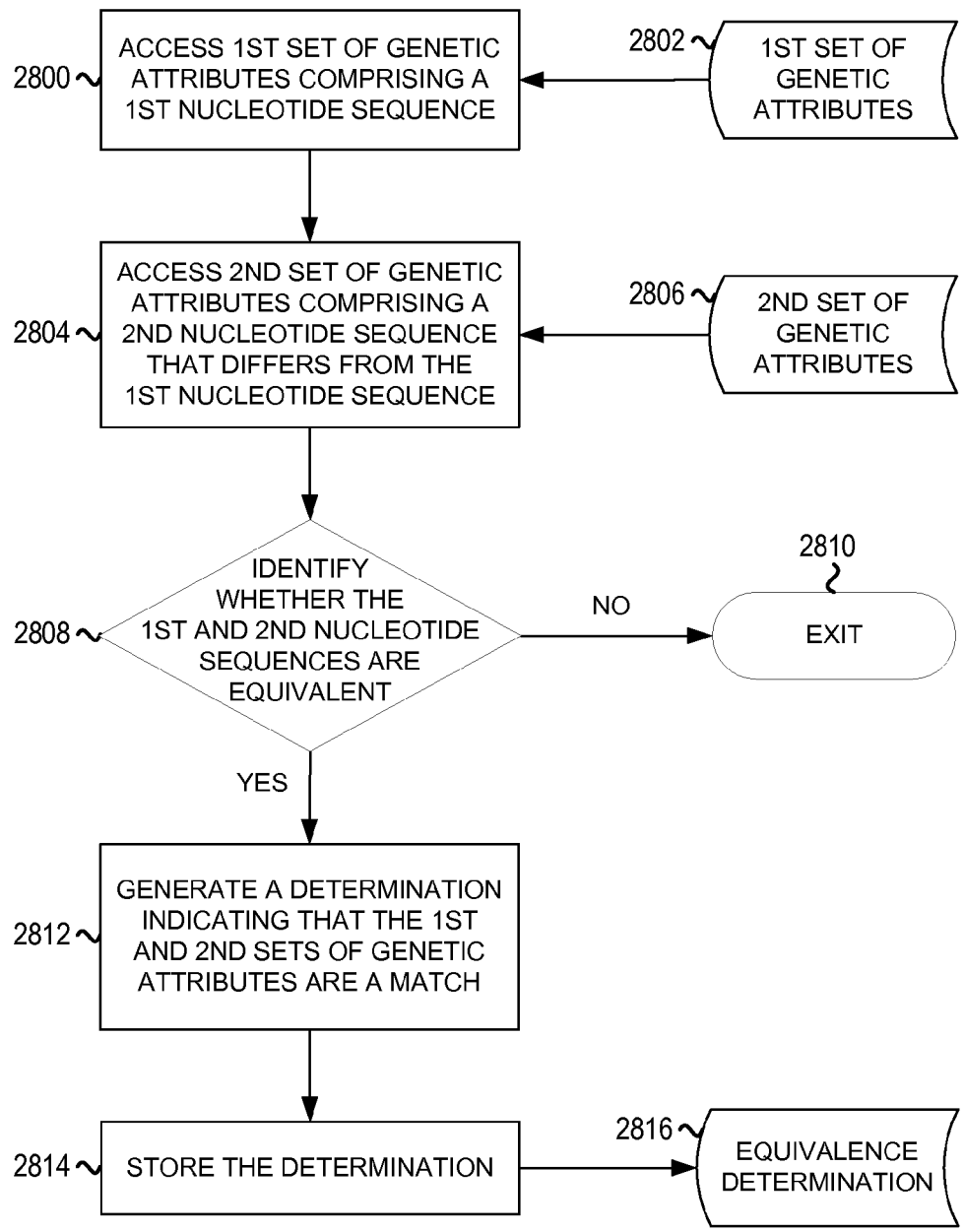
FIG. 28 illustrates a flowchart for a method of genetic attribute analysis.

FIG. 28 illustrates a flow chart for a method of genetic attribute analysis. In access 1st set of genetic attributes comprising a 1st nucleotide sequence step 2800, a 1st set of genetic attributes 2802 associated with an individual and comprising a first nucleotide sequence containing an open reading frame encoding a protein is accessed, for example, in a genetic database. In access 2nd set of genetic attributes comprising a 2nd nucleotide sequence that differs from the 1st nucleotide sequence step 2804, a 2nd set of genetic attributes 2806 associated with one or more individuals and comprising a second nucleotide sequence containing the open reading frame encoding the protein is accessed, wherein one or more nucleotides of the second nucleotide sequence differ from one or more nucleotides of the first nucleotide sequence. In identify whether the 1st and 2nd nucleotide sequences are equivalent step 2808, the first nucleotide sequence and the second nucleotide sequence are compared to identify whether they are equivalent according to one or more equivalence rules for comparison of non-identical nucleotide sequences. If the first and second nucleotide sequences are not identified as being equivalent, then exit step 2810 is executed, at which point the method may be reinitiated using different sets of genetic attributes, for example. If however the first and second nucleotide sequences are identified as being equivalent, then generate a determination indicating that the 1st and 2nd sets of genetic attributes are a match step 2812 is executed to generate a determination that the 1st and 2nd sets of attributes are identical (i.e., equivalent). In store the determination step 2814, the generated determination of a match is stored as equivalence determination 2816.

In one embodiment of a method for genetic attribute analysis, the first set of genetic attributes can comprise an attribute combination associated with the first individual (or a first group of individuals) and the second set of genetic attributes can comprise an attribute combination associated with the second individual (or a second group of individuals). In a further embodiment, an attribute combination can be a selected subset of attributes from a set of genetic attributes, the selection of the subset being performed according to empirical evidence indicating the importance of the subset, results from determinations of subsets based on studies made using full sets of genetic attributes (e.g., whole genome sequence), or other tests, calculations or determinations which provide for the creation of subsets of genetic attributes. In one embodiment, a frequency of occurrence of an attribute combination can be computed for a group of individuals (e.g., a query-attribute-positive or query-attribute-negative groups of individuals) using a determination indicating that two sets of genetic attributes are identical, just as with the identification of identical non-genetic attributes occurring in different sets of attributes (i.e., attribute profiles, or attribute combinations) as described throughout the present disclosure. In one embodiment, a statistical result (e.g., an absolute risk, or a relative risk) indicating the strength of association of an attribute combination with a query attribute can be computed using the determination. In one embodiment, one or more statistical predictions indicating the potential association between the individual and the query attribute can be generated based, at least in part, on the determination.

In one embodiment, the first set of genetic attributes can comprise a portion of an attribute profile associated with a first individual (or a first group of individuals) and the second set of genetic attributes can comprise a portion of an attribute profile associated with a second individual (or a second group of individuals). In a further embodiment, the attribute profile contains only genetic attributes. In an alternative embodiment, the attribute profile can also contain epigenetic, physical, behavioral, and situational attributes, or any combination thereof. In one embodiment a categorical attribute can be generated using the determination, in order to expand an attribute profile of an individual. In a further embodiment, the categorical attribute can be generated as a categorical genetic attribute that can be added, linked and/or associated with the attribute profile in order to expand the attribute profile (or to create a new expanded attribute profile containing only categorical genetic attributes associated with the individual or group of individuals).

Similarly, a system can be developed which comprises a first data accessing subsystem for accessing a first set of genetic attributes associated with a first individual (or a first group of individuals) comprising a first nucleotide sequence containing an open reading frame encoding a protein; a second data accessing subsystem for accessing a second set of genetic attributes associated with a second individual (or a second group of individuals) comprising a second nucleotide sequence containing the open reading frame encoding the protein, wherein one or more nucleotides of the second nucleotide sequence differ from one or more nucleotides of the first nucleotide sequence; a data processing subsystem comprising (i) a data comparison subsystem for identifying whether the first nucleotide sequence and the second nucleotide sequence are equivalent based on an equivalence rule for comparison of non-identical nucleotide sequences, and (ii) a data generating subsystem for generating a determination indicating that the first set of genetic attributes associated with the first individual is identical to the second set of genetic attributes associated with the second individual, if the first nucleotide sequence and the second nucleotide sequence were identified to be equivalent; a data storage subsystem for storing the determination; and a communications subsystem for transmitting the determination to a user, a computer readable memory, a computer readable medium, a database, a dataset, a computer processor, a computer on a network, a visual display, a printout device, a wireless receiver and/or a digital electronic receiver. The various subsystems can be discrete components, configurations of electronic circuits within other circuits, software modules running on computing platforms including classes of objects and object code, or individual commands or lines of code working in conjunction with one or more Central Processing Units (CPUs). Various storage units can be used including but not limited to electronic, magnetic, electromagnetic, optical, opto-magnetic and electro-optical storage.

In one application the method and/or system is used in conjunction with one or more databases, such as those that would be maintained by health-insurance providers, employers, or health-care providers, which can serve to store the aforementioned sets of genetic attributes, attribute profiles, attribute combinations, frequencies of occurrence, corresponding statistical results, datasets, database records, categorical attributes, equivalence rules and determinations. In one embodiment the equivalence determinations are stored separately (i.e., in a separate dataset) from attributes or sets of genetic attributes and the correspondence is achieved using identifiers, links or keys present in or shared between them (i.e., across datasets). In one embodiment, sets of genetic attributes can be either stored together with other attribute data (e.g., an attribute profile) for an individual or groups of individuals, or can be stored separately from other attribute data as in a dedicated genetic attribute database, human genome database or genetic data repository. In one embodiment, attribute combinations and corresponding statistical results data can be stored together with other attribute data. In another embodiment, attribute combinations and corresponding statistical results can be stored separately from each other and/or separately from other attribute data. A user, such as a clinician, physician or patient, can input a query attribute for determining whether sets of genetic attributes are equivalent, and the determination can then form the basis for identifying attributes that co-occur with other query attributes in certain individuals (e.g., attribute combinations that segregate with query-attribute-positive individuals) and for use in methods of attribute combination database creation, attribute discovery, attribute prediction, side effect prediction, and predisposition (i.e., destiny) modification.

In biological organisms and systems, age and sex type are two somewhat unique and powerful attributes that influence the expression of many other attributes. For example, age is a primary factor associated with: predicting onset and progression of age-associated diseases in humans and animals; acquiring training and life experiences that lead to success in career, sports and music; and determining life-style choices. Similarly, biological sex type is correlated with profound differences in expression of physical, behavioral and situational attributes. The inclusion of accurate data for the age and sex of individuals is very important for acquiring accurate and valid results from the methods of the present invention. In one embodiment, specific values of age and sex that aggregate with a query attribute can be determined by the methods of the present invention, just as for other attributes, to either co-occur or not co-occur in attribute combinations that are associated with a query attribute. In one embodiment results of the methods can be filtered according to age and/or sex. In other embodiments a population or subpopulation can be selected according to age and/or sex (age-matching and/or sex-matching) and then only that subpopulation subjected to additional processing by methods of the present invention. In another embodiment, an age-matched and/or sex-matched population may be used to form query-attribute-positive and query-attribute-negative groups. In another embodiment, the sex and/or age of an individual is used to select a population of age-matched and/or sex-matched individuals for creation of an attribute combinations database. In another embodiment, the sex and/or age of an individual is used to select a subpopulation of age-matched and/or sex-matched individuals for comparison in methods of identifying predisposing attribute combinations, individual predisposition prediction and individual destiny modification. In another embodiment, summary statistics for age and/or sex are included with the output results of the methods. In another embodiment, summary statistics for age and/or sex are included with the output results of the methods when other attributes are omitted or masked for privacy.

Additional embodiments are envisioned which implement a preselection of individuals processed by methods of the present invention. In one embodiment, preselection is a selection or pooling of one or more populations or subpopulations of individuals from one or more datasets or databases based on particular values of attributes such as income, occupation, disease status, zip code or marital status for example. Preselecting populations and subpopulations based on possession of one or more specified attributes can serve to focus a query on the most representative population, reduce noise by removing irrelevant individuals whose attribute data may contribute to increasing error in the results, and decrease computing time required to execute the methods by reducing the size of the population to be processed. Also, using preselection to define and separate different populations enables comparison of predisposing attribute combinations toward the same query attribute between those populations. For example, if two separate subpopulations are selected—a first population of individuals that earn over $100,000/year and a second population of individuals that earn less that $10,000/year—and each subpopulation is processed separately to identify predisposing attribute combinations for a query attribute of alcoholism, a comparison of the identities, frequencies of occurrence, and strengths of association of predisposing attribute combinations that lead to alcoholism in individuals that earn over $100,000 can be made with those of individuals that earn less than $10,000. In one embodiment, predisposing attribute combinations that are present in one preselected population and absent in a second preselected population are identified. In one embodiment, the frequencies of occurrence and/or statistical strengths of association of predisposing attribute combinations are compared between two or more preselected populations. In one embodiment, only a single preselected population is selected and processed by the methods of the present invention.

Additional embodiments of the methods of the present invention are possible. In one embodiment, two or more mutually exclusive (having no attributes in common) predisposing attribute combinations for a query attribute are identified for a single individual and can be tabulated and presented as output. In one embodiment the query attribute can be an attribute combination, and can be termed a query attribute combination. By submitting a query attribute combination to the methods of the present invention, the ability to identify attribute combinations that predispose toward other attribute combinations is enabled.

In one embodiment of the methods of the present invention, statistical measures for strength of association of attribute combinations are not stored in a dataset containing the attribute combinations, but rather, are calculated at any time (on as-needed basis) from the frequencies of occurrence of the stored attribute combinations. In one embodiment only a portion of the results from a method of the present invention are presented, reported or displayed as output. In one embodiment, the results may be presented as a graphical display or printout including but not limited to a 2-dimensional, 3-dimensional or multi-dimensional axis, pie-chart, flowchart, bar-graph, histogram, cluster chart, dendrogram, tree or pictogram.

Methods for predisposing attributes identification, predisposition prediction and intelligent destiny modification are subject to error and noise. A prominent cause of error and noise in methods is bias in the attribute data or in the distribution of the population from which the data is collected. In one embodiment, bias can manifest as inaccurate frequencies of occurrence and strengths of association between attribute combinations and query attributes, inaccurate lists of attributes determined to co-occur with a query attribute, inaccurate predictions of an individual's predisposition toward query attributes, and inaccurate lists of modifiable attributes for destiny modification. Bias can result from inaccurate data supplied to methods of the present invention, primarily as a consequence of inaccurate reporting and self-reporting of attribute data but also as a consequence of collecting attributes from populations that are biased, skewed or unrepresentative of the individual or population for which predisposition predictions are desired. Error can also result as consequence of faulty attribute data collection such as misdirected or improperly worded questionnaires.

If bias exists and is left unchecked, it can have different effects depending on whether the bias exists with the query attribute, or whether the bias exists in one or more of the co-occurring attributes of an attribute combination. At a minimum, the existence of bias in the attribute data or population distribution may result in slightly inaccurate results for frequency of occurrence of attributes and attribute combinations, and inaccurate statistical strengths of association between attribute combinations and query attributes. When bias is present at higher levels, results for frequency of occurrence and strengths of association can be moderately to highly inaccurate, even producing false positives (Type I Error) and false negatives (Type II Error), where a false positive is the mistaken identification of an attribute association that actually does not exist (or does not exist differentially in one population relative to another) and a false negative is a failure to identify an attribute association that actually does exist (or exists differentially in one population relative to another).

For the methods disclosed herein, it is possible to minimize error and noise by ensuring that accurate (unbiased) attribute data are provided to the methods and that representative populations of individuals are used as the basis for creating attribute combination databases. It is anticipated that some degree of inaccuracy of input data will be present. The following disclosure indicates sources of error and noise and ways to identify, avoid and compensate for inaccurate attribute data and unrepresentative populations.

Selection bias is a major source of error and refers to bias that results from using a population of individuals that are not representative of the population for which results and predictions are desired. For example, if a query for attribute combinations that predispose an individual to becoming a professional basketball player is entered against an attributes combination dataset that was created with an over-representation of professional basketball players relative to the general population, then smaller attribute combinations that are associated with both professional basketball players and individuals that are not professional basketball players will receive artificially inflated statistical strengths of association with the query attribute, giving a false impression that one needs fewer predisposing attributes than are actually required to achieve the goal with a high degree of probability. Selection bias is largely under the control of those responsible for collecting attribute profiles for individuals of the population and creating datasets that contain that information. Selecting a misrepresentative set of individuals will obviously result in selection bias as discussed above. Sending questionnaires to a representative set of individuals but failing to receive completed questionnaires from a particular subpopulation, such as a very busy group of business professionals who failed to take time to fill out and return the questionnaire, will also result in selection bias if the returned questionnaires are used to complete a database without ensuring that the set of responses are a balanced and representative set for the population as a whole. Therefore, in one embodiment, administrators of the methods disclosed herein use a variety of techniques to ensure that appropriate and representative populations are used so that selection bias is not present in the attribute profiles and attribute combination datasets used as input data for the methods.

Information bias is the second major class of bias and encompasses error due to inaccuracies in the collected attribute data. The information bias class comprises several subclasses including misclassification bias, interview bias, surveillance bias, surrogate interview bias, recall bias and reporting bias.

Misclassification bias refers to bias resulting from misclassifying an individual as attribute-positive when they are attribute-negative, or vice-versa. To help eliminate this type of bias, it is possible to assign a null for an attribute in circumstances where an accurate value for the attribute cannot be ensured.

Interview bias refers to bias resulting from deriving attributes from questions or means of information collection that are not correctly designed to obtain accurate attribute values. This type of bias is primarily under the control of those administrators that design and administer the various modes of attribute collection, and as such, they can ensure that the means of attribute collection employed are correctly designed and validated for collecting accurate values of the targeted attributes.

Surveillance bias refers to bias that results from more closely or more frequently monitoring one subpopulation of individuals relative to others, thereby resulting in collection of more accurate and/or more complete attribute data for that subpopulation. This is common in cases of individuals suffering from disease, which results in their constant and close monitoring by experienced professionals who may collect more accurate and more complete attribute data about many aspects of the individual, including trivial, routine and common attributes that are not restricted to the medical field. An administrator of the methods disclosed herein can seek to reduce this bias by either excluding attribute information obtained as a consequence of surveillance bias or by ensuring that equivalent attribute information is provided for all members of the representative population used for the methods.

Surrogate interview bias refers to bias that results from obtaining inaccurate attribute information about an individual from a second-hand source such as a friend or relative. For example, when an individual dies, the only source of certain attribute information may be from a parent or spouse of the individual who may have inaccurate perception or memory of certain attributes of the deceased individual. To help avoid this type of bias, it is preferable that a surrogate provider of attribute information be instructed to refrain from providing attribute values for which they are uncertain and instead assign a null for those attributes.

Recall bias refers to enhanced or diminished memory recall of attribute values in one subpopulation of individuals versus another. This again may occur in individuals that are subject to extreme situations such as chronic illness, where the individual is much more conscious and attentive to small details of their life and environment to which others would pay little attention and therefore not recall as accurately. This type of bias results from inaccuracy in self-reporting and can be difficult to detect and control for. Therefore, to minimize this type of bias, it is recommended that attempts to collect self-reported data be made over a period of time in which individuals are aware of attributes that are being collected and may even keep a record or journal for attributes that are subject to significant recall bias. Also, whenever more accurate means than self-reporting can be used to collect attribute values, the more accurate means should be used.

Reporting bias refers to bias resulting from intentional misrepresentation of attribute values. This occurs when individuals underestimate the value for an attribute or underreport or fail to report an attribute they perceive as undesirable or are in denial over, or alternatively, when they overestimate the value for an attribute or overreport or invent possession of an attribute they perceive as desirable. For example, individuals typically knowingly underestimate the quantity of alcohol they drink, but overestimate the amount of time they spend exercising. One approach to encourage accurate self-reporting of attribute values can be to allow the individual to control their attribute profile record and keep their identity masked or anonymous in results output or during use of their data by others, when creating attribute combinations databases for example. If bias can be determined to exist and quantified at least in relative terms, another approach can be to use mathematical compensation/correction of the attribute value reported by the individual by multiplying their reported value by a coefficient or numerical adjustment factor in order to obtain an accurate value. In one embodiment this type of adjustment can be performed at the time the data is collected. In another embodiment this type of adjustment can be performed during conversion and reformatting of data by data conversion/formatting engine 220.

In one embodiment data conversion/formatting engine 220 works toward the removal of biases by the application of rules which assist in the identification of biased (suspect) attributes. In one embodiment the rules cause the insertion of null attributes where the existing attribute is suspect. In an alternate embodiment, rules are applied to identify suspect attributes (e.g. overreporting of exercise, underreporting of alcohol consumption) and corrective factors are applied to those attributes. For example, if it is determined that users self report consumption of alcohol at about ⅓ the actual rate consumed, the rules can, when attributes are suspect, increase the self-reported attribute by a factor of 1.5-3.0 depending on how the attribute is believed to be suspect. In large databases (e.g. health care databases) the size of the database can be used in conjunction with specific investigations (detailed data collection on test groups) to help develop rules to both identify and address biases.

In an alternate embodiment, actual possession of attributes and accurate values for self-reported attributes are determined using a multipronged data collection approach wherein multiple different inquires or means of attribute collection are used to collect a value for an attribute prone to bias. One example of this approach is to employ a questionnaire that asks multiple different questions to acquire the same attribute value. For example, if one wants to collect the attribute value for the number of cigarettes a person smokes each week, a questionnaire can include the following questions which are designed to directly or indirectly acquire this information: "how many cigarettes do you smoke each day?", "how many packs of cigarettes do you smoke each day?", "how many packs of cigarettes do you smoke each week?", "how many packs of cigarettes do purchase each day?, each week?", "how many cartons of cigarettes do you purchase each month?", "how much money do you spend on cigarettes each day?, each week? each month?", "how many smoking breaks do you take at work each day?". Another example is to ask a person to self-report how much time they spend exercising and also collect information from their gym that shows the time they swipe-in and swipe-out with their membership card. In this way, multiple sources of values for an attribute can be obtained and the values compared, cross-validated, deleted, filtered, adjusted, or averaged to help ensure storing accurate values for attributes.

In one embodiment the comparison, cross-validation, deletion, filtering, adjusting and averaging of attribute values can be performed during conversion and reformatting of data by data conversion/formatting engine 220. In one embodiment, multiple values obtained for a single attribute are averaged to obtain a final value for the attribute. In one embodiment, values for an attribute are discarded based on discrepancies between multiple values for an attribute. In one embodiment, one value for an attribute is chosen from among multiple values obtained for the attribute based on a comparison of the multiple values. In an alternate embodiment, reported values that appear out of an acceptable range (e.g. statistical outliers) are discarded and the final attribute value is determined from the remaining reported values.

Although calculation of the following mathematical measures are not performed in the examples presented herein, statistical measures of confidence including but not limited to variance, standard deviation, confidence intervals, coefficients of variation, correlation coefficients, residuals, t values (e.g., student's t test, one- and two-tailed t-distributions), ANOVA, correlation coefficients (e.g., regression coefficient, Pearson product-moment correlation coefficient), standard error and p-values can be computed for the results of methods of the current invention, the computation of which is known to those of skill in the art. In one embodiment, these confidence measures provide a level or degree of confidence in the numerical results of the methods so that the formal, standardized, legal, ethical, business, economic, medical, scientific, or peer-reviewable conclusions and decision-making can be made based on the results. In another embodiment, these measures are computed and compared for frequencies of occurrence of attribute combinations during creation of an attribute combinations database, for example to determine whether the difference between frequencies of occurrence of an attribute combination for the query-attribute-positive and query-attribute-negative groups is statistically significant for the purpose, in a further embodiment, of eliminating those attribute combinations that do not have a statistically significant difference in frequency of occurrence between the two populations. Levels of significance and confidence thresholds can be chosen based on user preference, implementation requirements, or standards of the various industries and fields of application.

Aside from the purposes indicated in the above methods, the present invention can also be used for investigation of attribute interactions forming the basis for predisposition. For example, embodiments of the methods can be used to reveal which attributes have diverse and wide-ranging interactions, which attributes have subtle interactions, which attributes have additive effects and which attributes have multiplicative or exponential synergistic interactions with other attributes.

In one embodiment, synergistic interactions are particularly important because they have multiplicative or exponential effects on predisposition, rather than simple additive effects, and can increase predisposition by many fold, sometimes by as much as 1000 fold. These types of synergistic interactions are common occurrences in biological systems. For example, synergistic interactions routinely occur with drugs introduced into biological systems. Depending on the circumstances, this synergism can lead to beneficial synergistic increases in drug potency or to synergistic adverse drug reactions. Synergism also occurs in opportunistic infections by microbes. Synergism between attributes may also occur in development of physical and behavioral traits. For example, cigarette smoking and asbestos exposure are known to synergize in multiplicative fashion to cause lung cancer. The same is true for smoking combined with uranium radiation exposure. Exposure to bacterial aflatoxin ingested via farm products combined with chronic hepatitis B infection synergistically causes liver cancer. Revealing synergistic interactions can be invaluable for intelligent and efficient targeting of therapies, treatments, training regimens, and lifestyle alterations to either increase or decrease predisposition toward an attribute of interest in the most rapid and efficient manner.

FIG. 29A is a representative example of a 3rd dataset resulting from the method for destiny modification to determine predisposition of individual #1 of FIG. 14 toward attribute 'W'. In contrast, FIG. 29B is a representative example of a 3rd dataset for individual #1 resulting from the method for destiny modification to determine predisposition toward attribute 'W' following elimination of attribute 'A' from their attribute profile. By comparing the two datasets, a before and after look at the predisposition of individual #1 toward having or developing attribute 'W' is provided, where 'before' refers to the situation in which attribute 'A' is still associated with the individual and 'after' refers to the situation in which attribute 'A' is no longer associated with the individual. From a comparison of these results, not only is the magnitude of attribute 'A' contribution toward predisposition revealed, but synergistic interactions of other attributes with attribute 'A' are also revealed.

In the 'before' situation shown in FIG. 29A, the individual possesses the attribute combination ACE. Addition of association to either attribute I, K or Q alone increases absolute risk to 1.0. However, in the 'after' situation of FIG. 29B where the individual begins with the combination CE, adding association to either attribute I, K or Q alone has little or no positive effect on predisposition. This reveals that I, K and Q require synergism with A to contribute significantly toward predisposition to query attribute W in this example. Furthermore, addition of a combination of IQ or IK still has no positive effect on predisposition in the absence of A. This indicates that I can synergize with A but not with Q or K. Interestingly, when the combination KQ is added to the combination CE in the absence of A, absolute risk jumps to 1.0. This indicates that K and Q can synergize with each other in the presence of CE, effectively increasing predisposition to a maximum even in the absence of attribute A.

In the various embodiments of the present invention, the question as to how the results are to be used can be considered in the application of a particular embodiment of the method of attribute identification. In instances where the goal is to determine how to reduce predisposition toward an undesirable attribute for example, then utilizing one embodiment of the method to determine the identity of predisposing attribute combinations and then proceeding to eliminate an individual's association with those attributes is one way to reduce predisposition toward that attribute. However, one may also attempt to decrease predisposition by applying an embodiment of the method to determine those attribute combinations that are predisposing toward an attribute that is the opposite of the undesirable attribute, and then proceed to introduce association with those attributes to direct predisposition of the individual toward that opposing attribute. In other words, the attributes that predispose toward a key attribute may in many cases not be simple opposite of attributes that predispose to the opposite of the key attribute. Approaching this from both angles may provide additional effectiveness in achieving the goal of how to most effectively modify predisposition toward a key attribute of interest. In one embodiment both approaches are applied simultaneously to increase success in reaching the goal of destiny modification.

Confidentiality of personal attribute data can be a major concern to individuals that submit their data for analysis. Various embodiments of the present invention are envisioned in which the identity of an individual linked directly or indirectly to their data, or masked, or provided by privileged access or express permission, including but not limited to the following embodiments. In one embodiment the identity of individuals are linked to their raw attribute profiles. In one embodiment the identity of individuals are linked directly to their raw attribute profiles. In one embodiment the identity of individuals are linked indirectly to their raw attribute profiles. In one embodiment the identity of individuals are anonymously linked to their raw attribute profiles. In one embodiment the identity of individuals are linked to their raw attribute profiles using a nondescriptive alphanumeric identifier. In one embodiment the identity of individuals are linked to the attribute combinations they possess as stored in one or more datasets of the methods. In one embodiment the linkage of identity is direct. In one embodiment the linkage of identity is indirect. In one embodiment the linkage of identity requires anonymizing or masking the identity of the individual. In one embodiment the linkage of identity requires use of a nondescriptive alphanumeric identifier.

Various embodiments of the present invention are envisioned in which data is made public, or held private, or provided restricted/privileged access granted upon express permission and include but are not limited to the following embodiments. In one embodiment, the identity of attributes and statistical results produced in the output of the methods are provided only to the individual whose attribute profile was accessed for the query. In one embodiment, the identity of attributes and statistical results produced in the output of the methods are provided only to the individual that submitted or authorized the query. In one embodiment, the identity of attributes and statistical results produced in the output of the methods are provided only to the individual consumer that paid for the query. In one embodiment, the identity of attributes and statistical results produced in the output of the methods are provided only to a commercial organization that submitted, authorized or paid for the query. In one embodiment, the identities of attributes in the output results from methods of the present invention are omitted or masked. In one embodiment, the identity of attributes can be omitted, masked or granted privileged access to by others as dictated by the individual whose attribute profile was accessed for the query. In one embodiment, the identity of attributes can be made accessible to a government employee, legal professional, medical professional, or other professional legally bound to secrecy. In one embodiment, the identity of attributes can be omitted, masked or granted privileged access to by others as dictated by a government employee, legal professional, or medical professional. In one embodiment, the identity of attributes can be omitted, masked or granted privileged access to by others as dictated by a commercial organization.

Figure 30:
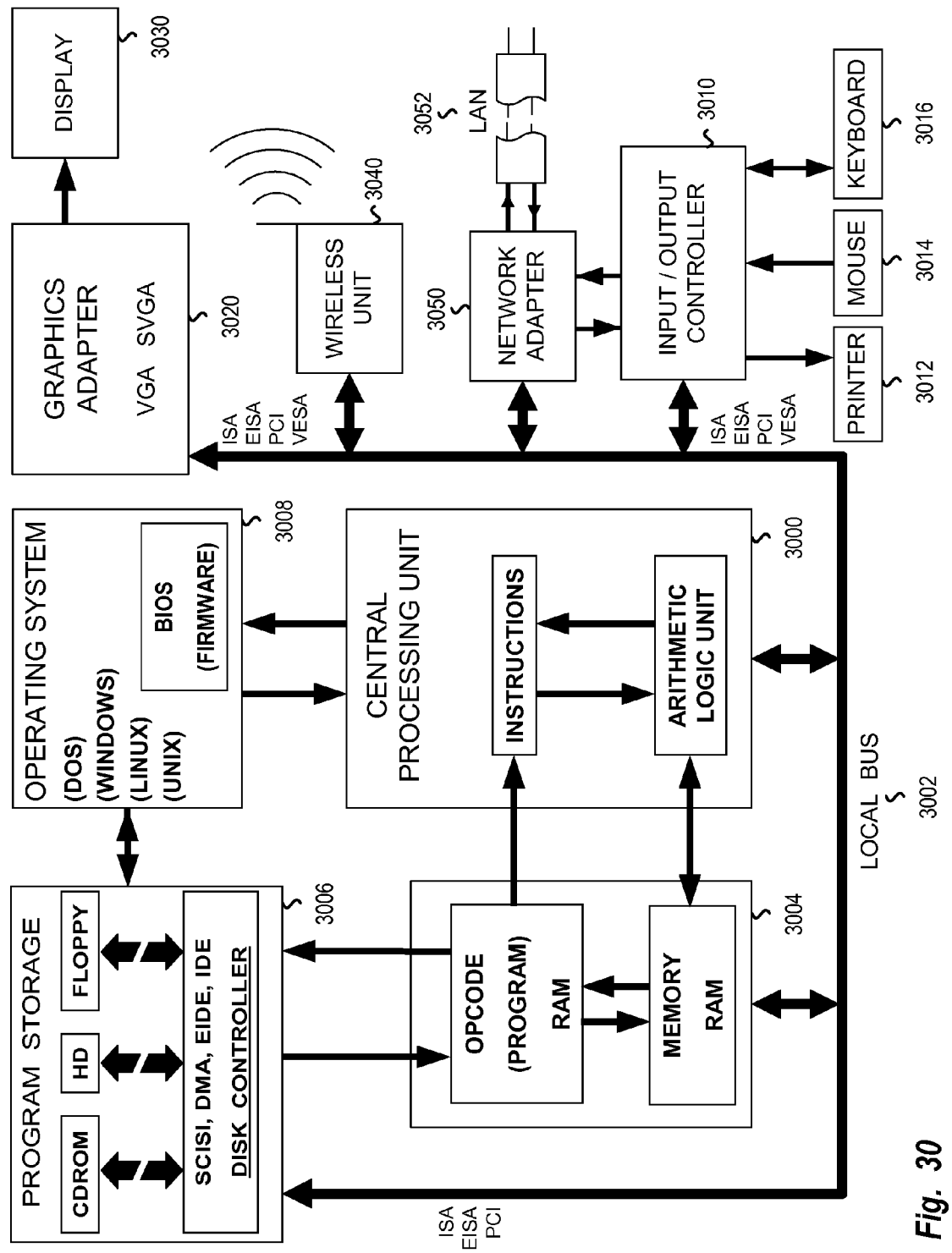
FIG. 30 illustrates one embodiment of a computing system on which the present method and system can be implemented.

FIG. 30 illustrates a representative computing system on which embodiments of the present method and system can be implemented. With respect to FIG. 30, a Central Processing Unit (CPU) 3000 is connected to a local bus 3002 which is also connected to Random Access Memory (RAM) 3004 and disk controller and storage system 3006. CPU 3000 is also connected to an operating system including BIOS 3008 which contains boot code and which can access disk controller and storage system 3006 to provide an operational environment and to run an application (e.g. attribute determination). The representative computing system includes a graphics adaptor 3020, display 3030, a wireless unit 3040 (i.e., a data receiver/transmitter device), a network adapter 3050 that can be connected to a LAN 3052 (local area network), and an I/O controller 3010 that can be connected to a printer 3012, mouse 3014, and keyboard 3016.

It will be appreciated by one of skill in the art that the present methods, systems, software and databases can be implemented on a number of computing platforms, and that FIG. 30 is only a representative computing platform, and is not intended to limit the scope of the claimed invention. For example, multiprocessor units with multiple CPUs or cores can be used, as well as distributed computing platforms in which computations are made across a network by a plurality of computing units working in conjunction using a specified algorithm. The computing platforms may be fixed or portable, and data collection can be performed by one unit (e.g. a handheld unit) with the collected information being reported to a fixed workstation or database which is formed by a computer in conjunction with mass storage. Similarly, a number of programming languages can be used to implement the methods and to create the systems disclosed herein, those programming languages including but not limited to C, Java, php, C++, perl, visual basic, sql and other languages which can be used to cause the representative computing system of FIG. 30 to perform the steps disclosed herein.

Figure 31:
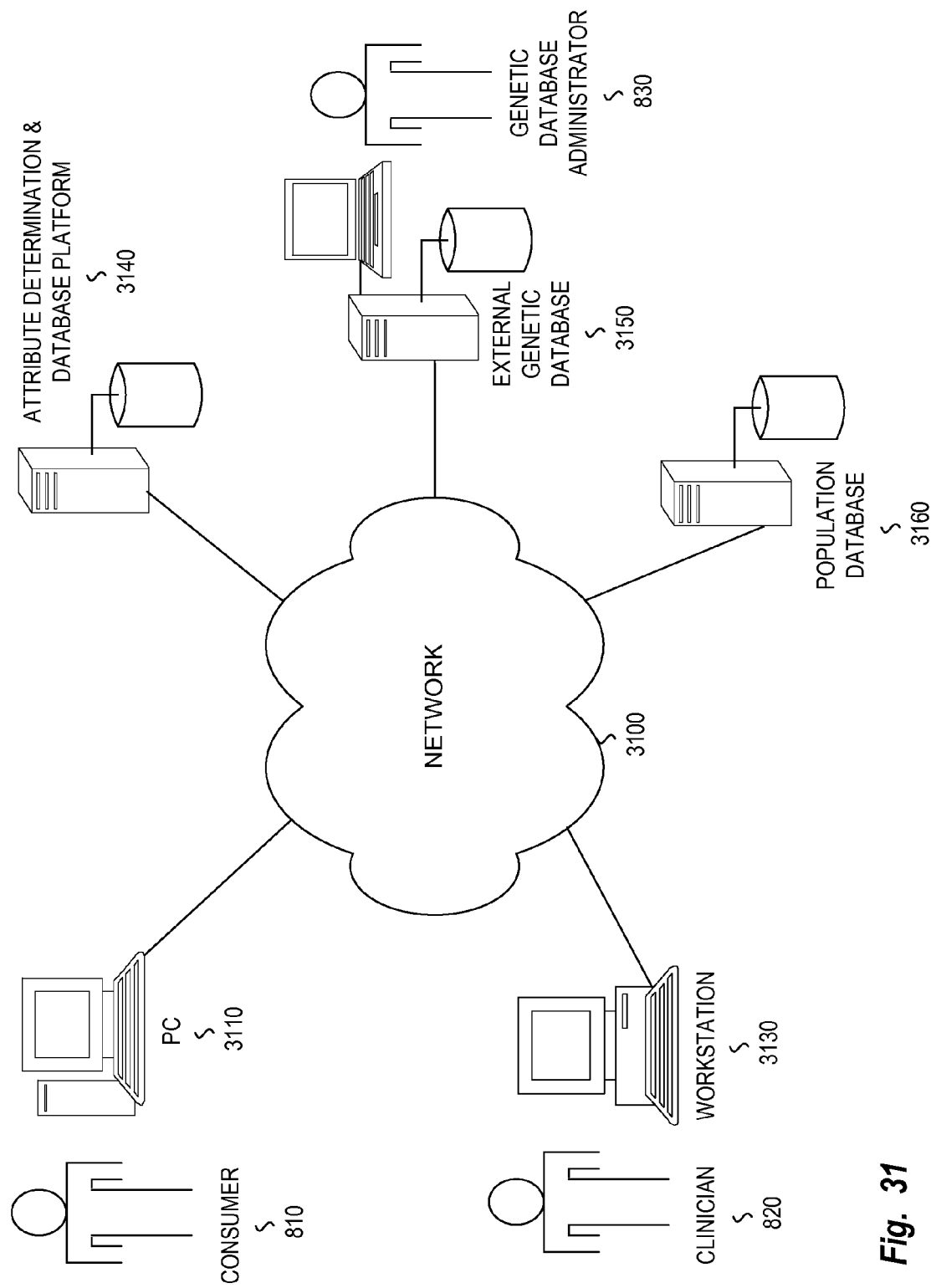
FIG. 31 illustrates a representative deployment diagram for an attribute determination system.

With respect to FIG. 31, the interconnection of various computing systems over a network 3100 to realize an attribute determination system 800, such as that of FIG. 8, is illustrated. In one embodiment, consumer 810 uses a Personal Computer (PC) 3110 to interface with the system and more specifically to enter and receive data. Similarly, clinician 820 uses a workstation 3130 to interface with the system. Genetic database administrator 830 uses an external genetic database 3150 for the storage of genetic/epigenetic data for large populations. Historical, situational, and behavioral data are all maintained on population database 3160. All of the aforementioned computing systems are interconnected via network 3100.

In one embodiment, and as illustrated in FIG. 31, an attribute determination computing and database platform 3140 is utilized to host the software-based components of attribute determination system 800, and data is collected as illustrated in FIG. 8. Once relevant attributes are determined, they can be displayed to consumer 810, clinician 820, or both. In an alternate embodiment, the software-based components of attribute determination system 800 can reside on workstation 3130 operated by clinician 820. Genetic database administrator 830 may also maintain and operate attribute determination system 800 and host its software-based components on external genetic database 3150. Another embodiment is also possible in which the software-based components of the attribute determination system 800 are distributed across the various computing platforms. Similarly, other parties and hosting machines not illustrated in FIG. 31 may also be used to create attribute determination system 800.

In one embodiment, the datasets of the methods of the present invention may be combined into a single dataset. In another embodiment the datasets may be kept separated. Separate datasets may be stored on a single computing device or distributed across a plurality of devices. As such, a memory for storing such datasets, while referred to as a singular memory, may in reality be a distributed memory comprising a plurality of separate physical or virtual memory locations distributed over a plurality of devices such as over a computer network. Data, datasets, databases, methods and software of the present invention can be embodied on a computer-readable media (medium), computer-readable memory (including computer readable memory devices), and program storage devices readable by a machine.

In one embodiment, at least a portion of the attribute data for one or more individuals is obtained from medical records. In one embodiment, at least a portion of the attribute data for one or more individuals is accessed, retrieved or obtained (directly or indirectly) from a centralized medical records database. In one embodiment, at least a portion of the attribute data for one or more individuals is accessed or retrieved from a centralized medical records database over a computer network.

The methods, systems, software and databases disclosed herein have a number of industrial applications pertaining to the identification of attributes and combinations of attributes related to a query attribute; creation of databases containing the attributes, attribute combinations, strength of association with the query attribute, and rankings of strength of association with the query attribute; and use of the identified attributes, combinations of attributes, and strength of association of attributes with the query attribute in making a variety of decisions related to lifestyle, lifestyle modification, diagnosis, medical treatment, eventual outcome (e.g. destiny), possibilities for destiny modification, and sensitivity analysis (impact of modification of certain attributes).

In one embodiment the methods, system, software, and databases disclosed herein are used as part of a web based health analysis and diagnostics system in which one or more service providers utilize pangenetic information (attributes) in conjunction with physical, situational, and behavioral, attributes to provide services such as longevity analysis, insurance optimization (determination of recommended policies and amounts), and medication impact analysis. In these scenarios, the methods disclosed herein are applied using appropriate query attributes to determine such parameters as the likelihood that the patient will develop or has a particular disease, or make an inquiry related to likelihood of disease development. In one embodiment, the genetic sample is mailed to an analysis center, where genetic and epigenetic sequencing is performed, and the data stored in an appropriate database. Clinician 820 of FIG. 8 or consumer 810 of FIG. 8 provides for reporting of other data from which physical, situational, and behavioral attributes are developed and stored. A query related to a diagnosis can be developed by clinician 820 (or other practitioner) and submitted via the web. Using the methods and algorithms disclosed herein, a probable diagnosis or set of possible diagnoses can be developed and presented via the web interface. These diagnoses can be physical or mental. With respect to the diagnosis of mental illnesses (mental health analyses), identification of key behavioral and situational attributes (e.g. financial attributes, relationship attributes) which may affect mental health is possible using the present methods, systems, software and databases. Risk assessments can be performed to indicate what mental illnesses consumer 810 may be subject to, as well as suggesting modifications to behavior or living environment to avoid those illnesses. For example, a consumer subject to certain types of obsessive disorders might be advised to change certain behavioral and/or situational attributes which are associated with that obsessive disorder, thus decreasing the probability that they will have or exacerbate that disorder.

With respect to general analysis of medical conditions, the web based system can be used to evaluate insurance coverage (amounts and types) and provide recommendations for coverage based on the specific illness risks and attributes possessed by the consumer, evaluate the impact (or lack thereof) of lifestyle changes, the impact and effectiveness of medications. Such analyses can also be made in view of predisposition predictions that can indicate probable future development of a disorder, thereby allowing preparations for insurance coverage and therapeutic preventive measures to be taken in advance of the disorder.

As previously discussed, the system can be used for web based strength and weakness identification, by allowing the consumer or clinician to query the system to assess the probability that an individual has a particular strength or weakness. In one embodiment, parents query the system to determine if their child (from which a biological sample was taken) will have particular strengths (e.g. music or sports) and what behavioral attributes should be adopted to maximize the probability of success at that endeavor, assuming a "natural talent" can be identified through the combinations of attributes associated with that endeavor. Various service providers, including genetic and epigenetic profiling entities, can interact with the system over a network (e.g., the internet) and allow the consumer or clinician to interact with the system over a network through a web-based interface to obtain the destiny or attribute information.

In one embodiment a web based goal achievement tool is presented in which the consumer enters one or more goals, and the system returns modifiable attributes which have been identified using the aforementioned analysis tools, indicating how the consumer can best obtain the desired goal(s) given their pangenetic, physical, situational, and behavioral makeup.

In one embodiment, potential relationship/life/marriage partners are located based on the pangenetic, physical, situational, and behavioral attributes of those individuals, as measured against an attribute model of a suitable partner developed for the consumer. The attribute model of the suitable partner can be developed using a number of techniques, including but not limited to, modeling of partner attributes based on attributes of individuals with which the individual has had previous successful relationships, determination of appropriate "complementary" attributes to the consumer based on statistical studies of individuals with similar attributes to the consumer who are in successful relationships and examination of their partner's attributes (determination of appropriate complementary attributes), and an ab initio determination of appropriate partner attributes. Once the attribute model for the most suitable potential partner has been developed, a database containing pangenetic, physical, situational and behavioral attribute data for potential partners for the consumer can be searched for the purpose of partner identification. In an alternate embodiment a consumer indicates persons they believe have suitable partner qualities including physical attraction (based on photos or video segments) as well as attributes described in profiles associated with the persons and their photos. In one embodiment the system uses genetic and epigenetic information associated with those individuals to create a subpopulation of individuals which the consumer believes they are attracted to, and examines a variety of data associated with that subpopulation (e.g., all available attribute data including genetic and epigenetic data) to determine attributes that are indicative of desirability to that consumer. In one embodiment the system uses those attributes to locate more individuals that could be potentially of interest to the consumer and presents those individuals to the consumer as potential partners.

Although the aforementioned methods, systems, software and databases have been disclosed as incorporating and utilizing pangenetic, physical, situational and behavioral data, embodiments not utilizing pangenetic information are possible, with those embodiments being based solely on physical, situational and behavioral data. Such embodiments can be utilized to accomplish the tasks disclosed above with respect to the analysis of biological systems, as well as for the analysis of complex non-living systems which contain a multitude of attributes. As an example, a non-biological application of the methodology and systems disclosed herein would be for the analysis of complex electrical or electrical-mechanical systems in order to identify probable failure mechanisms (e.g. attributes leading to failure) and as such increase reliability through the identification of those failure-associated attributes. Additionally, the aforementioned embodiments are based on the use of information from multiple attribute categories. Embodiments in which attribute information from a single attribute category (pangenetic, behavioral, physical, or situational) can be used in circumstances where attributes from a single category dominate in the development of a condition or outcome.

Embodiments of the present invention can be used for a variety of methods, databases, software and systems including but not limited to: pattern recognition; feature extraction; binary search trees and binary prediction tree modeling; decision trees; neural networks and self-learning systems; belief networks; classification systems; classifier-based systems; clustering algorithms; nondeterministic algorithms (e.g., Monte Carlo methods); deterministic algorithms; scoring systems; decision-making systems; decision-based training systems; complex supervised learning systems; process control systems; chaos analysis systems; interaction, association and correlation mapping systems; relational databases; navigation and autopilot systems; communications systems and interfaces; career management; job placement and hiring; dating services; marriage counseling; relationship evaluation; animal companion compatibility evaluation; living environment evaluation; disease and health management and assessment; genetic assessment and counseling; genetic engineering; genetic linkage studies; genetic screening; genetic drift and evolution discovery; ancestry investigation; criminal investigation; forensics; criminal profiling; psychological profiling; adoption placement and planning; fertility and pregnancy evaluation and planning; family planning; social services; infrastructure planning; species preservation; organism cloning; organism design and evaluation; apparatus design and evaluation; invention design and evaluation; clinical investigation; epidemiological investigation; etiology investigation; diagnosis, prognosis, treatment, prescription and therapy prediction, formulation and delivery; adverse outcome avoidance (i.e. prophylaxis); data mining; bioinformatics; biomarker development; physiological profiling; rational drug design; drug interaction prediction; drug screening; pharmaceutical formulation; molecular modeling; xenobiotic side-effect prediction; microarray analysis; dietary analysis and recommendation; processed foods formulation; census evaluation and planning; population dynamics assessment; ecological and environmental preservation; environmental health; land management; agriculture planning; crisis and disaster prediction, prevention, planning and analysis; pandemic and epidemic prediction, prevention, planning and analysis; weather forecasting; goal formulation and goal achievement assessment; risk assessment; formulating recommendations; asset management; task management; consulting; marketing and advertising; cost analysis; business development; economics forecasting and planning; stock market prediction; lifestyle modification; time management; emergency intervention; operational/failure status evaluation and prediction; system failure analysis; optimization analysis; architectural design; and product appearance, ergonomics, efficiency, efficacy and reliability engineering (i.e., product development).

The embodiments of the present invention may be implemented with any combination of hardware and software. If implemented as a computer-implemented apparatus, the present invention is implemented using means for performing all of the steps and functions disclosed above.

The embodiments of the present invention can be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present invention is not limited to the particular examples and implementations disclosed herein, but is intended to cover modifications within the spirit and scope thereof as defined by the appended claims and any and all equivalents thereof.

The invention claimed is:

1. A non-transitory computer readable medium comprising:
   (1) a database of attribute profiles, wherein each attribute profile comprises pangenetic and non-pangenetic attributes; and
   (2) a set of instructions that, when executed by a processor, cause that processor to perform the steps of:
   (a) receiving a query attribute;
   (b) selecting, as a positive set, a set of attribute profiles from the database that match the query attribute;
   (c) selecting, as a negative set, a set of attribute profiles from the database that do not match the query attribute;
   (d) identifying, as candidate attributes, attributes from the profiles in the positive set that are not found in a designated fraction of the attribute profiles in the negative set;
   (e) selecting a first attribute profile from the positive set;
   (f) generating a first set of attribute combinations, wherein the first set of attribute combinations comprises an attribute combination for each of the attribute profiles in the positive set, and wherein each attribute combination is the intersection of the first attribute profile with one of the other attribute profiles in the positive set;
   (g) identifying, as a primary attribute combination, the attribute combination generated by step (f) having the greatest number of attributes;
   (h) removing the primary attribute combination from the first set of attribute combinations;
   (j) generating a second set of attribute combinations, wherein the second set of attribute combinations comprises an attribute combination for each of the first set of attribute combinations, and wherein each attribute combination of the second set of attribute combinations is the intersection of the primary attribute combination with one of the attribute combinations in the first set of attribute combinations;
   (k) identifying, as a third set of attribute combinations, those attribute combinations from the second set of attribute combinations that have a number of attributes greater than a designated fraction of the number of attributes of the primary attribute combination;
   (l) identifying, as a third set of attribute profiles, the attribute profiles corresponding to the primary attribute combination plus all attribute profiles matching at least one of the attribute combinations in the third set of attribute combinations;
   (m) designating, as a combination of co-associating attributes, the set of attributes that occur in all attribute profiles of the third set of attribute profiles;
   (n) designating, as a new positive set, the complement of the third set of attribute profiles in the positive set;
   (o) repeating steps (e) through (n) using the new positive set, unless the new positive set is an empty set; and
   (p) storing, in the medium, a compilation comprising the query attribute and each of the combinations of co-associating attributes designated by step (m).

2. A bioinformatics database system, comprising:
   (1) a memory containing a database of attribute profiles, wherein each attribute profile comprises pangenetic and non-pangenetic attributes;
   (2) a processor; and
   (3) a set of instructions that, when executed by the processor, cause the processor to perform the steps of:
   (a) receiving a query attribute;
   (b) selecting, as a positive set, a set of attribute profiles from the database that match the query attribute;
   (c) selecting, as a negative set, a set of attribute profiles from the database that do not match the query attribute;
   (d) identifying, as candidate attributes, attributes from the profiles in the positive set that are not found in a designated fraction of the attribute profiles in the negative set;
   (e) selecting a first attribute profile from the positive set;
   (f) generating a first set of attribute combinations, wherein the first set of attribute combinations comprises an attribute combination for each of the attribute profiles in the positive set, and wherein each attribute combination is the intersection of the first attribute profile with one of the other attribute profiles in the positive set;
   (g) identifying, as a primary attribute combination, the attribute combination generated by step (f) having the greatest number of attributes;
   (h) removing the primary attribute combination from the first set of attribute combinations;
   (j) generating a second set of attribute combinations, wherein the second set of attribute combinations comprises an attribute combination for each of the first set of attribute combinations, and wherein each attribute combination of the second set of attribute combinations is the intersection of the primary attribute combination with one of the attribute combinations in the first set of attribute combinations;
   (k) identifying, as a third set of attribute combinations, those attribute combinations from the second set of attribute combinations that have a number of attributes greater than a designated fraction of the number of attributes of the primary attribute combination;
   (l) identifying, as a third set of attribute profiles, the attribute profiles corresponding to the primary attribute combination plus all attribute profiles matching at least one of the attribute combinations in the third set of attribute combinations;

(m) designating, as a combination of co-associating attributes, the set of attributes that occur in all attribute profiles of the third set of attribute profiles;

(n) designating, as a new positive set, the complement of the third set of attribute profiles in the positive set;

(o) repeating steps (e) through (n) using the new positive set, unless the new positive set is an empty set; and (p) storing, in the memory, a compilation comprising the query attribute and each of the combinations of co-associating attributes designated by step (m).

* * * * *

UNITED STATES PATENT AND TRADEMARK OFFICE
CERTIFICATE OF CORRECTION

| | |
|---|---|
| PATENT NO. | : 7,941,434 B2 |
| APPLICATION NO. | : 12/031669 |
| DATED | : May 10, 2011 |
| INVENTOR(S) | : Kenedy et al. |

Page 1 of 1

It is certified that error appears in the above-identified patent and that said Letters Patent is hereby corrected as shown below:

In the Drawings

In Fig. 11, Sheet 11 of 31, delete "Indvidual attributes:" and insert -- Individual attributes: --, therefor.

In the Specification

In Column 8, Line 39, delete "Prostrate cancer" and insert -- Prostate cancer --, therefor.

In Column 9, Line 47, delete "physical diagnoses class 510.h" and insert -- physical diagnoses class 510.1h --, therefor.

In Column 9, Line 64, delete "heath" and insert -- health --, therefor.

In Column 19, Lines 33-34, delete "one groups" and insert -- one group --, therefor.

In Column 42, Line 31, delete "larger that" and insert -- larger than --, therefor.

In Column 48, Line 18, after "predisposition." delete "that cont".

In Column 48, Line 19, delete "genome ain" and insert -- genome that contain --, therefor.

In Column 54, Line 23, delete "less that" and insert -- less than --, therefor.

In Column 61, Line 3, delete "adaptor" and insert -- adapter --, therefor.

Signed and Sealed this
Fifth Day of November, 2013

Teresa Stanek Rea
*Deputy Director of the United States Patent and Trademark Office*